United States Patent
Li

(10) Patent No.: US 9,719,099 B2
(45) Date of Patent: Aug. 1, 2017

(54) SOYBEAN CCP1 PROMOTER AND ITS USE IN CONSTITUTIVE EXPRESSION OF TRANSGENIC GENES IN PLANTS

(71) Applicant: E. I. DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 247 days.

(21) Appl. No.: 14/418,277

(22) PCT Filed: Aug. 7, 2013

(86) PCT No.: PCT/US2013/053910
§ 371 (c)(1),
(2) Date: Jan. 29, 2015

(87) PCT Pub. No.: WO2014/025860
PCT Pub. Date: Feb. 13, 2014

(65) Prior Publication Data
US 2015/0167011 A1    Jun. 18, 2015

Related U.S. Application Data

(60) Provisional application No. 61/681,759, filed on Aug. 10, 2012.

(51) Int. Cl.
*C12N 15/63* (2006.01)
*C12N 15/82* (2006.01)

(52) U.S. Cl.
CPC ...... *C12N 15/8216* (2013.01); *C12N 15/8209* (2013.01); *C12N 15/8245* (2013.01); *C12N 15/8247* (2013.01); *C12N 15/8251* (2013.01); *C12N 15/8261* (2013.01); *C12N 15/8273* (2013.01); *C12N 15/8274* (2013.01); *C12N 15/8279* (2013.01); *C12N 15/8286* (2013.01)

(58) Field of Classification Search
None
See application file for complete search history.

(56) References Cited

U.S. PATENT DOCUMENTS

| 5,107,065 A | 4/1992 | Shewmaker et al. |
| 5,231,020 A | 7/1993 | Jorgensen et al. |

OTHER PUBLICATIONS

GenBank Accession No. AC235279. Glycine max strain Williams 82 clone GM_WBb0048M07. published Mar. 12, 2009. pp. 1-29.*
Ponappa et al. Transient expression and stable transformation of soybean using the jellyfish green fluorescent protein. Plant Cell Reports. 1999. 19: 6-12.*

(Continued)

*Primary Examiner* — Ashley K Buran

(57) ABSTRACT

The invention relates to gene expression regulatory sequences from soybean, specifically to the promoter of a soybean copper chaperone homolog gene and fragments thereof and their use in promoting the expression of one or more heterologous nucleic acid fragments in a constitutive manner in plants. The invention further discloses compositions, polynucleotide constructs, transformed host cells, transgenic plants and seeds containing the recombinant construct with the promoter, and methods for preparing and using the same.

17 Claims, 15 Drawing Sheets

(56) References Cited

OTHER PUBLICATIONS

Figure 1:
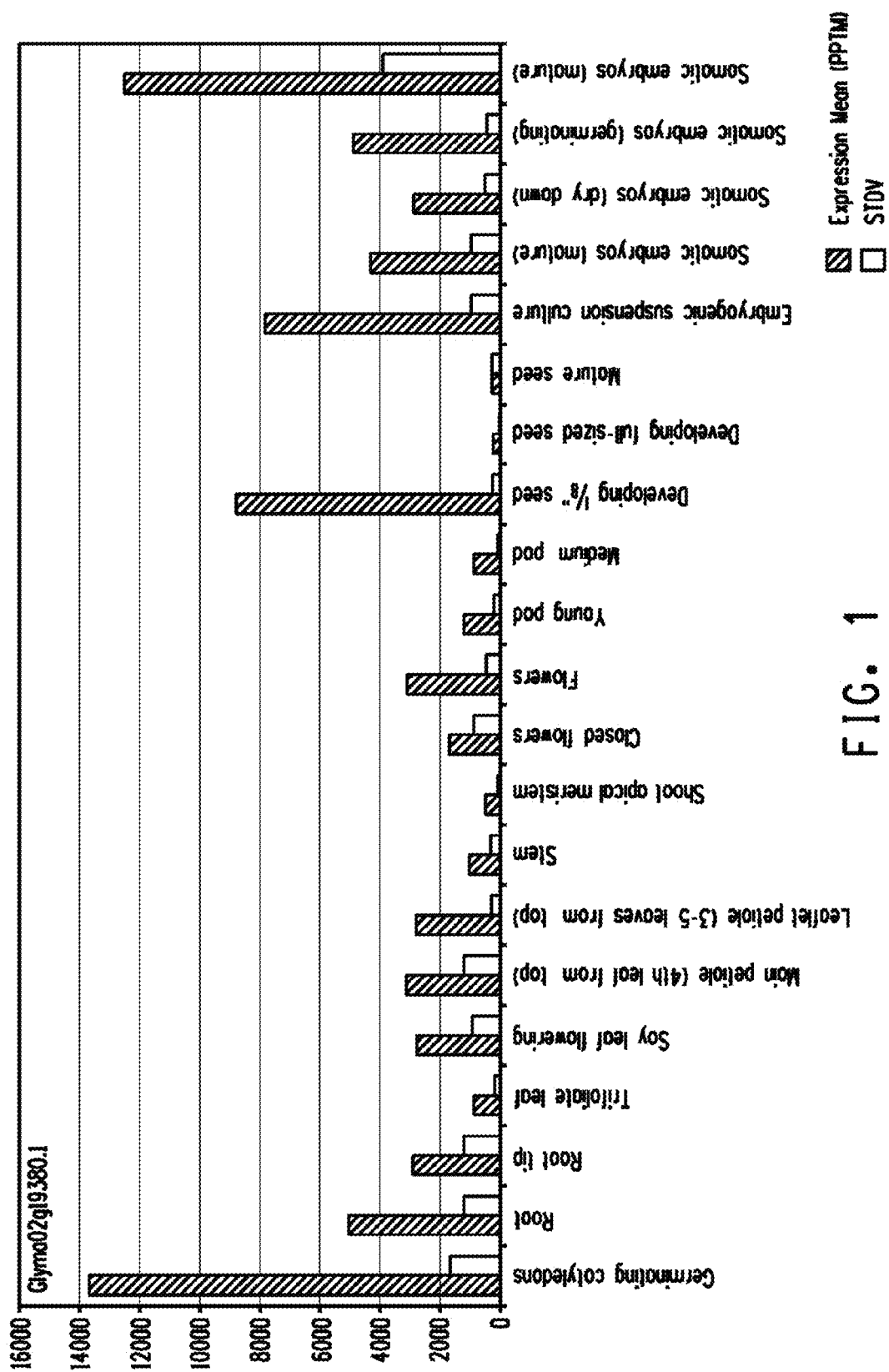

Salah E. Abdel-Ghany et al., AtCCS is a functional homolog of the yeast copper chaperone Cds1/Lys7, FEBS Letters, 2005, pp. 2307-2312, vol. 579.

Rossitza Atanassova et al., Functional analysis of the promoter region of a maize (*Zea mays* L.) H3 histone gene in transgenic Arabidopsis thaliana, Plant Molecuilar Biology, 1998, pp. 275-285, vol. 37.

Carolina V. Attallah et al., The promoters of *Arabidopsis thaliana* genes AtCOX17-1 and -2, encoding a copper chaperone involved in cytochrome c oxidase biogenesis, are preferentially active in roots and anthers and induced by biotic and abiotic stress, Physiologia Plantarum, 2007, pp. 123-134, vol. 129.

Teresa Balandin et al., At COX17, an Arabidopsis Homolog of the Yeast Copper Chaperone COX17[1], Plant Physiol., 2002, pp. 1852-1857, vol. 129.

Michael J. Battraw et al., Histochemical analysis of CaMV 35S promoter-β-glucuronidase gene expression in transgenic rice plants, Plant Molecular Biology, 1990, pp. 527-538, vol. 15.

Mark D. Harrison et al., Intracellular copper routing: the role of copper chaperones, TIBS 25, Jan. 2000, pp. 29-32.

Edward Himelblau et al., Identification of a Functional Homolog of the Yeast Copper Homeostasis Gene ATX1 from Arabidopsis[1] Plant Physiol, 1998, pp. 1227-1234, vol. 117.

Hui-Liant Li et al., Cloning and molecular characterization of a copper chaperone gene (HbCCH1) from Hevea brasiliensis, African Journal of Biotechnology, Jun. 20, 2011, pp. 5438-5443, vol. 10(28).

Mikhail V. Matz et al., Fluorescent proteins from nonbioluminescent *Anthozoa* species, Nature Biotechnology, Oct. 1999, pp. 969-973, vol. 17.

Jeremy Schmutz et al., Genome sequence of the palaeopolyploid soybean, Nature, Jan. 2010, pp. 178-183, vol. 463.

Iris Steinebrunner et al., HCC1 the Arabidopsis homologue of the yeast mitochondrial copper chaperone SC01, is essential for embryonic development, Journal of Experimental Botany, 2011, pp. 319-330, vol. 62 No. 1.

Luisa M. Trindade et al., Isolation of a Gene Encoding a Copper Chaperone for the Copper/Zinc Superoxide Dismutase and Characterization of Its Promoter in Potato, Plant Physiology, Oct. 2003, pp. 618-629, vol. 133.

Roger Y. Tsien, The Green Fluorescent Protein, Annu. Rev. Biochem., 1998, pp. 509-544, vol. 67.

Database EMBL Accession No. EI324267, XP002714293, Feb. 17, 2007.

Database EMBL Accession No. CA783341, XP002714294, Dec. 12, 2002.

International Search Report for PCT/US2013/053910.

\* cited by examiner

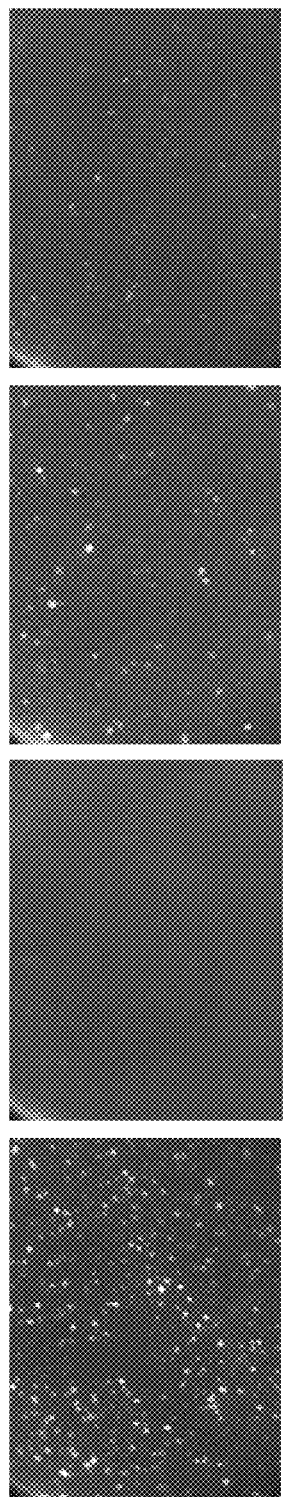
FIG. 6A pZSL90
FIG. 6B QC330-Y
FIG. 6C QC532-1Y
FIG. 6D QC532-2Y
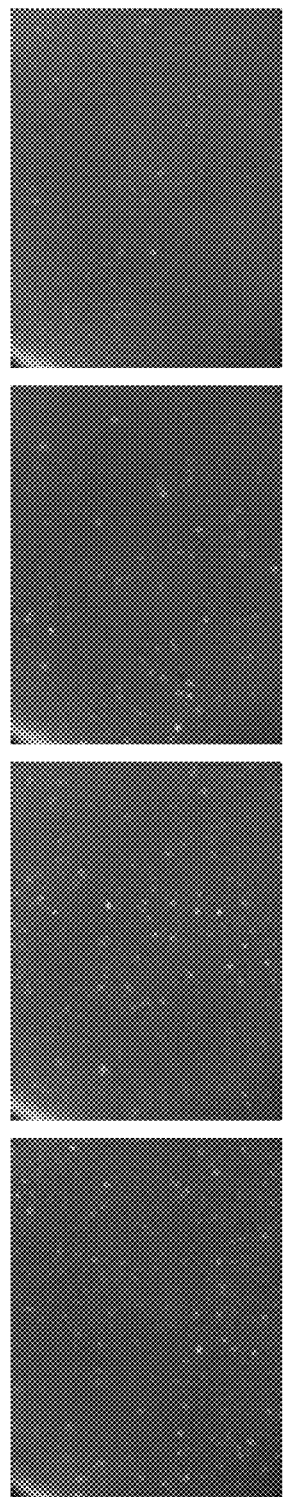
FIG. 6E QC532-3Y
FIG. 6F QC532-4Y
FIG. 6G QC532-5Y
FIG. 6H QC532-6Y

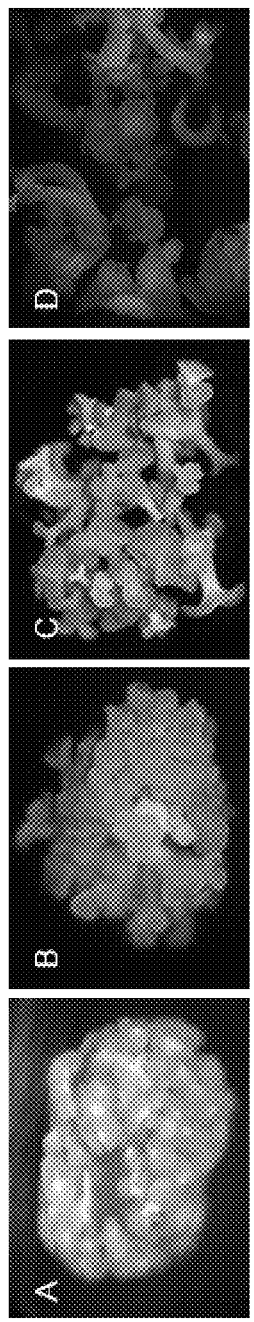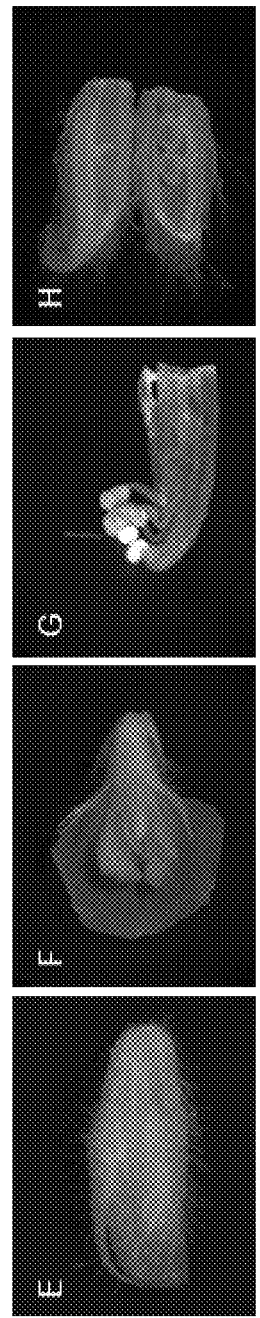

Percent Identity

|   | 1 | 2 |   |
|---|---|---|---|
| 1 |   | 99.7 | 1 |
| 2 | 0.3 |   | 2 |
|   | 1 | 2 |   |

Divergence

SEQ ID NO-1.seq

SEQ ID NO-42.seq

FIG. 8D

SEQUENCE LISTING

<160> NUMBER OF SEQ ID NOS: 43

<210> SEQ ID NO 1
<211> LENGTH: 1524

<212> TYPE: DNA
<213> ORGANISM: Glycine max

<400> SEQUENCE: 1

```
cccgggagaa aattacctaa gtgtcatgtg caagtacaat tatgaattca attttttaaac    60
atgtctatat gaaaaaatat ttattaagac aagtttgtct cttaaatata tcttaatacc   120
ttaaaagatt aattattagt tctcgatcag aatatcctaa gttaaaaata aataaataaa   180
taaaacaaca aaaattgaag caaacaataa ccattaaata aagtttaatc tgtaacgtgg   240
attacaagtg gtgaaaattt ataaatctgg attcgacttt ttcttatgcc acttagtgga   300
caactttctt caaagaattc tcgtattgct ctggcgcagt tgagtaagtc tatgtttggt   360
ttacagatgg ggagttttaa actcaatttg aagagaaaaa tgagtttaac attatgttta   420
atttctctct aaaaatatgt ttaaagttaa aatttagcct gaaaacttac ttagggagac   480
acaactatta gaatattttt gcaaactgca atccaaattt tgagtttaaa attttgcctc   540
aacactcaat ttgggaaaaa caactattag gatattcttg caaatttagt ttgtaaactt   600
aagtttaact taaacttaaa tttggaaact gtaatccaaa catgtccttg tattcctgtg   660
aattgaaggt gcctctccca cctttttacca ataaaaataa aaagttgaat ctattaacgc   720
tacattcgtt gttatccatt aggcgcactc caaagctttt atatttcgat ctaagcatta   780
tctctcaaaa gttgtaccgg aaaaacgttg ccatcgtacg tgagaagaaa gattttcacg   840
taaattactt tttcgttaga ttatatttta gtccttatat ttctattatt ttttaaataa   900
aaacttacaa tcctcacttt atatatatta aaataggtgt tttaaaaata ataattttag   960
aaactattct tcaatgacaa catctttaag aattttctcc aacaaaaatg tttttaggta  1020
tttttctaat ctattatctc ttttaatcca tcactctcat atacacctttt aaattattaa  1080
agtctattaa aaaataaata aaaatataag aagctatcta gagaataatt tatcctaaat  1140
tcttttttata cgatacatta tatgtggagc acattaggat aaaggaaaaa aagaaaacgt  1200
tagctaggca aattaaaata ataacaaaaa tcttgataaa acgtttaatt tgaaccaaga  1260
atgaaaatca aacgtaaaca agaaaatgaa taataaatac caatctacag tggcccacca  1320
aattgccttc tttgcggaat cctactgttc tgtcttgcac cacacgcact ctcacaatgg  1380
gtggtttggc tataaagaca ccactcttac acccctttc agcattcacc acaaccctct  1440
ctctatattc cattgccacc cagttttgaa tatatttta ttccttctttt gtttcttcac   1500
tttcttccat acacataacc atgg                                         1524
```

<210> SEQ ID NO 2
<211> LENGTH: 1516
<212> TYPE: DNA
<213> ORGANISM: Glycine max

<400> SEQUENCE: 2

```
gggagaaaat tacctaagtg tcatgtgcaa gtacaattat gaattcaatt tttaaacatg    60
tctatatgaa aaaatattta ttaagacaag tttgtctctt aaatatatct taataccttta  120
aaagattaat tattagttct cgatcagaat atcctaagtt aaaaataaat aataaataa   180
aacaacaaaa attgaagcaa acaataacca ttaaataaag tttaatctgt aacgtggatt   240
acaagtggtg aaaatttata atctggatt cgacttttc ttatgccact tagtggacaa   300
ctttcttcaa agaattctcg tattgctctg gcgcagttga gtaagtctat gtttggttta   360
cagatgggga gttttaaact caatttgaag agaaaaatga gtttaacatt atgtttaatt   420
```

-continued

```
tctctctaaa aatatgttta aagttaaaat ttagcctgaa aacttactta gggagacaca        480
actattagaa tattttttgca aactgcaatc caaattttga gtttaaaatt ttgcctcaac        540
actcaatttg ggaaaaacaa ctattaggat attcttgcaa atttagtttg taaacttaag        600
tttaacttaa acttaaattt ggaaactgta atccaaacat gtccttgtat tcctgtgaat        660
tgaaggtgcc tctcccacct tttaccaata aaaataaaaa gttgaatcta ttaacgctac        720
attcgttgtt atccattagg cgcactccaa agctttata tttcgatcta agcattatct         780
ctcaaaagtt gtaccggaaa aacgttgcca tcgtacgtga agaaagat tttcacgtaa          840 attactttttt cgttagatta tattttagtc cttatatttc tattattttt taaataaaaa       900
cttacaatcc tcactttata tatattaaaa taggtgtttt aaaataata attttagaaa         960 ctattcttca atgacaacat ctttaagaat tttctccaac aaaaatgttt ttaggtattt       1020
ttctaatcta ttatctcttt taatccatca ctctcatata cacctttaaa ttattaaagt      1080
ctattaaaaa ataaataaaa atataagaag ctatctagag aataatttat cctaaattct      1140
ttttatacga tacattatat gtggagcaca ttaggataaa ggaaaaaaag aaaacgttag      1200
ctaggcaaat taaataata acaaaaatct tgataaaacg tttaatttga accaagaatg      1260
aaaatcaaac gtaaacaaga aaatgaataa taaataccaa tctacagtgg cccaccaaat      1320
tgccttcttt gcggaatcct actgttctgt cttgcaccac acgcactctc acaatgggtg      1380
gtttggctat aaagacacca ctcttacaca cccttccagc attcaccaca acctctctc       1440 tatattccat tgccacccag ttttgaatat attttttattc cttctttgtt tcttcactt       1500 cttccataca cataac                                                       1516

<210> SEQ ID NO 3
<211> LENGTH: 1186
<212> TYPE: DNA
<213> ORGANISM: Glycine max

<400> SEQUENCE: 3
gcgcagttga gtaagtctat gtttggttta cagatgggga gttttaaaact caatttgaag        60 agaaaaatga gtttaacatt atgtttaatt tctctctaaa aatatgttta aagttaaaat       120
ttagcctgaa aacttactta gggagacaca actattagaa tattttttgca aactgcaatc      180 caaattttga gtttaaaatt ttgcctcaac actcaatttg ggaaaaacaa ctattaggat       240
attcttgcaa atttagtttg taaacttaag tttaacttaa acttaaattt ggaaactgta       300
atccaaacat gtccttgtat tcctgtgaat tgaaggtgcc tctcccacct tttaccaata       360
aaaataaaaa gttgaatcta ttaacgctac attcgttgtt atccattagg cgcactccaa       420 agctttata tttcgatcta agcattatct ctcaaaagtt gtaccggaaa aacgttgcca        480
tcgtacgtga agaaagat tttcacgtaa attactttttt cgttagatta tattttagtc       540
cttatatttc tattattttt taaataaaaa cttacaatcc tcactttata tatattaaaa       600
taggtgtttt aaaataata attttagaaa ctattcttca atgacaacat ctttaagaat       660
tttctccaac aaaaatgttt ttaggtattt ttctaatcta ttatctcttt taatccatca      720
ctctcatata cacctttaaa ttattaaagt ctattaaaaa ataaataaaa atataagaag      780
ctatctagag aataatttat cctaaattct ttttatacga tacattatat gtggagcaca      840
ttaggataaa ggaaaaaaag aaaacgttag ctaggcaaat taaataata acaaaaatct      900 tgataaaacg tttaatttga accaagaatg aaaatcaaac gtaaacaaga aaatgaataa      960
taaataccaa tctacagtgg cccaccaaat tgccttcttt gcggaatcct actgttctgt     1020
```

| cttgcaccac acgcactctc acaatgggtg gtttggctat aaagacacca ctcttacaca | 1080 |
| cccttcagc attcaccaca accctctctc tatattccat tgccaccag ttttgaatat | 1140 |
| atttttattc cttctttgtt tcttcacttt cttccataca cataac | 1186 |

<210> SEQ ID NO 4
<211> LENGTH: 987
<212> TYPE: DNA
<213> ORGANISM: Glycine max

<400> SEQUENCE: 4

| tttgcctcaa cactcaattt gggaaaaaca actattagga tattcttgca aatttagttt | 60 |
| gtaaacttaa gtttaactta aacttaaatt tggaaactgt aatccaaaca tgtccttgta | 120 |
| ttcctgtgaa ttgaaggtgc ctctcccacc ttttaccaat aaaaataaaa agttgaatct | 180 |
| attaacgcta cattcgttgt tatccattag gcgcactcca aagcttttat atttcgatct | 240 |
| aagcattatc tctcaaaagt tgtaccggaa aaacgttgcc atcgtacgtg agaagaaaga | 300 |
| ttttcacgta aattacttt tcgttagatt atatttagt ccttatattt ctattatttt | 360 |
| ttaaataaaa acttacaatc ctcactttat atatattaaa ataggtgttt taaaaataat | 420 |
| aattttagaa actattcttc aatgacaaca tctttaagaa ttttctccaa caaaaatgtt | 480 |
| tttaggtatt tttctaatct attatctctt ttaatccatc actctcatat caccctttaa | 540 |
| attattaaag tctattaaaa aataaataaa aatataagaa gctatctaga gaataattta | 600 |
| tcctaaattc tttttatacg atacattata tgtggagcac attaggataa aggaaaaaaa | 660 |
| gaaaacgtta gctaggcaaa ttaaaataat aacaaaatc ttgataaaac gtttaatttg | 720 |
| aaccaagaat gaaaatcaaa cgtaaacaag aaaatgaata ataaatacca atctacagtg | 780 |
| gcccaccaaa ttgccttctt tgcggaatcc tactgttctg tcttgcacca cacgcactct | 840 |
| cacaatgggt ggtttggcta taaagacacc actcttacac accctttcag cattcaccac | 900 |
| aaccctctct ctatattcca ttgccaccca gttttgaata tatttttatt ccttctttgt | 960 |
| ttcttcactt tcttccatac acataac | 987 |

<210> SEQ ID NO 5
<211> LENGTH: 747
<212> TYPE: DNA
<213> ORGANISM: Glycine max

<400> SEQUENCE: 5

| aagcattatc tctcaaaagt tgtaccggaa aaacgttgcc atcgtacgtg agaagaaaga | 60 |
| ttttcacgta aattactttt tcgttagatt atatttagt ccttatattt ctattatttt | 120 |
| ttaaataaaa acttacaatc ctcactttat atatattaaa ataggtgttt taaaaataat | 180 |
| aattttagaa actattcttc aatgacaaca tctttaagaa ttttctccaa caaaaatgtt | 240 |
| tttaggtatt tttctaatct attatctctt ttaatccatc actctcatat caccctttaa | 300 |
| attattaaag tctattaaaa aataaataaa aatataagaa gctatctaga gaataattta | 360 |
| tcctaaattc tttttatacg atacattata tgtggagcac attaggataa aggaaaaaaa | 420 |
| gaaaacgtta gctaggcaaa ttaaaataat aacaaaatc ttgataaaac gtttaatttg | 480 |
| aaccaagaat gaaaatcaaa cgtaaacaag aaaatgaata ataaatacca atctacagtg | 540 |
| gcccaccaaa ttgccttctt tgcggaatcc tactgttctg tcttgcacca cacgcactct | 600 |
| cacaatgggt ggtttggcta taaagacacc actcttacac accctttcag cattcaccac | 660 |

```
aaccctctct ctatattcca ttgccaccca gttttgaata tattttatt ccttctttgt      720 ttcttcactt tcttccatac acataac                                         747

<210> SEQ ID NO 6
<211> LENGTH: 484
<212> TYPE: DNA
<213> ORGANISM: Glycine max

<400> SEQUENCE: 6
atctctttta atccatcact ctcatataca cctttaaatt attaaagtct attaaaaaat      60
aaataaaaat ataagaagct atctagagaa taatttatcc taaattcttt ttatacgata     120
cattatatgt ggagcacatt aggataaagg aaaaaaagaa aacgttagct aggcaaatta     180
aaataataac aaaaatcttg ataaaacgtt taatttgaac caagaatgaa atcaaacgt     240 aaacaagaaa atgaataata ataccaatc tacagtggcc caccaaattg ccttctttgc     300
ggaatcctac tgttctgtct tgcaccacac gcactctcac aatgggtggt ttggctataa     360
agacaccact cttacacacc cttcagcat tcaccacaac cctctctcta tattccattg     420
ccacccagtt ttgaatatat ttttattcct tctttgtttc ttcactttct tccatacaca     480
taac                                                                  484

<210> SEQ ID NO 7
<211> LENGTH: 225
<212> TYPE: DNA
<213> ORGANISM: Glycine max

<400> SEQUENCE: 7
aaataccaat ctacagtggc ccaccaaatt gccttctttg cggaatccta ctgttctgtc      60
ttgcaccaca cgcactctca caatgggtgg tttggctata agacaccac tcttacacac     120 ccttcagca ttcaccacaa ccctctctct atattccatt gccacccagt ttgaatata     180 tttttattcc ttctttgttt cttcacttc ttccatacac ataac                      225

<210> SEQ ID NO 8
<211> LENGTH: 37
<212> TYPE: DNA
<213> ORGANISM: Artificial Sequence
<220> FEATURE:
<223> OTHER INFORMATION: primer, PSO319685Xma

<400> SEQUENCE: 8
actataaccc gggagaaaat tacctaagtg tcatgtg                               37

<210> SEQ ID NO 9
<211> LENGTH: 35
<212> TYPE: DNA
<213> ORGANISM: Artificial Sequence
<220> FEATURE:
<223> OTHER INFORMATION: primer, PSO319685Nco

<400> SEQUENCE: 9
tgtaaatcca tggttatgtg tatggaagaa agtga                                 35

<210> SEQ ID NO 10
<211> LENGTH: 31
<212> TYPE: DNA
<213> ORGANISM: Artificial Sequence
<220> FEATURE:
<223> OTHER INFORMATION: primer, QC533-A

<400> SEQUENCE: 10
```
gttatgtgta tggaagaaag tgaagaaaca a                                      31

<210> SEQ ID NO 11
<211> LENGTH: 28
<212> TYPE: DNA
<213> ORGANISM: Artificial Sequence
<220> FEATURE:
<223> OTHER INFORMATION: primer, QC533-S1

<400> SEQUENCE: 11
gggagaaaat tacctaagtg tcatgtgc                                         28

<210> SEQ ID NO 12
<211> LENGTH: 26
<212> TYPE: DNA
<213> ORGANISM: Artificial Sequence
<220> FEATURE:
<223> OTHER INFORMATION: primer, QC533-S2

<400> SEQUENCE: 12
gcgcagttga gtaagtctat gtttgg                                           26

<210> SEQ ID NO 13
<211> LENGTH: 24
<212> TYPE: DNA
<213> ORGANISM: Artificial Sequence
<220> FEATURE:
<223> OTHER INFORMATION: primer, QC533-S3

<400> SEQUENCE: 13
tttgcctcaa cactcaattt ggga                                             24

<210> SEQ ID NO 14
<211> LENGTH: 28
<212> TYPE: DNA
<213> ORGANISM: Artificial Sequence
<220> FEATURE:
<223> OTHER INFORMATION: primer, QC533-S4

<400> SEQUENCE: 14
aagcattatc tctcaaaagt tgtaccgg                                         28

<210> SEQ ID NO 15
<211> LENGTH: 32
<212> TYPE: DNA
<213> ORGANISM: Artificial Sequence
<220> FEATURE:
<223> OTHER INFORMATION: primer, QC533-S5

<400> SEQUENCE: 15 atctcttta atccatcact ctcatataca cc                                     32

<210> SEQ ID NO 16
<211> LENGTH: 25
<212> TYPE: DNA
<213> ORGANISM: Artificial Sequence
<220> FEATURE:
<223> OTHER INFORMATION: primer, QC533-S6

<400> SEQUENCE: 16
aaataccaat ctacagtggc ccacc                                            25

<210> SEQ ID NO 17
<211> LENGTH: 673
<212> TYPE: DNA

<213> ORGANISM: Glycine max

<400> SEQUENCE: 17

```
cacaaccctc tctctatatt ccattgccac ccagttttga atatattttt attccttctt      60
tgtttcttca ctttcttcca tacacataac catgtcttct cagactgttg tcctcaaagt     120
tggtatgtca tgtcaagggt gtgctggagc agtgaacagg ttttgggaa aaatggaagg      180
tgttgagtca tttgacattg atctgaagga gcagaaggtg acagtgaaag gaaatgtgga     240
gccagatgaa gttctgcaag ccgtttccaa atctgggaag aagactgcat tctgggtgga     300
tgaagcacca caatctaaaa acaagccttt agaaagtgca cctgttgcct cagaaaacaa     360
gccttcagaa gctgcaactg ttgcctcagc tgagcctgaa aacaagcctt cagaagctgc     420
aattgttgat tcagctgagc ctgaaaacaa gccttcagat actgttgttg aaactgttgc     480
ttaaggcatt tgtggttcta tttttctatg tggaagtagg tctgtttcat atagtatttc     540
atgtgctttg tgcatgtcag ctattatatt tggtgtgttg ttactggtat ctaagctaca     600
ataacttgtg gccatttttt cacatgagat acatttcatg ggtgctataa tttagaattt     660
gaacctgtca ctc                                                        673
```

<210> SEQ ID NO 18
<211> LENGTH: 130
<212> TYPE: PRT
<213> ORGANISM: Glycine max

<400> SEQUENCE: 18

| Met | Ser | Ser | Gln | Thr | Val | Val | Leu | Lys | Val | Gly | Met | Ser | Cys | Gln | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Ala | Gly | Ala | Val | Asn | Arg | Val | Leu | Gly | Lys | Met | Glu | Gly | Val | Glu |
|-----|-----|-----|-----|-----|-----|-----|-----|-----|-----|-----|-----|-----|-----|-----|-----|
|     |     |     | 20  |     |     |     | 25  |     |     |     |     | 30  |     |     |     |

| Ser | Phe | Asp | Ile | Asp | Leu | Lys | Glu | Gln | Lys | Val | Thr | Val | Lys | Gly | Asn |
|     |     |     | 35  |     |     |     | 40  |     |     |     | 45  |     |     |     |     |

| Val | Glu | Pro | Asp | Glu | Val | Leu | Gln | Ala | Val | Ser | Lys | Ser | Gly | Lys | Lys |
| 50  |     |     |     |     | 55  |     |     |     |     | 60  |     |     |     |     |     |

| Thr | Ala | Phe | Trp | Val | Asp | Glu | Ala | Pro | Gln | Ser | Lys | Asn | Lys | Pro | Leu |
| 65  |     |     |     | 70  |     |     |     |     | 75  |     |     |     |     | 80  |     |

| Glu | Ser | Ala | Pro | Val | Ala | Ser | Glu | Asn | Lys | Pro | Ser | Glu | Ala | Ala | Thr |
|     |     |     | 85  |     |     |     |     | 90  |     |     |     |     | 95  |     |     |

| Val | Ala | Ser | Ala | Glu | Pro | Glu | Asn | Lys | Pro | Ser | Glu | Ala | Ala | Ile | Val |
|     |     |     | 100 |     |     |     |     | 105 |     |     |     |     | 110 |     |     |

| Asp | Ser | Ala | Glu | Pro | Glu | Asn | Lys | Pro | Ser | Asp | Thr | Val | Val | Glu | Thr |
|     |     |     | 115 |     |     |     |     | 120 |     |     |     |     | 125 |     |     |

| Val | Ala |
|     | 130 |

<210> SEQ ID NO 19
<211> LENGTH: 4830
<212> TYPE: DNA
<213> ORGANISM: Artificial Sequence
<220> FEATURE:
<223> OTHER INFORMATION: plasmid QC533

<400> SEQUENCE: 19

```
cccgggagaa aattacctaa gtgtcatgtg caagtacaat tatgaattca atttttaaac      60
atgtctatat gaaaaaatat ttattaagac aagtttgtct cttaaatata tcttaatacc     120
ttaaaagatt aattattagt tctcgatcag aatatcctaa gttaaaaata aataaataaa     180
```

-continued

| | |
|---|---|
| taaaacaaca aaaattgaag caaacaataa ccattaaata aagtttaatc tgtaacgtgg | 240 |
| attacaagtg gtgaaaattt ataaatctgg attcgacttt ttcttatgcc acttagtgga | 300 |
| caactttctt caaagaattc tcgtattgct ctggcgcagt tgagtaagtc tatgtttggt | 360 |
| ttacagatgg ggagttttaa actcaatttg aagagaaaaa tgagtttaac attatgttta | 420 |
| atttctctct aaaaatatgt ttaaagttaa aatttagcct gaaaacttac ttagggagac | 480 |
| acaactatta gaatatttt gcaaactgca atccaaattt tgagtttaaa attttgcctc | 540 |
| aacactcaat ttgggaaaaa caactattag gatattcttg caaatttagt ttgtaaactt | 600 |
| aagtttaact taaacttaaa tttgaaaact gtaatccaaa catgtccttg tattcctgtg | 660 |
| aattgaaggt gcctctccca ccttttacca ataaaaataa aaagttgaat ctattaacgc | 720 |
| tacattcgtt gttatccatt aggcgcactc caaagctttt atatttcgat ctaagcatta | 780 |
| tctctcaaaa gttgtaccgg aaaaacgttg ccatcgtacg tgagaagaaa gattttcacg | 840 |
| taaattactt tttcgttaga ttatattta gtccttatat ttctattatt ttttaaataa | 900 |
| aaacttacaa tcctcacttt atatatatta aaataggtgt tttaaaaata ataattttag | 960 |
| aaactattct tcaatgacaa catcttttaag aattttctcc aacaaaaatg ttttttaggta | 1020 |
| tttttctaat ctattatctc ttttaatcca tcactctcat atacacctt aaattattaa | 1080 |
| agtctattaa aaaatataa aaaatataag aagctatcta gagaataatt tatcctaaat | 1140 |
| tcttttata cgatacatta tatgtggagc acattaggat aaaggaaaaa aagaaaacgt | 1200 |
| tagctaggca aattaaaata ataacaaaaa tcttgataaa acgtttaatt tgaaccaaga | 1260 |
| atgaaaatca aacgtaaaca agaaaatgaa taataaatac caatctacag tggcccacca | 1320 |
| aattgccttc tttgcggaat cctactgttc tgtcttgcac cacacgcact ctcacaatgg | 1380 |
| gtggtttggc tataaagaca ccactcttac acacccttc agcattcacc acaaccctct | 1440 |
| ctctatattc cattgccacc cagttttgaa tatattttta ttccttcttt gtttcttcac | 1500 |
| tttcttccat acacataacc atgggcccaca gcaagcacgg cctgaaggag gagatgacca | 1560 |
| tgaagtacca catggagggc tgcgtgaacg ccacaagtt cgtgatcacc ggcgagggca | 1620 |
| tcggctaccc cttcaagggc aagcagacca tcaacctgtg cgtgatcgag gcggccccc | 1680 |
| tgcccttcag cgaggacatc ctgagcgccg gcttcaagta cggcgaccgg atcttcaccg | 1740 |
| agtaccccca ggacatcgtg gactacttca gaacagctg ccccgccggc tacacctggg | 1800 |
| gccggagctt cctgttcgag gacggcgccg tgtgcatctg taacgtggac atcaccgtga | 1860 |
| gcgtgaagga gaactgcatc taccacaaga gcatcttcaa cggcgtgaac ttccccgccg | 1920 |
| acggccccgt gatgaagaag atgaccacca actgggaggc cagctgcgag aagatcatgc | 1980 |
| ccgtgcctaa gcagggcatc ctgaagggcg acgtgagcat gtacctgctg ctgaaggacg | 2040 |
| gcggccggta ccggtgccag ttcgacaccg tgtacaaggc caagagcgtg cccagcaaga | 2100 |
| tgcccgagtg gcacttcatc cagcacaagc tgctgcggga ggaccggagc gacgccaaga | 2160 |
| accagaagtg gcagctgacc gagcacgcca tcgccttccc cagcgccctg gcctgagagc | 2220 |
| tcgaatttcc ccgatcgttc aaacatttgg caataaagtt tcttaagatt gaatcctgtt | 2280 |
| gccggtcttg cgatgattat catataattt ctgttgaatt acgttaagca tgtaataatt | 2340 |
| aacatgtaat gcatgacgtt atttatgaga tgggttttta tgattagagt cccgcaatta | 2400 |
| tacatttaat acgcgataga aaacaaaata tagcgcgcaa actaggataa attatcgcgc | 2460 |
| gcggtgtcat ctatgttact agatcgggaa ttctagtggc cggcccagct gatatccatc | 2520 |
| acactggcgg ccgcactcga ctgaattggt tccggcgcca gcctgctttt ttgtacaaag | 2580 |

```
ttggcattat aaaaaagcat tgcttatcaa tttgttgcaa cgaacaggtc actatcagtc      2640
aaaataaaat cattatttgg ggcccgagct taagtaacta actaacagga agagtttgta      2700
gaaacgcaaa aaggccatcc gtcaggatgg ccttctgctt agtttgatgc ctggcagttt      2760
atggcgggcg tcctgcccgc caccctccgg gccgttgctt cacaacgttc aaatccgctc      2820
ccggcggatt tgtcctactc aggagagcgt tcaccgacaa acaacagata aaacgaaagg      2880
cccagtcttc cgactgagcc tttcgtttta tttgatgcct ggcagttccc tactctcgct      2940
tagtagttag acgtccccga gatccatgct agcggtaata cggttatcca cagaatcagg      3000
ggataacgca ggaaagaaca tgtgagcaaa aggccagcaa aaggccagga accgtaaaaa      3060
ggccgcgttg ctggcgtttt tccataggct ccgcccccct gacgagcatc acaaaaatcg      3120
acgctcaagt cagaggtggc gaaacccgac aggactataa agataccagg cgtttccccc      3180
tggaagctcc ctcgtgcgct ctcctgttcc gaccctgccg cttaccggat acctgtccgc      3240
ctttctccct tcgggaagcg tggcgctttc tcatagctca cgctgtaggt atctcagttc      3300
ggtgtaggtc gttcgctcca agctgggctg tgtgcacgaa ccccccgttc agcccgaccg      3360
ctgcgcctta tccggtaact atcgtcttga gtccaacccg gtaagacacg acttatcgcc      3420
actggcagca gccactggta acaggattag cagagcgagg tatgtaggcg gtgctacaga      3480
gttcttgaag tggtggccta actacggcta cactagaaga acagtatttg gtatctgcgc      3540
tctgctgaag ccagttacct tcggaaaaag agttggtagc tcttgatccg gcaaacaaac      3600
caccgctggt agcggtggtt tttttgtttg caagcagcag attacgcgca gaaaaaaagg      3660
atctcaagaa gatcctttga tcttttctac ggggtctgac gctcagtgga acggggccca      3720
atctgaataa tgttacaacc aattaaccaa ttctgattag aaaaactcat cgagcatcaa      3780
atgaaactgc aatttattca tatcaggatt atcaatacca tatttttgaa aaagccgttt      3840
ctgtaatgaa ggagaaaact caccgaggca gttccatagg atggcaagat cctggtatcg      3900
gtctgcgatt ccgactcgtc aacatcaat acaacctatt aatttcccct cgtcaaaaat      3960
aaggttatca agtgagaaat caccatgagt gacgactgaa tccggtgaga atggcaaaag      4020
tttatgcatt tctttccaga cttgttcaac aggccagcca ttacgctcgt catcaaaatc      4080
actcgcatca accaaaccgt tattcattcg tgattgcgcc tgagcgagac gaaatacgcg      4140
atcgctgtta aaaggacaat tacaaacagg aatcgaatgc aaccggcgca ggaacactgc      4200
cagcgcatca acaatatttt cacctgaatc aggatattct tctaatacct ggaatgctgt      4260
ttttccgggg atcgcagtgg tgagtaacca tgcatcatca ggagtacgga taaaatgctt      4320
gatggtcgga agaggcataa attccgtcag ccagtttagt ctgaccatct catctgtaac      4380
atcattggca acgctacctt tgccatgttt cagaaacaac tctggcgcat cgggcttccc      4440
atacaagcga tagattgtcg cacctgattg cccgacatta tcgcgagccc atttataccc      4500
atataaatca gcatccatgt tggaatttaa tcgcggcctc gacgtttccc gttgaatatg      4560
gctcataaca ccccttgtat tactgtttat gtaagcagac agttttattg ttcatgatga      4620 tatatttta tcttgtgcaa tgtaacatca gagattttga gacacgggcc agagctgcag      4680
ctggatggca ataatgatt ttattttgac tgatagtgac ctgttcgttg caacaaattg      4740
ataagcaatg ctttcttata atgccaactt tgtacaagaa agctgggtct agatatctcg      4800
acccatctgc agaattcgcc cttactataa                                      4830
```

<210> SEQ ID NO 20

<211> LENGTH: 4867
<212> TYPE: DNA
<213> ORGANISM: Artificial Sequence
<220> FEATURE:
<223> OTHER INFORMATION: plasmid QC636

<400> SEQUENCE: 20

| | | | | | |
|---|---|---|---|---|---|
| cccgggagaa | aattacctaa | gtgtcatgtg | caagtacaat | tatgaattca | attttaaaac | 60 |
| atgtctatat | gaaaaaatat | ttattaagac | aagtttgtct | cttaaatata | tcttaatacc | 120 |
| ttaaaagatt | aattattagt | tctcgatcag | aatatcctaa | gttaaaaata | aataaataaa | 180 |
| taaaacaaca | aaaattgaag | caaacaataa | ccattaaata | aagtttaatc | tgtaacgtgg | 240 |
| attacaagtg | gtgaaaattt | ataaatctgg | attcgacttt | ttcttatgcc | acttagtgga | 300 |
| caactttctt | caaagaattc | tcgtattgct | ctggcgcagt | tgagtaagtc | tatgtttggt | 360 |
| ttacagatgg | ggagttttaa | actcaatttg | aagagaaaaa | tgagtttaac | attatgttta | 420 |
| atttctctct | aaaatatgt | ttaaagttaa | aatttagcct | gaaaacttac | ttagggagac | 480 |
| acaactatta | gaatatttt | gcaaactgca | atccaaattt | tgagtttaaa | attttgcctc | 540 |
| aacactcaat | ttgggaaaaa | caactattag | gatattcttg | caaatttagt | ttgtaaactt | 600 |
| aagtttaact | taaacttaaa | tttggaaact | gtaatccaaa | catgtccttg | tattcctgtg | 660 |
| aattgaaggt | gcctctccca | ccttttacca | ataaaaataa | aaagttgaat | ctattaacgc | 720 |
| tacattcgtt | gttatccatt | aggcgcactc | caaagctttt | atatttcgat | ctaagcatta | 780 |
| tctctcaaaa | gttgtaccgg | aaaaacgttg | ccatcgtacg | tgagaagaaa | gattttcacg | 840 |
| taaattactt | tttcgttaga | ttatatttta | gtccttatat | ttctattatt | ttttaaataa | 900 |
| aaacttacaa | tcctcacttt | atatatatta | aaataggtgt | tttaaaaata | ataattttag | 960 |
| aaactattct | tcaatgacaa | catcttaag | aattttctcc | aacaaaaatg | tttttaggta | 1020 |
| tttttctaat | ctattatctc | ttttaatcca | tcactctcat | atacaccttt | aaattattaa | 1080 |
| agtctattaa | aaaataaata | aaaatataag | aagctatcta | gagaataatt | tatcctaaat | 1140 |
| tctttttata | cgatacatta | tatgtggagc | acattaggat | aaaggaaaaa | agaaaacgt | 1200 |
| tagctaggca | aattaaaata | ataacaaaaa | tcttgataaa | acgtttaatt | tgaaccaaga | 1260 |
| atgaaaatca | aacgtaaaca | agaaaatgaa | taataaatac | caatctacag | tggcccacca | 1320 |
| aattgccttc | tttgcggaat | cctactgttc | tgtcttgcac | cacacgcact | ctcacaatgg | 1380 |
| gtggtttggc | tataaagaca | ccactcttac | acacctttc | agcattcacc | acaaccctct | 1440 |
| ctctatattc | cattgccacc | cagttttgaa | tatatttta | ttccttcttt | gtttcttcac | 1500 |
| tttcttccat | acacataacc | atggcccagt | ccaagcacgg | cctgaccaag | gagatgacca | 1560 |
| tgaagtaccg | catggagggc | tgcgtggacg | gccacaagtt | cgtgatcacc | ggcgagggca | 1620 |
| tcggctaccc | cttcaagggc | aagcaggcca | tcaacctgtg | cgtggtggag | ggcggcccct | 1680 |
| tgcccttcgc | cgaggacatc | ttgtccgccg | ccttcatgta | cggcaaccgc | gtgttcaccg | 1740 |
| agtaccccca | ggacatcgtc | gactacttca | agaactcctg | ccccgccggc | tacacctggg | 1800 |
| accgctcctt | cctgttcgag | gacggcgccg | tgtgcatctg | caacgccgac | atcaccgtga | 1860 |
| gcgtggagga | gaactgcatg | taccacgagt | ccaagttcta | cggcgtgaac | ttccccgccg | 1920 |
| acggccccgt | gatgaagaag | atgaccgaca | actgggagcc | ctcctgcgag | aagatcatcc | 1980 |
| ccgtgcccaa | gcagggcatc | ttgaagggcg | acgtgagcat | gtacctgctg | ctgaaggacg | 2040 |
| gtggccgctt | gcgctgccag | ttcgacaccg | tgtacaaggc | caagtccgtg | ccccgcaaga | 2100 |
| tgcccgactg | gcacttcatc | cagcacaagc | tgacccgcga | ggaccgcagc | gacgccaaga | 2160 |

```
accagaagtg gcacctgacc gagcacgcca tcgcctccgg ctccgccttg ccctccggac    2220
tcagatctcg actagagtcg aacctagact tgtccatctt ctggattggc caacttaatt    2280
aatgtatgaa ataaaaggat gcacacatag tgacatgcta atcactataa tgtgggcatc    2340
aaagttgtgt gttatgtgta attactagtt atctgaataa aagagaaaga gatcatccat    2400
atttcttatc ctaaatgaat gtcacgtgtc tttataattc tttgatgaac cagatgcatt    2460
tcattaacca aatccatata catataaata ttaatcatat ataattaata tcaattgggt    2520
tagcaaaaca aatctagtct aggtgtgttt tgcgaattct agtggccggc ccagctgata    2580
tccatcacac tggcggccgc actcgactga attggttccg cgccagcct gcttttttgt    2640
acaaagttgg cattataaaa aagcattgct tatcaatttg ttgcaacgaa caggtcacta    2700
tcagtcaaaa taaaatcatt atttggggcc cgagcttaag taactaacta acaggaagag    2760
tttgtagaaa cgcaaaaagg ccatccgtca ggatggcctt ctgcttagtt tgatgcctgg    2820
cagtttatgg cgggcgtcct gcccgccacc ctccggggcg ttgcttcaca cgttcaaat    2880
ccgctcccgg cggatttgtc ctactcagga gagcgttcac cgacaaacaa cagataaaac    2940
gaaaggccca gtcttccgac tgagcctttc gttttatttg atgcctggca gttccctact    3000
ctcgcttagt agttagacgt ccccgagatc catgctagcg gtaatacggt tatccacaga    3060
atcaggggat aacgcaggaa agaacatgtg agcaaaaggc cagcaaaagg ccaggaaccg    3120
taaaaaggcc gcgttgctgg cgttttttcca taggctccgc ccccctgacg agcatcacaa    3180
aaatcgacgc tcaagtcaga ggtggcgaaa cccgacagga ctataaagat accaggcgtt    3240
tcccctgga agctccctcg tgcgctctcc tgttccgacc ctgccgctta ccggatacct    3300
gtccgccttt ctcccttcgg gaagcgtggc gctttctcat agctcacgct gtaggtatct    3360
cagttcggtg taggtcgttc gctccaagct gggctgtgtg cacgaacccc ccgttcagcc    3420
cgaccgctgc gccttatccg gtaactatcg tcttgagtcc aacccggtaa gacacgactt    3480
atcgccactg gcagcagcca ctggtaacag gattagcaga gcgaggtatg taggcggtgc    3540
tacagagttc ttgaagtggt ggcctaacta cggctacact agaagaacag tatttggtat    3600
ctgcgctctg ctgaagccag ttaccttcgg aaaaagagtt ggtagctctt gatccggcaa    3660
acaaaccacc gctggtagcg gtggtttttt tgtttgcaag cagcagatta cgcgcagaaa    3720
aaaaggatct caagaagatc ctttgatctt ttctacgggg tctgacgctc agtggaacgg    3780
ggcccaatct gaataatgtt acaaccaatt aaccaattct gattagaaaa actcatcgag    3840
catcaaatga aactgcaatt tattcatatc aggattatca ataccatatt tttgaaaaag    3900
ccgtttctgt aatgaaggag aaaactcacc gaggcagttc cataggatgg caagatcctg    3960
gtatcggtct gcgattccga ctcgtccaac atcaatacaa cctattaatt tcccctcgtc    4020
aaaaataagg ttatcaagtg agaaatcacc atgagtgacg actgaatccg gtgagaatgg    4080
caaaagttta tgcatttctt tccagacttg ttcaacaggc cagccattac gctcgtcatc    4140
aaaatcactc gcatcaacca accgttatt cattcgtgat tgcgcctgag cgagacgaaa    4200
tacgcgatcg ctgttaaaag gacaattaca aacaggaatc gaatgcaacc ggcgcaggaa    4260
cactgccagc gcatcaacaa tattttcacc tgaatcagga tattcttcta atacctggaa    4320
tgctgttttt ccggggatcg cagtggtgag taaccatgca tcatcaggag tacggataaa    4380
atgcttgatg gtcggaagag gcataaattc cgtcagccag tttagtctga ccatctcatc    4440
tgtaacatca ttggcaacgc tacctttgcc atgtttcaga aacaactctg gcgcatcggg    4500
```

| | |
|---|---|
| cttcccatac aagcgataga ttgtcgcacc tgattgcccg acattatcgc gagcccattt | 4560 |
| atacccatat aaatcagcat ccatgttgga atttaatcgc ggcctcgacg tttcccgttg | 4620 |
| aatatggctc ataacacccc ttgtattact gtttatgtaa gcagacagtt ttattgttca | 4680 |
| tgatgatata tttttatctt gtgcaatgta acatcagaga ttttgagaca cgggccagag | 4740 |
| ctgcagctgg atggcaaata atgattttat tttgactgat agtgacctgt tcgttgcaac | 4800 |
| aaattgataa gcaatgcttt cttataatgc caactttgta caagaaagct gggtctagat | 4860 |
| atctcga | 4867 |

<210> SEQ ID NO 21
<211> LENGTH: 8482
<212> TYPE: DNA
<213> ORGANISM: Artificial Sequence
<220> FEATURE:
<223> OTHER INFORMATION: plasmid QC478i

<400> SEQUENCE: 21

| | |
|---|---|
| atcgaaccac tttgtacaag aaagctgaac gagaaacgta aaatgatata aatatcaata | 60 |
| tattaaatta gattttgcat aaaaaacaga ctacataata ctgtaaaaca caacatatcc | 120 |
| agtcactatg gtcgacctgc agactggctg tgtataaggg agcctgacat ttatattccc | 180 |
| cagaacatca ggttaatggc gttttttgatg tcattttcgc ggtggctgag atcagccact | 240 |
| tcttccccga taacggagac cggcacactg gccatatcgg tggtcatcat gcgccagctt | 300 |
| tcatccccga tatgcaccac cgggtaaagt tcacggggga ctttatctga cagcagacgt | 360 |
| gcactggcca gggggatcac catccgtcgc ccgggcgtgt caataatatc actctgtaca | 420 |
| tccacaaaca gacgataacg gctctctctt ttataggtgt aaaccttaaa ctgcatttca | 480 |
| ccagcccctg ttctcgtcag caaaagagcc gttcatttca ataaaccggg cgacctcagc | 540 |
| catcccttcc tgattttccg ctttccagcg ttcggcacgc agacgacggg cttcattctg | 600 |
| catggttgtg cttaccagac cggagatatt gacatcatat atgccttgag caactgatag | 660 |
| ctgtcgctgt caactgtcac tgtaatacgc tgcttcatag catacctctt tttgacatac | 720 |
| ttcgggtata catatcagta tatattctta taccgcaaaa atcagcgcgc aaatacgcat | 780 |
| actgttatct ggcttttagt aagccggatc ctctagatta cgccccgcct gccactcatc | 840 |
| gcagtactgt tgtaattcat taagcattct gccgacatgg aagccatcac aaacggcatg | 900 |
| atgaacctga atcgccagcg gcatcagcac cttgtcgcct tgcgtataat atttgcccat | 960 |
| ggtgaaaacg gggcgaaga agttgtccat attggccacg tttaaatcaa actggtgaa | 1020 |
| actcacccag ggattggctg agacgaaaaa catattctca ataaaccctt tagggaaata | 1080 |
| ggccaggttt tcaccgtaac acgccacatc ttgcgaatat atgtgtagaa actgccggaa | 1140 |
| atcgtcgtgg tattcactcc agagcgatga aaacgtttca gtttgctcat ggaaaacggt | 1200 |
| gtaacaaggg tgaacactat cccatatcac cagctcaccg tctttcattg ccatacggaa | 1260 |
| ttccggatga gcattcatca ggcgggcaag aatgtgaata aaggccggat aaaacttgtg | 1320 |
| cttatttttc tttacggtct ttaaaaaggc cgtaatatcc agctgaacgg tctggttata | 1380 |
| ggtacattga gcaactgact gaaatgcctc aaaatgttct ttacgatgcc attgggatat | 1440 |
| atcaacggtg gtatatccag tgatttttt ctccattta gcttccttag ctcctgaaaa | 1500 |
| tctcgacgga tcctaactca aaatccacac attatacgag ccggaagcat aaagtgtaaa | 1560 |
| gcctggggtg cctaatgcgg ccgcacatagt gactggatat ttgtgttttt acagtattat | 1620 |
| gtagtctgtt ttttatgcaa aatctaattt aatatattga tatttatatc attttacgtt | 1680 |

```
tctcgttcag cttttttgta caaacttgtt tgataaacac tagtaacggc cgccagtgtg    1740
ctggaattcg cccttcccaa gctttgctct agatcaaact cacatccaaa cataacatgg    1800
atatcttcct taccaatcat actaattatt ttgggttaaa tattaatcat tatttttaag    1860
atattaatta agaaattaaa agattttta aaaaaatgta taaaattata ttattcatga    1920
tttttcatac atttgatttt gataataaat atattttttt taatttctta aaaaatgttg    1980
caagacactt attagacata gtcttgttct gtttacaaaa gcattcatca tttaatacat    2040
taaaaaatat ttaatactaa cagtagaatc ttcttgtgag tggtgtggga gtaggcaacc    2100
tggcattgaa acgagagaaa gagagtcaga accagaagac aaataaaaag tatgcaacaa    2160
acaaatcaaa atcaaagggc aaaggctggg gttggctcaa ttggttgcta cattcaattt    2220
tcaactcagt caacggttga gattcactct gacttcccca atctaagccg cggatgcaaa    2280
cggttgaatc taacccacaa tccaatctcg ttacttaggg gcttttccgt cattaactca    2340
cccctgccac ccggtttccc tataaattgg aactcaatgc tccctctaa actcgtatcg    2400 cttcagagtt gagaccaaga cacactcgtt catatatctc tctgctcttc tcttctcttc    2460
tacctctcaa ggtacttttc ttctccctct accaaatcct agattccgtg gttcaatttc    2520
ggatcttgca cttctggttt gctttgcctt gcttttcct caactgggtc catctaggat    2580
ccatgtgaaa ctctactctt tctttaatat ctgcggaata cgcgtttgac tttcagatct    2640
agtcgaaatc atttcataat tgcctttctt tcttttagct tatgagaaat aaaatcactt    2700 ttttttatt tcaaaataaa ccttgggcct tgtgctgact gagatggggt ttggtgatta    2760
cagaatttta gcgaattttg taattgtact tgtttgtctg tagttttgtt ttgttttctt    2820
gtttctcata cattccttag gcttcaattt tattcgagta taggtcacaa taggaattca    2880
aactttgagc aggggaatta atcccttcct tcaaatccag tttgtttgta tatatgttta    2940
aaaaatgaaa cttttgcttt aaattctatt ataactttt ttatggctga aattttgca    3000 tgtgtctttg ctctctgttg taaatttact gtttaggtac taactctagg cttgttgtgc    3060 agttttgaa gtataacaac agaagttcct attccgaagt tcctattctc tagaaagtat    3120
aggaacttcc accacacaac acaatggcgg ccaccgcttc cagaaccacc cgattctctt    3180
cttcctcttc acaccccacc ttccccaaac gcattactag atccaccctc cctctctctc    3240
atcaaaccct caccaaaccc aaccacgctc tcaaaatcaa atgttccatc tccaaacccc    3300
ccacggcggc gcccttcacc aaggaagcgc cgaccacgga gcccttcgtg tcacggttcg    3360
cctccggcga acctcgcaag ggcgcggaca tccttgtgga ggcgctggag aggcagggcg    3420
tgacgacggt gttcgcgtac cccggcggtg cgtcgatgga gatccaccag gcgctcacgc    3480
gctccgccgc catccgcaac gtgctcccgc gccacgagca gggcggcgtc ttcgccgccg    3540
aaggctacgc gcgttcctcc ggcctccccg gcgtctgcat tgccacctcc ggccccggcg    3600
ccaccaacct cgtgagcggc ctcgccgacg ctttaatgga cagcgtccca gtcgtcgcca    3660
tcaccggcca ggtcgcccgc cggatgatcg gcaccgacgc cttccaagaa ccccgatcg    3720 tggaggtgag cagatccatc acgaagcaca actacctcat cctcgacgtc gacgacatcc    3780
cccgcgtcgt cgccgaggct ttcttcgtcg ccacctccgg ccgccccggt ccggtcctca    3840
tcgacattcc caaagacgtt cagcagcaac tcgccgtgcc taattgggac gagcccgtta    3900
acctccccgg ttacctcgcc aggctgccca ggccccccgc cgaggcccaa ttggaacaca    3960
ttgtcagact catcatggag gcccaaaagc ccgttctcta cgtcggcggt ggcagtttga    4020
```

```
attccagtgc tgaattgagg cgctttgttg aactcactgg tattcccgtt gctagcactt    4080
taatgggtct tggaactttt cctattggtg atgaatattc ccttcagatg ctgggtatgc    4140
atggtactgt ttatgctaac tatgctgttg acaatagtga tttgttgctt gcctttgggg    4200
taaggtttga tgaccgtgtt actgggaagc ttgaggcttt tgctagtagg gctaagattg    4260
ttcacattga tattgattct gccgagattg ggaagaacaa gcaggcgcac gtgtcggttt    4320
gcgcggattt gaagttggcc ttgaagggaa ttaatatgat tttggaggag aaaggagtgg    4380
agggtaagtt tgatcttgga ggttggagag aagagattaa tgtgcagaaa cacaagtttc    4440
cattgggtta caagacattc caggacgcga tttctccgca gcatgctatc gaggttcttg    4500
atgagttgac taatggagat gctattgtta gtactggggt tgggcagcat caaatgtggg    4560
ctgcgcagtt ttacaagtac aagagaccga ggcagtggtt gacctcaggg ggtcttggag    4620
ccatgggttt tggattgcct gcggctattg gtgctgctgt tgctaaccct ggggctgttg    4680
tggttgacat tgatggggat ggtagtttca tcatgaatgt tcaggagttg gccactataa    4740
gagtggagaa tctcccagtt aagatattgt tgttgaacaa tcagcatttg ggtatggtgg    4800
ttcagttgga ggataggttc tacaagtcca atagagctca cacctatctt ggagatccgt    4860
ctagcgagag cgagatattc ccaaacatgc tcaagtttgc tgatgcttgt gggataccgg    4920
cagcgcgagt gacgaagaag gaagagctta gagcggcaat tcagagaatg ttggacaccc    4980
ctggccccta ccttcttgat gtcattgtgc cccatcagga gcatgtgttg ccgatgattc    5040
ccagtaatgg atccttcaag gatgtgataa ctgagggtga tggtagaacg aggtactgat    5100
tgcctagacc aaatgttcct tgatgcttgt tttgtacaat atatataaga taatgctgtc    5160
ctagttgcag gatttggcct gtggtgagca tcatagtctg tagtagtttt ggtagcaaga    5220
cattttattt tcctttattt taacttacta catgcagtag catctatcta tctctgtagt    5280
ctgatatctc ctgttgtctg tattgtgccg ttggattttt tgctgtagtg agactgaaaa    5340
tgatgtgcta gtaataatat ttctgttaga aatctaagta gagaatcgt tgaagaagtc    5400 aaaagctaat ggaatcaggt tacatattca atgttttct ttttttagcg gttggtagac    5460
gtgtagattc aacttctctt ggagctcacc taggcaatca gtaaaatgca tattccttt    5520 ttaacttgcc atttatttac ttttagtgga aattgtgacc aatttgttca tgtagaacgg    5580
atttggacca ttgcgtccac aaaacgtctc ttttgctcga tcttcacaaa gcgataccga    5640
aatccagaga tagttttcaa aagtcagaaa tggcaaagtt ataaatagta aaacagaata    5700
gatgctgtaa tcgacttcaa taacaagtgg catcacgttt ctagttctag acccatcagc    5760
tgggccggcc cagctgatga tcccggtgaa gttcctattc cgaagttcct attctccaga    5820
aagtatagga acttcactag agcttgcggc cgcgcatgct gacttaatca gctaacgcca    5880
ctcgaggggg ggcccggtac cggcgcgccg ttctatagtg tcacctaaat cgtatgtgta    5940
tgatacataa ggttatgtat taattgtagc cgcgttctaa cgacaatatg tccatatggt    6000
gcactctcag tacaatctgc tctgatgccg catagttaag ccagccccga cacccgccaa    6060
cacccgctga cgcgccctga cgggcttgtc tgctcccggc atccgcttac agacaagctg    6120
tgaccgtctc cggagctgca tgtgtcaga ggttttcacc gtcatcaccg aaacgcgcga    6180
gacgaaaggg cctcgtgata cgcctatttt tataggttaa tgtcatgacc aaaatccctt    6240
aacgtgagtt ttcgttccac tgagcgtcag accccgtaga aaagatcaaa ggatcttctt    6300
gagatccttt tttctgcgc gtaatctgct gcttgcaaac aaaaaaacca ccgctaccag    6360
cggtggtttg tttgccggat caagagctac caactctttt tccgaaggta actggcttca    6420
```

```
gcagagcgca gataccaaat actgtccttc tagtgtagcc gtagttaggc caccacttca    6480
agaactctgt agcaccgcct acatacctcg ctctgctaat cctgttacca gtggctgctg    6540
ccagtggcga taagtcgtgt cttaccgggt tggactcaag acgatagtta ccggataagg    6600
cgcagcggtc gggctgaacg gggggttcgt gcacacagcc cagcttggag cgaacgacct    6660
acaccgaact gagataccta cagcgtgagc attgagaaag cgccacgctt cccgaaggga    6720
gaaaggcgga caggtatccg gtaagcggca gggtcggaac aggagagcgc acgagggagc    6780
ttccaggggg aaacgcctgg tatctttata gtcctgtcgg gtttcgccac ctctgacttg    6840
agcgtcgatt tttgtgatgc tcgtcagggg gcggagcct atggaaaaac gccagcaacg    6900
cggccttttt acgttcctg gccttttgct ggccttttgc tcacatgttc tttcctgcgt    6960
tatcccctga ttctgtggat aaccgtatta ccgcctttga gtgagctgat accgctcgcc    7020
gcagccgaac gaccgagcgc agcgagtcag tgagcgagga agcggaagag cgcccaatac    7080
gcaaaccgcc tctccccgcg cgttggccga ttcattaatg caggttgatc agatctcgat    7140
cccgcgaaat taatacgact cactataggg agaccacaac ggtttccctc tagaaataat    7200
tttgtttaac tttaagaagg agatatacc atggaaaagc ctgaactcac cgcgacgtct    7260
gtcgagaagt ttctgatcga aaagttcgac agcgtctccg acctgatgca gctctcggag    7320
ggcgaagaat ctcgtgcttt cagcttcgat gtaggagggc gtggatatgt cctgcgggta    7380
aatagctgcg ccgatggttt ctacaaagat cgttatgttt atcggcactt tgcatcggcc    7440
gcgctcccga ttccggaagt gcttgacatt ggggaattca gcgagagcct gacctattgc    7500
atctcccgcc gtgcacaggg tgtcacgttg caagacctgc ctgaaaccga actgcccgct    7560
gttctgcagc cggtcgcgga ggctatggat gcgatcgctg cggccgatct tagccagacg    7620
agcgggttcg gcccattcgg accgcaagga atcggtcaat acactacatg gcgtgatttc    7680
atatgcgcga ttgctgatcc ccatgtgtat cactggcaaa ctgtgatgga cgacaccgtc    7740
agtgcgtccg tcgcgcaggc tctcgatgag ctgatgcttt gggccgagga ctgccccgaa    7800
gtccggcacc tcgtgcacgc ggatttcggc tccaacaatg tcctgacgga caatggccgc    7860
ataacagcgg tcattgactg gagcgaggcg atgttcgggg attcccaata cgaggtcgcc    7920
aacatcttct tctggaggcc gtggttggct tgtatggagc agcagacgcg ctacttcgag    7980
cggaggcatc cggagcttgc aggatcgccg cggctccggg cgtatatgct ccgcattggt    8040
cttgaccaac tctatcagag cttggttgac ggcaatttcg atgatgcagc ttgggcgcag    8100
ggtcgatgcg acgcaatcgt ccgatccgga gccgggactg tcgggcgtac acaaatcgcc    8160
cgcagaagcg cggccgtctg gaccgatggc tgtgtagaag tactcgccga tagtggaaac    8220
cgacgcccca gcactcgtcc gagggcaaag gaatagtgag gtacagcttg atcgatccg    8280 gctgctaaca aagcccgaaa ggaagctgag ttggctgctg ccaccgctga gcaataacta    8340
gcataacccc ttggggcctc taaacgggtc ttgaggggtt ttttgctgaa aggaggaact    8400
atatccggat gctcgggcgc gccggtaccc gggtaccgag ctcactagac gcggtgaaat    8460
tacctaatta acaccggtgt tt                                              8482
```

<210> SEQ ID NO 22
<211> LENGTH: 9466
<212> TYPE: DNA
<213> ORGANISM: Artificial Sequence
<220> FEATURE:
<223> OTHER INFORMATION: plasmid QC645

```
<400> SEQUENCE: 22
cccgggagaa aattacctaa gtgtcatgtg caagtacaat tatgaattca attttttaaac      60
atgtctatat gaaaaaatat ttattaagac aagtttgtct cttaaatata tcttaatacc     120
ttaaaagatt aattattagt tctcgatcag aatatcctaa gttaaaaata aataaataaa     180
taaaacaaca aaaattgaag caaacaataa ccattaaata aagtttaatc tgtaacgtgg     240
attacaagtg gtgaaaattt ataaatctgg attcgacttt ttcttatgcc acttagtgga     300
caactttctt caaagaattc tcgtattgct ctggcgcagt tgagtaagtc tatgtttggt     360
ttacagatgg ggagttttaa actcaatttg aagagaaaaa tgagtttaac attatgttta     420
atttctctct aaaaatatgt ttaaagttaa aatttagcct gaaaacttac ttagggagac     480
acaactatta gaatatttt gcaaactgca atccaaattt tgagtttaaa attttgcctc     540
aacactcaat ttgggaaaaa caactattag gatattcttg caaatttagt ttgtaaactt     600
aagtttaact aaaacttaaa tttgaaaact gtaatccaaa catgtccttg tattcctgtg     660
aattgaaggt gcctctccca ccttttacca ataaaaataa aaagttgaat ctattaacgc     720
tacattcgtt gttatccatt aggcgcactc caaagctttt atattcgat ctaagcatta     780
tctctcaaaa gttgtaccgg aaaaacgttg ccatcgtacg tgagaagaaa gattttcacg     840
taaattactt tttcgttaga ttatatttta gtccttatat ttctattatt tttaaataa      900
aaacttacaa tcctcacttt atatatatta aaataggtgt tttaaaaata ataattttag     960
aaactattct tcaatgacaa catctttaag aattttctcc aacaaaaatg ttttttaggta   1020
ttttttctaat ctattatctc ttttaatcca tcactctcat atacacctt aaattattaa    1080
agtctattaa aaaataaata aaaatataag aagctatcta gagaataatt tatcctaaat    1140
tcttttttata cgatacatta tatgtggagc acattaggat aaaggaaaaa aagaaaacgt    1200
tagctaggca aattaaaata ataacaaaaa tcttgataaa acgtttaatt tgaaccaaga    1260
atgaaaatca aacgtaaaca agaaaatgaa taataaatac caatctacag tggcccacca    1320
aattgccttc tttgcggaat cctactgttc tgtcttgcac cacacgcact ctcacaatgg    1380
gtggtttggc tataaagaca ccactcttac acaccctttc agcattcacc acaaccctct    1440
ctctatattc cattgccacc cagttttgaa tatattttta ttccttcttt gtttcttcac    1500
tttcttccat acacataacc atggcccagt ccaagcacgg cctgaccaag gagatgacca    1560
tgaagtaccg catggagggc tgcgtggacg gccacaagtt cgtgatcacc ggcgagggca    1620
tcggctaccc cttcaagggc aagcaggcca tcaacctgtg cgtggtggag ggcggccccct    1680
tgcccttcgc cgaggacatc ttgtccgccg ccttcatgta cggcaaccgc gtgttcaccg    1740
agtaccccca ggacatcgtc gactacttca agaactcctg ccccgccggc tacacctggg    1800
accgctcctt cctgttcgag gacggcgccg tgtgcatctg caacgccgac atcaccgtga    1860
gcgtggagga gaactgcatg taccacgagt ccaagttcta cggcgtgaac ttccccgccg    1920
acggccccgt gatgaagaag atgaccgaca ctgggagcc ctcctgcgag aagatcatcc     1980
ccgtgcccaa gcagggcatc ttgaagggcg acgtgagcat gtacctgctg ctgaaggacg    2040
gtggccgctt cgcgctgcag ttcgacaccg tgtacaaggc caagtccgtg ccccgcaaga    2100
tgcccgactg gcacttcatc cagcacaagc tgacccgcga ggaccgcagc gacgccaaga    2160
accagaagtg gcacctgacc gagcacgcca tcgcctccgg ctccgccttg ccctccggac    2220
tcagatctcg actagagtcg aacctagact tgtccatctt ctggattggc caacttaatt    2280
aatgtatgaa ataaaaggat gcacacatag tgacatgcta atcactataa tgtgggcatc    2340
```

```
aaagttgtgt gttatgtgta attactagtt atctgaataa aagagaaaga gatcatccat    2400
atttcttatc ctaaatgaat gtcacgtgtc tttataattc tttgatgaac cagatgcatt    2460
tcattaacca aatccatata catataaata ttaatcatat ataattaata tcaattgggt    2520
tagcaaaaca aatctagtct aggtgtgttt tgcgaattct agtggccggc ccagctgata    2580
tccatcacac tggcggccgc actcgactga attggttccg gcgccagcct gcttttttgt    2640
acaaacttgt ttgataaaca ctagtaacgg ccgccagtgt gctggaattc gcccttccca    2700
agctttgctc tagatcaaac tcacatccaa acataacatg gatatcttcc ttaccaatca    2760
tactaattat tttgggttaa atattaatca ttatttttaa gatattaatt aagaaattaa    2820 aagattttt aaaaaaatgt ataaaattat attattcatg attttttcata catttgattt    2880 tgataataaa tatatttttt ttaatttctt aaaaaatgtt gcaagacact tattagacat    2940
agtcttgttc tgtttacaaa agcattcatc atttaataca ttaaaaaata tttaatacta    3000
acagtagaat cttcttgtga gtggtgtggg agtaggcaac ctggcattga aacgagagaa    3060
agagagtcag aaccagaaga caaataaaaa gtatgcaaca aacaaatcaa aatcaaaggg    3120
caaaggctgg ggttggctca attggttgct acattcaatt ttcaactcag tcaacggttg    3180
agattcactc tgacttcccc aatctaagcc gcggatgcaa acggttgaat ctaacccaca    3240
atccaatctc gttacttagg ggcttttccg tcattaactc accctgcca cccggtttcc    3300 ctataaattg gaactcaatg ctcccctcta aactcgtatc gcttcagagt tgagaccaag    3360
acacactcgt tcatatatct ctctgctctt ctcttctctt ctacctctca aggtacttt    3420 cttctccctc taccaaatcc tagattccgt ggttcaattt cggatcttgc acttctggtt    3480
tgctttgcct tgcttttttcc tcaactgggt ccatctagga tccatgtgaa actctactct    3540
ttctttaata tctgcggaat acgcgtttga cttttcagatc tagtcgaaat catttcataa    3600
ttgcctttct ttcttttagc ttatgagaaa taaaatcact tttttttat ttcaaaataa    3660 accttgggcc ttgtgctgac tgagatgggg tttggtgatt acagaattt agcgaatttt    3720 gtaattgtac ttgttttgtct gtagtttgt tttgttttct tgtttctcat acattcctta    3780
ggcttcaatt ttattcgagt ataggtcaca ataggaattc aaactttgag cagggaatt    3840 aatcccttcc ttcaaatcca gtttgttgt atatatgttt aaaaaatgaa acttttgctt    3900
taaattctat tataacttt tttatggctg aaattttgc atgtgtcttt gctctctgtt    3960
gtaaatttac tgtttaggta ctaactctag gcttgttgtg cagttttga agtataacaa    4020 cagaagttcc tattccgaag ttcctattct ctagaaagta taggaacttc caccacacaa    4080
cacaatggcg gccaccgctt ccagaaccac ccgattctct tcttcctctt cacacccccac    4140 cttccccaaa cgcattacta gatccaccct ccctctctct catcaaaccc tcaccaaacc    4200
caaccacgct ctcaaaatca aatgttccat ctccaaaccc cccacggcgg cgcccttcac    4260
caaggaagcg ccgaccacgg agcccttcgt gtcacggttc gcctccggcg aacctcgcaa    4320
gggcgcggac atccttgtgg aggcgctgga gaggcagggc gtgacgacgg tgttcgcgta    4380
ccccggcggt gcgtcgatgg agatccacca ggcgctcacg cgctccgccg ccatccgcaa    4440
cgtgctcccg cgccacgagc agggcggcgt cttcgccgcc gaaggctacg cgcgttcctc    4500
cggcctcccc ggcgtctgca ttgccacctc cggccccggc gccaccaacc tcgtgagcgg    4560
cctcgccgac gctttaatgg acagcgtccc agtcgtcgcc atcaccggcc aggtcgcccg    4620
ccggatgatc ggcaccgacg ccttccaaga aaccccgatc gtggaggtga gcagatccat    4680
```

```
cacgaagcac aactacctca tcctcgacgt cgacgacatc ccccgcgtcg tcgccgaggc    4740
tttcttcgtc gccacctccg gccgccccgg tccggtcctc atcgacattc ccaaagacgt    4800
tcagcagcaa ctcgccgtgc ctaattggga cgagcccgtt aacctccccg gttacctcgc    4860
caggctgccc aggcccccg ccgaggccca attggaacac attgtcagac tcatcatgga    4920
ggcccaaaag cccgttctct acgtcggcgg tggcagtttg aattccagtg ctgaattgag    4980
gcgctttgtt gaactcactg gtattcccgt tgctagcact ttaatgggtc ttggaacttt    5040
tcctattggt gatgaatatt cccttcagat gctgggtatg catggtactg tttatgctaa    5100
ctatgctgtt gacaatagtg atttgttgct tgcctttggg gtaaggtttg atgaccgtgt    5160
tactgggaag cttgaggctt tgctagtag ggctaagatt gttcacattg atattgattc    5220
tgccgagatt gggaagaaca agcaggcgca cgtgtcggtt tgcgcggatt tgaagttggc    5280
cttgaaggga attaatatga ttttggagga gaaaggagtg gagggtaagt ttgatcttgg    5340
aggttggaga gaagagatta atgtgcagaa acacaagttt ccattgggtt acaagacatt    5400
ccaggacgcg atttctccgc agcatgctat cgaggttctt gatgagttga ctaatggaga    5460
tgctattgtt agtactgggg ttgggcagca tcaaatgtgg gctgcgcagt tttacaagta    5520
caagagaccg aggcagtggt tgacctcagg gggtcttgga gccatgggtt ttggattgcc    5580
tgcggctatt ggtgctgctg ttgctaaccc tggggctgtt gtggttgaca ttgatgggga    5640
tggtagtttc atcatgaatg ttcaggagtt ggccactata agagtggaga atctcccagt    5700
taagatattg ttgttgaaca atcagcattt gggtatggtg gttcagttgg aggataggtt    5760
ctacaagtcc aatagagctc acacctatct tggagatccg tctagcgaga gcgagatatt    5820
cccaaacatg ctcaagtttg ctgatgcttg tgggataccg gcagcgcgag tgacgaagaa    5880
ggaagagctt agagcggcaa ttcagagaat gttggacacc cctggccccct accttcttga    5940 tgtcattgtg ccccatcagg agcatgtgtt gccgatgatt cccagtaatg gatccttcaa    6000
ggatgtgata actgagggtg atggtagaac gaggtactga ttgcctagac caaatgttcc    6060
ttgatgcttg ttttgtacaa tatatataag ataatgctgt cctagttgca ggatttggcc    6120
tgtggtgagc atcatagtct gtagtagttt tggtagcaag acatttattt ttcctttat    6180 ttaacttact acatgcagta gcatctatct atctctgtag tctgatatct cctgttgtct    6240
gtattgtgcc gttggatttt tgctgtagt gagactgaaa atgatgtgct agtaataata    6300
tttctgttag aaatctaagt agagaatctg ttgaagaagt caaaagctaa tggaatcagg    6360
ttacatattc aatgttttc tttttttagc ggttggtaga cgtgtagatt caacttctct    6420
tggagctcac ctaggcaatc agtaaaatgc atattccttt tttaacttgc catttattta    6480
cttttagtgg aaattgtgac caatttgttc atgtagaacg gatttggacc attgcgtcca    6540
caaaacgtct cttttgctcg atcttcacaa agcgataccg aaatccagag atagttttca    6600
aaagtcagaa atggcaaagt tataaatagt aaaacagaat agatgctgta atcgacttca    6660
ataacaagtg gcatcacgtt tctagttcta gacccatcag ctgggccggc ccagctgatg    6720
atcccggtga agttcctatt ccgaagttcc tattctccag aaagtatagg aacttcacta    6780
gagcttgcgg ccgcgcatgc tgacttaatc agctaacgcc actcgagggg gggcccggta    6840
ccggcgcgcc gttctatagt gtcacctaaa tcgtatgtgt atgatacata aggttatgta    6900
ttaattgtag ccgcgttcta acgacaatat gtccatatgg tgcactctca gtacaatctg    6960
ctctgatgcc gcatagttaa gccagccccg acacccgcca cacccgctg acgcgccctg    7020 acgggcttgt ctgctcccgg catccgctta cagacaagct gtgaccgtct ccgggagctg    7080
```

```
catgtgtcag aggttttcac cgtcatcacc gaaacgcgcg agacgaaagg gcctcgtgat   7140
acgcctattt ttataggtta atgtcatgac caaaatccct aacgtgagt tttcgttcca    7200
ctgagcgtca gacccccgtag aaaagatcaa aggatcttct tgagatcctt tttttctgcg  7260
cgtaatctgc tgcttgcaaa caaaaaaacc accgctacca gcggtggttt gtttgccgga   7320
tcaagagcta ccaactcttt ttccgaaggt aactggcttc agcagagcgc agataccaaa   7380
tactgtcctt ctagtgtagc cgtagttagg ccaccacttc aagaactctg tagcaccgcc   7440
tacatacctc gctctgctaa tcctgttacc agtggctgct gccagtggcg ataagtcgtg   7500
tcttaccggg ttggactcaa gacgatagtt accggataag gcgcagcggt cgggctgaac   7560
gggggggttcg tgcacacagc ccagcttgga gcgaacgacc tacaccgaac tgagatacct   7620
acagcgtgag cattgagaaa gcgccacgct tcccgaaggg agaaaggcgg acaggtatcc   7680
ggtaagcggc agggtcggaa caggagagcg cacgagggag cttccagggg gaaacgcctg   7740
gtatctttat agtcctgtcg ggtttcgcca cctctgactt gagcgtcgat ttttgtgatg   7800
ctcgtcaggg gggcggagcc tatggaaaaa cgccagcaac gcggcctttt tacggttcct   7860
ggccttttgc tggccttttg ctcacatgtt ctttcctgcg ttatccccctg attctgtgga  7920
taaccgtatt accgcctttg agtgagctga taccgctcgc cgcagccgaa cgaccgagcg   7980
cagcgagtca gtgagcgagg aagcggaaga gcgcccaata cgcaaaccgc ctctccccgc   8040
gcgttggccg attcattaat gcaggttgat cagatctcga tcccgcgaaa ttaatacgac   8100
tcactatagg gagaccacaa cggtttccct ctagaaataa ttttgtttaa ctttaagaag   8160
gagatatacc catggaaaag cctgaactca ccgcgacgtc tgtcgagaag tttctgatcg   8220
aaaagttcga cagcgtctcc gacctgatgc agctctcgga gggcgaagaa tctcgtgctt   8280
tcagcttcga tgtaggaggg cgtggatatg tcctgcgggt aaatagctgc gccgatggtt   8340
tctacaaaga tcgttatgtt tatcggcact ttgcatcggc cgcgctcccg attccggaag   8400
tgcttgacat tggggaattc agcgagagcc tgacctattg catctcccgc cgtgcacagg   8460
gtgtcacgtt gcaagacctg cctgaaaccg aactgcccgc tgttctgcag ccggtcgcgg   8520
aggctatgga tgcgatcgct gcggccgatc ttagccagac gagcgggttc ggcccattcg   8580
gaccgcaagg aatcggtcaa tacactacat ggcgtgattt catatgcgcg attgctgatc   8640
cccatgtgta tcactggcaa actgtgatgg acgacaccgt cagtgcgtcc gtcgcgcagg   8700
ctctcgatga gctgatgctt tgggccgagg actgccccga agtccggcac ctcgtgcacg   8760
cggatttcgg ctccaacaat gtcctgacgg acaatggccg cataacagcg gtcattgact   8820
ggagcgaggc gatgttcggg gattcccaat acgaggtcgc caacatcttc ttctggaggc   8880
cgtggttggc ttgtatggag cagcagacgc gctacttcga gcggaggcat ccggagcttg   8940
caggatcgcc gcggctccgg gcgtatatgc tccgcattgg tcttgaccaa ctctatcaga   9000
gcttggttga cggcaatttc gatgatgcag cttgggcgca gggtcgatgc gacgcaatcg   9060
tccgatccgg agccgggact gtcgggcgta cacaaatcgc ccgcagaagc gcggccgtct   9120
ggaccgatgg ctgtgtagaa gtactcgccg atagtggaaa ccgacgcccc agcactcgtc   9180
cgagggcaaa ggaatagtga ggtacagctt ggatcgatcc ggctgctaac aaagcccgaa   9240
aggaagctga gttggctgct gccaccgctg agcaataact agcataaccc cttggggcct   9300
ctaaacgggt cttgaggggt ttttgctgaa aggaggaac tatatccgga tgctcgggcg    9360
cgccggtacc cgggtaccga gctcactaga cgcggtgaaa ttacctaatt aacaccggtg   9420
```

-continued

| tttatcgaac cactttgtac aagaaagctg gtctagata tctcga | 9466 |

<210> SEQ ID NO 23
<211> LENGTH: 4333
<212> TYPE: DNA
<213> ORGANISM: Artificial Sequence
<220> FEATURE:
<223> OTHER INFORMATION: plasmid QC533-1

<400> SEQUENCE: 23

| gggagaaaat tacctaagtg tcatgtgcaa gtacaattat gaattcaatt tttaaacatg | 60 |
| tctatatgaa aaatatttta ttaagacaag tttgtctctt aaatatatct taataccttg | 120 |
| aaagattaat tattagttct cgatcagaat atcctaagtt aaaaataaat aaataaataa | 180 |
| aacaacaaaa attgaagcaa acaataacca ttaaataaag tttaatctgt aacgtggatt | 240 |
| acaagtggtg aaaatttata aatctggatt cgactttttc ttatgccact tagtggacaa | 300 |
| cttcttcaa agaattctcg tattgctctg gcgcagttga gtaagtctat gtttggttta | 360 |
| cagatgggga gttttaaact caatttgaag agaaaaatga gttaacatt atgtttaatt | 420 |
| tctctctaaa aatatgttta aagttaaaat ttagcctgaa aacttactta gggagacaca | 480 |
| actattagaa tattttttgca aactgcaatc caaattttga gttaaaaatt ttgcctcaac | 540 |
| actcaatttg ggaaaaacaa ctattaggat attcttgcaa atttagtttg taaacttaag | 600 |
| tttaacttaa acttaaattt ggaaactgta atccaaacat gtccttgtat tcctgtgaat | 660 |
| tgaaggtgcc tctcccacct tttaccaata aaaataaaaa gttgaatcta ttaacgctac | 720 |
| attcgttgtt atccattagg cgcactccaa agcttttata tttcgatcta agcattatct | 780 |
| ctcaaaagtt gtaccggaaa aacgttgcca tcgtacgtga agaaaagat tttcacgtaa | 840 |
| attactttt cgttagatta tattttagtc cttatatttc tattattttt taaataaaaa | 900 |
| cttacaatcc tcactttata tatattaaaa taggtgtttt aaaaataata attttagaaa | 960 |
| ctattcttca atgacaacat cttaagaat tttctccaac aaaaatgttt ttaggtattt | 1020 |
| ttctaatcta ttatctcttt taatccatca ctctcatata caccttaaa ttattaaagt | 1080 |
| ctattaaaaa ataaataaaa atataagaag ctatctagag aataatttat cctaaattct | 1140 |
| ttttatacga tacattatat gtggagcaca ttaggataaa ggaaaaaag aaaacgttag | 1200 |
| ctaggcaaat taaataata acaaaaatct tgataaaacg tttaatttga accagaatg | 1260 |
| aaaatcaaac gtaaacaaga aaatgaataa taaataccaa tctacagtgg cccaccaaat | 1320 |
| tgccttcttt gcggaatcct actgttctgt cttgcaccac acgcactctc acaatgggtg | 1380 |
| gtttggctat aaagacacca ctcttacaca ccctttcagc attcaccaca accctctctc | 1440 |
| tatattccat tgccacccag ttttgaatat attttttattc cttctttgtt tcttcacttt | 1500 |
| cttccataca cataacaagg gcgaattcga cccagctttc ttgtacaaag ttggcattat | 1560 |
| aaaaaataat tgctcatcaa tttgttgcaa cgaacaggtc actatcagtc aaaataaaat | 1620 |
| cattatttgc catccagctg atatcccta tagtgagtcg tattacatgg tcatagctgt | 1680 |
| ttcctggcag ctctggcccg tgtctcaaaa tctctgatgt tacattgcac aagataaaaa | 1740 |
| tatatcatca tgcctcctct agaccagcca ggacagaaat gcctcgactt cgctgctgcc | 1800 |
| caaggttgcc gggtgacgca caccgtggaa acggatgaag gcacgaaccc agtggacata | 1860 |
| agcctgttcg gttcgtaagc tgtaatgcaa gtagcgtatg cgctcacgca actggtccag | 1920 |
| aaccttgacc gaacgcagcg gtggtaacgg cgcagtggcg gttttcatgg cttgttatga | 1980 |
| ctgtttttttt ggggtacagt ctatgcctcg ggcatccaag cagcaagcgc gttacgccgt | 2040 |

```
gggtcgatgt tgatgttat ggagcagcaa cgatgttacg cagcagggca gtcgccctaa    2100
aacaaagtta aacatcatga gggaagcggt gatcgccgaa gtatcgactc aactatcaga    2160
ggtagttggc gtcatcgagc gccatctcga accgacgttg ctggccgtac atttgtacgg    2220
ctccgcagtg gatggcggcc tgaagccaca cagtgatatt gatttgctgg ttacggtgac    2280
cgtaaggctt gatgaaacaa cgcggcgagc tttgatcaac gacctttggg aaacttcggc    2340
ttcccctgga gagagcgaga ttctccgcgc tgtagaagtc accattgttg tgcacgacga    2400
catcattccg tggcgttatc cagctaagcg cgaactgcaa tttggagaat ggcagcgcaa    2460
tgacattctt gcaggtatct tcgagccagc cacgatcgac attgatctgg ctatcttgct    2520
gacaaaagca agagaacata gcgttgcctt ggtaggtcca gcggcggagg aactctttga    2580
tccggttcct gaacaggatc tatttgaggc gctaaatgaa accttaacgc tatgaactc     2640 gccgcccgac tgggctggcg atgagcgaaa tgtagtgctt acgttgtccc gcatttggta    2700
cagcgcagta accggcaaaa tcgcgccgaa ggatgtcgct gccgactggg caatggagcg    2760
cctgccggcc cagtatcagc ccgtcatact tgaagctaga caggcttatc ttggacaaga    2820
agaagatcgc ttggcctcgc gcgcagatca gttggaagaa tttgtccact acgtgaaagg    2880
cgagatcacc aaggtagtcg gcaaataacc ctcgagccac ccatgaccaa atcccttaa    2940 cgtgagttac gcgtcgttcc actgagcgtc agaccccgta gaaaagatca aaggatcttc    3000
ttgagatcct ttttttctgc gcgtaatctg ctgcttgcaa acaaaaaaac caccgctacc    3060
agcggtggtt tgtttgccgg atcaagagct accaactctt tttccgaagg taactggctt    3120
cagcagagcg cagataccaa atactgtcct tctagtgtag ccgtagttag gccaccactt    3180
caagaactct gtagcaccgc ctacatacct cgctctgcta atcctgttac cagtggctgc    3240
tgccagtggc gataagtcgt gtcttaccgg gttggactca agacgatagt taccggataa    3300
ggcgcagcgg tcgggctgaa cggggggttc gtgcacacag cccagcttgg agcgaacgac    3360
ctacaccgaa ctgagatacc tacagcgtga gcattgagaa agcgccacgc ttcccgaagg    3420
gagaaaggcg gacaggtatc cggtaagcgg cagggtcgga acaggagagc gcacgaggga    3480
gcttccaggg ggaaacgcct ggtatcttta tagtcctgtc gggtttcgcc acctctgact    3540
tgagcgtcga tttttgtgat gctcgtcagg gggcggagc ctatggaaaa acgccagcaa     3600
cgcggccttt ttacggttcc tggccttttg ctggccttt gctcacatgt tctttcctgc     3660
gttatcccct gattctgtgg ataaccgtat taccgccttt gagtgagctg ataccgctcg    3720
ccgcagccga acgaccgagc gcagcgagtc agtgagcgag gaagcggaag agcgcccaat    3780
acgcaaaccg cctctccccg cgcgttggcc gattcattaa tgcagctggc acgacaggtt    3840
tcccgactgg aaagcgggca gtgagcgcaa cgcaattaat gcgcgtaccg ctagccagga    3900
agagtttgta gaaacgcaaa aaggccatcc gtcaggatgg ccttctgctt agtttgatgc    3960
ctggcagttt atgcgggcg tcctgcccgc caccctccgg gccgttgctt cacaacgttc      4020
aaatccgctc ccggcggatt tgtcctactc aggagagcgt tcaccgacaa caacagata    4080 aaacgaaagg cccagtcttc cgactgagcc tttcgtttta tttgatgcct ggcagttccc    4140
tactctcgcg ttaacgctag catggatgtt ttcccagtca cgacgttgta aaacgacggc    4200
cagtcttaag ctcgggcccc aaataatgat tttattttga ctgatagtga cctgttcgtt    4260
gcaacaaatt gatgagcaat gcttttttat aatgccaact ttgtacaaaa aagcaggctc    4320
cgaattcgcc ctt                                                       4333
```

<210> SEQ ID NO 24
<211> LENGTH: 5286
<212> TYPE: DNA
<213> ORGANISM: Artificial Sequence
<220> FEATURE:
<223> OTHER INFORMATION: plasmid QC330

<400> SEQUENCE: 24

| | | | | | |
|---|---|---|---|---|---|
| atcaacaagt | ttgtacaaaa | aagctgaacg | agaaacgtaa | aatgatataa | atatcaatat | 60 |
| attaaattag | attttgcata | aaaaacagac | tacataatac | tgtaaaacac | aacatatcca | 120 |
| gtcatattgg | cggccgcatt | aggcacccca | ggctttacac | tttatgcttc | cggctcgtat | 180 |
| aatgtgtgga | ttttgagtta | ggatccgtcg | agattttcag | gagctaagga | agctaaaatg | 240 |
| gagaaaaaaa | tcactggata | taccaccgtt | gatatatccc | aatggcatcg | taaagaacat | 300 |
| tttgaggcat | ttcagtcagt | tgctcaatgt | acctataacc | agaccgttca | gctggatatt | 360 |
| acggcctttt | taaagaccgt | aaagaaaaat | aagcacaagt | tttatccggc | ctttattcac | 420 |
| attcttgccc | gcctgatgaa | tgctcatccg | gaattccgta | tggcaatgaa | agacggtgag | 480 |
| ctggtgatat | gggatagtgt | tcacccttgt | tacaccgttt | tccatgagca | aactgaaacg | 540 |
| ttttcatcgc | tctggagtga | ataccacgac | gatttccggc | agtttctaca | catatattcg | 600 |
| caagatgtgg | cgtgttacgg | tgaaaacctg | gcctatttcc | ctaaagggtt | tattgagaat | 660 |
| atgtttttcg | tctcagccaa | tccctgggtg | agtttcacca | gttttgattt | aaacgtggcc | 720 |
| aatatggaca | acttcttcgc | ccccgttttc | accatgggca | atattatac | gcaaggcgac | 780 |
| aaggtgctga | tgccgctggc | gattcaggtt | catcatgccg | tttgtgatgg | cttccatgtc | 840 |
| ggcagaatgc | ttaatgaatt | acaacagtac | tgcgatgagt | ggcagggcgg | ggcgtaaaga | 900 |
| tctggatccg | gcttactaaa | agccagataa | cagtatgcgt | atttgcgcgc | tgatttttgc | 960 |
| ggtataagaa | tatatactga | tatgtatacc | cgaagtatgt | caaaaagagg | tatgctatga | 1020 |
| agcagcgtat | tacagtgaca | gttgacagcg | acagctatca | gttgctcaag | gcatatatga | 1080 |
| tgtcaatatc | tccggtctgg | taagcacaac | catgcagaat | gaagcccgtc | gtctgcgtgc | 1140 |
| cgaacgctgg | aaagcggaaa | atcaggaagg | gatggctgag | gtcgcccggt | ttattgaaat | 1200 |
| gaacggctct | tttgctgacg | agaacagggg | ctggtgaaat | gcagtttaag | gtttacacct | 1260 |
| ataaaagaga | gagccgttat | cgtctgtttg | tggatgtaca | gagtgatatt | attgacacgc | 1320 |
| ccgggcgacg | gatggtgatc | cccctggcca | gtgcacgtct | gctgtcagat | aaagtctccc | 1380 |
| gtgaacttta | cccggtggtg | catatcgggg | atgaaagctg | gcgcatgatg | accaccgata | 1440 |
| tggccagtgt | gccggtctcc | gttatcgggg | aagaagtggc | tgatctcagc | caccgcgaaa | 1500 |
| atgacatcaa | aaacgccatt | aacctgatgt | tctggggaat | ataaatgtca | ggctccctta | 1560 |
| tacacagcca | gtctgcaggt | cgaccatagt | gactggatat | gttgtgtttt | acagtattat | 1620 |
| gtagtctgtt | ttttatgcaa | aatctaattt | aatatattga | tatttatatc | attttacgtt | 1680 |
| tctcgttcag | ctttcttgta | caaagtggtt | gatgggatcc | atggcccaca | gcaagcacgg | 1740 |
| cctgaaggag | gagatgacca | tgaagtacca | catggagggc | tgcgtgaacg | gccacaagtt | 1800 |
| cgtgatcacc | ggcgagggca | tcggctaccc | cttcaagggc | aagcagacca | tcaacctgtg | 1860 |
| cgtgatcgag | ggcggccccc | tgcccttcag | cgaggacatc | ctgagcgccg | gcttcaagta | 1920 |
| cggcgaccgg | atcttcaccg | agtaccccca | ggacatcgtg | gactacttca | agaacagctg | 1980 |
| ccccgccggc | tacacctggg | gccggagctt | cctgttcgag | gacggcgccg | tgtgcatctg | 2040 |
| taacgtggac | atcaccgtga | gcgtgaagga | gaactgcatc | taccacaaga | gcatcttcaa | 2100 |

```
cggcgtgaac ttccccgccg acggcccgt gatgaagaag atgaccacca actgggaggc    2160
cagctgcgag aagatcatgc ccgtgcctaa gcagggcatc ctgaagggcg acgtgagcat    2220
gtacctgctg ctgaaggacg gcggccggta ccggtgccag ttcgacaccg tgtacaaggc    2280
caagagcgtg cccagcaaga tgcccgagtg gcacttcatc cagcacaagc tgctgcggga    2340
ggaccggagc gacgccaaga accagaagtg gcagctgacc gagcacgcca tcgccttccc    2400
cagcgccctg gcctgagagc tcgaatttcc ccgatcgttc aaacatttgg caataaagtt    2460
tcttaagatt gaatcctgtt gccggtcttg cgatgattat catataattt ctgttgaatt    2520
acgttaagca tgtaataatt aacatgtaat gcatgacgtt atttatgaga tgggttttta    2580
tgattagagt cccgcaatta tacatttaat acgcgataga aaacaaaata tagcgcgcaa    2640
actaggataa attatcgcgc gcggtgtcat ctatgttact agatcgggaa ttctagtggc    2700
cggcccagct gatatccatc acactggcgg ccgctcgagt tctatagtgt cacctaaatc    2760
gtatgtgtat gatacataag gttatgtatt aattgtagcc gcgttctaac gacaatatgt    2820
ccatatggtg cactctcagt acaatctgct ctgatgccgc atagttaagc cagccccgac    2880
acccgccaac acccgctgac gcgccctgac gggcttgtct gctcccggca tccgcttaca    2940
gacaagctgt gaccgtctcc gggagctgca tgtgtcagag gttttcaccg tcatcaccga    3000
aacgcgcgag acgaaagggc ctcgtgatac gcctattttt ataggttaat gtcatgacca    3060
aaatcccta acgtgagttt cgttccact gagcgtcaga ccccgtagaa aagatcaaag    3120
gatcttcttg agatcctttt tttctgcgcg taatctgctg cttgcaaaca aaaaaaccac    3180
cgctaccagc ggtggtttgt ttgccggatc aagagctacc aactctttt ccgaaggtaa    3240
ctggcttcag cagagcgcag ataccaaata ctgtccttct agtgtagccg tagttaggcc    3300
accacttcaa gaactctgta gcaccgccta catacctcgc tctgctaatc ctgttaccag    3360
tggctgctgc cagtggcgat aagtcgtgtc ttaccgggtt ggactcaaga cgatagttac    3420
cggataaggc gcagcggtcg ggctgaacgg ggggttcgtg cacacagccc agcttggagc    3480
gaacgaccta caccgaactg agatacctac agcgtgagca ttgagaaagc gccacgcttc    3540
ccgaagggag aaaggcggac aggtatccgg taagcggcag ggtcggaaca ggagagcgca    3600
cgagggagct tccaggggga aacgcctggt atctttatag tcctgtcggg tttcgccacc    3660
tctgacttga gcgtcgattt tgtgatgct cgtcaggggg gcggagccta tggaaaaacg    3720
ccagcaacgc ggccttttta cggttcctgg ccttttgctg gccttttgct cacatgttct    3780
ttcctgcgtt atcccctgat tctgtggata accgtattac cgcctttgag tgagctgata    3840
ccgctcgccg cagccgaacg accgagcgca gcgagtcagt gagcgaggaa gcggaagagc    3900
gcccaatacg caaaccgcct ctccccgcgc gttggccgat tcattaatgc aggttgatca    3960
gatctcgatc ccgcgaaatt aatacgactc actataggga gaccacaacg gtttccctct    4020
agaaataatt ttgtttaact ttaagaagga gatatacccca tggaaagcc tgaactcacc    4080
gcgacgtctg tcgagaagtt tctgatcgaa aagttcgaca gcgtctccga cctgatgcag    4140
ctctcggagg gcgaagaatc tcgtgctttc agcttcgatg taggagggcg tggatatgtc    4200
ctgcgggtaa atagctgcgc cgatggtttc tacaaagatc gttatgttta tcggcacttt    4260
gcatcggccg cgctcccgat tccggaagtg cttgacattg gggaattcag cgagagcctg    4320
acctattgca tctcccgccg tgcacagggt gtcacgttgc aagacctgcc tgaaaccgaa    4380
ctgcccgctg ttctgcagcc ggtcgcggag gctatggatg cgatcgctgc ggccgatctt    4440
```

```
agccagacga gcgggttcgg cccattcgga ccgcaaggaa tcggtcaata cactacatgg    4500
cgtgatttca tatgcgcgat tgctgatccc catgtgtatc actggcaaac tgtgatggac    4560
gacaccgtca gtgcgtccgt cgcgcaggct ctcgatgagc tgatgctttg ggccgaggac    4620
tgccccgaag tccggcacct cgtgcacgcg gatttcggct ccaacaatgt cctgacggac    4680
aatggccgca taacagcggt cattgactgg agcgaggcga tgttcgggga ttcccaatac    4740
gaggtcgcca acatcttctt ctggaggccg tggttggctt gtatggagca gcagacgcgc    4800
tacttcgagc ggaggcatcc ggagcttgca ggatcgccgc ggctccgggc gtatatgctc    4860
cgcattggtc ttgaccaact ctatcagagc ttggttgacg gcaatttcga tgatgcagct    4920
tgggcgcagg gtcgatgcga cgcaatcgtc cgatccggag ccgggactgt cgggcgtaca    4980
caaatcgccc gcagaagcgc ggccgtctgg accgatggct gtgtagaagt actcgccgat    5040
agtggaaacc gacgcccag cactcgtccg agggcaaagg aatagtgagg tacagcttgg    5100
atcgatccgg ctgctaacaa agcccgaaag gaagctgagt tggctgctgc caccgctgag    5160
caataactag cataaccct tggggcctct aaacgggtct tgagggtttt tttgctgaaa    5220
ggaggaacta tatccggatg atcgtcgagg cctcacgtgt taacaagctt gcatgcctgc    5280
aggttt                                                               5286
```

<210> SEQ ID NO 25
<211> LENGTH: 5174
<212> TYPE: DNA
<213> ORGANISM: Artificial Sequence
<220> FEATURE:
<223> OTHER INFORMATION: plasmid QC533-1Y

<400> SEQUENCE: 25

```
gggagaaaat tacctaagtg tcatgtgcaa gtacaattat gaattcaatt tttaaacatg      60
tctatatgaa aaatatttta ttaagacaag tttgtctctt aaatatatct taataaccta     120
aaagattaat tattagttct cgatcagaat atcctaagtt aaaaataaat aaataaataa     180
aacaacaaaa attgaagcaa acaataacca ttaaataaag tttaatctgt aacgtggatt     240
acaagtggtg aaaatttata aatctggatt cgactttttc ttatgccact tagtggacaa     300 cttttcttcaa agaattctcg tattgctctg gcgcagttga gtaagtctat gtttggttta     360
cagatgggga gttttaaact caatttgaag agaaaaatga gtttaacatt atgtttaatt     420
tctctctaaa aatatgttta aagttaaaat ttagcctgaa aacttactta gggagacaca     480
actattagaa tatttttgca aactgcaatc caaattttga gtttaaaatt ttgcctcaac     540
actcaatttg ggaaaaacaa ctattaggat attcttgcaa atttagtttg taaacttaag     600
tttaacttaa acttaaattt ggaaactgta atccaaacat gtccttgtat tcctgtgaat     660
tgaaggtgcc tctcccacct tttaccaata aaaataaaaa gttgaatcta ttaacgctac     720
attcgttgtt atccattagg cgcactccaa agcttttata tttcgatcta agcattatct     780
ctcaaaagtt gtaccggaaa aacgttgcca tcgtacgtga agagaaagat ttcacgtaa     840 attacttttt cgttagatta tattttagtc cttatatttc tattattttt taaataaaaa     900
cttacaatcc tcactttata tatattaaaa taggtgtttt aaaataata attttagaaa     960 ctattcttca atgacaacat ctttaagaat tttctccaac aaaaatgttt ttaggtatt    1020 ttctaatcta ttatctcttt taatccatca ctctcatata caccttaaa ttattaaagt    1080 ctattaaaaa ataaataaaa atataagaag ctatctagaa ataattttat cctaaattct    1140
ttttatacga tacattatat gtggagcaca ttaggataaa ggaaaaaaag aaaacgttag    1200
```

-continued

```
ctaggcaaat taaaataata acaaaaatct tgataaaacg tttaatttga accaagaatg    1260
aaaatcaaac gtaaacaaga aaatgaataa taaataccaa tctacagtgg cccaccaaat    1320
tgccttcttt gcggaatcct actgttctgt cttgcaccac acgcactctc acaatgggtg    1380
gtttggctat aaagacacca ctcttacaca cccttcagc attcaccaca accctctctc     1440
tatattccat tgccacccag ttttgaatat attttattc cttctttgtt tcttcacttt     1500
cttccataca cataacaagg gcgaattcga cccagctttc ttgtacaaag tggttgatgg    1560
gatccatggc ccacagcaag cacggcctga aggaggagat gaccatgaag taccacatgg    1620
agggctgcgt gaacgccac aagttcgtga tcaccggcga gggcatcggc tacccttca      1680 agggcaagca gaccatcaac ctgtgcgtga tcgagggcgg cccctgccc ttcagcgagg     1740 acatcctgag cgccggcttc aagtacggcg accggatctt caccgagtac ccccaggaca   1800
tcgtggacta cttcaagaac agctgccccg ccggctacac ctggggccgg agcttcctgt   1860
tcgaggacgg cgccgtgtgc atctgtaacg tggacatcac cgtgagcgtg aaggagaact   1920
gcatctacca caagagcatc ttcaacggcg tgaacttccc cgccgacggc cccgtgatga   1980
agaagatgac caccaactgg gaggccagct gcgagaagat catgcccgtg cctaagcagg   2040
gcatcctgaa gggcgacgtg agcatgtacc tgctgctgaa ggacggcggc cggtaccggt   2100
gccagttcga caccgtgtac aaggccaaga gcgtgcccag caagatgccc gagtggcact   2160
tcatccagca caagctgctg cgggaggacc ggagcgacgc caagaaccag aagtggcagc   2220
tgaccgagca cgccatcgcc ttccccagcg ccctggcctg agagctcgaa tttccccgat   2280
cgttcaaaca tttggcaata agtttcttaa gattgaatc ctgttgccgg tcttgcgatg    2340
attatcatat aatttctgtt gaattacgtt aagcatgtaa taattaacat gtaatgcatg   2400
acgttattta tgagatgggt ttttatgatt agagtcccgc aattatacat ttaatacgcg   2460
atagaaaaca aaatatagcg cgcaaactag gataaattat cgcgcgcggt gtcatctatg   2520
ttactagatc gggaattcta gtggccggcc cagctgatat ccatcacact ggcggccgct   2580
cgagttctat agtgtcacct aaatcgtatg tgtatgatac ataaggttat gtattaattg   2640
tagccgcgtt ctaacgacaa tatgtccata tggtgcactc tcagtacaat ctgctctgat   2700
gccgcatagt taagccagcc ccgacacccg ccaacacccg ctgacgcgcc ctgacgggct   2760
tgtctgctcc cggcatccgc ttacagacaa gctgtgaccg tctccgggag ctgcatgtgt   2820
cagaggtttt caccgtcatc accgaaacgc gcgagacgaa agggcctcgt gatacgccta   2880
tttttatagg ttaatgtcat gaccaaaatc ccttaacgtg agttttcgtt ccactgagcg   2940
tcagaccccg tagaaaagat caaaggatct tcttgagatc cttttttct gcgcgtaatc    3000 tgctgcttgc aaacaaaaaa accaccgcta ccagcggtgg tttgtttgcc ggatcaagag   3060
ctaccaactc tttttccgaa ggtaactggc ttcagcagag cgcagatacc aaatactgtc   3120
cttctagtgt agccgtagtt aggccaccac ttcaagaact ctgtagcacc gcctacatac   3180
ctcgctctgc taatcctgtt accagtggct gctgccagtg gcgataagtc gtgtcttacc   3240
gggttggact caagacgata gttaccggat aaggcgcagc ggtcgggctg aacgggggt    3300 tcgtgcacac agcccagctt ggagcgaacg acctacaccg aactgagata cctacagcgt   3360
gagcattgag aaagcgccac gcttcccgaa gggagaaagg cggacaggta tccggtaagc   3420
ggcagggtcg aacaggaga gcgcacgagg gagcttccag ggggaaacgc ctggtatctt     3480
tatagtcctg tcgggtttcg ccacctctga cttgagcgtc gatttttgtg atgctcgtca   3540
```

```
gggggggcgga gcctatggaa aaacgccagc aacgcggcct ttttacggtt cctggccttt    3600
tgctggcctt ttgctcacat gttctttcct gcgttatccc ctgattctgt ggataaccgt    3660
attaccgcct ttgagtgagc tgataccgct cgccgcagcc gaacgaccga gcgcagcgag    3720
tcagtgagcg aggaagcgga agagcgccca atacgcaaac cgcctctccc cgcgcgttgg    3780
ccgattcatt aatgcaggtt gatcagatct cgatcccgcg aaattaatac gactcactat    3840
agggagacca caacggtttc cctctagaaa taattttgtt taactttaag aaggagatat    3900
acccatggaa aagcctgaac tcaccgcgac gtctgtcgag aagtttctga tcgaaaagtt    3960
cgacagcgtc tccgacctga tgcagctctc ggagggcgaa gaatctcgtg ctttcagctt    4020
cgatgtagga gggcgtggat atgtcctgcg ggtaaatagc tgcgccgatg gtttctacaa    4080
agatcgttat gtttatcggc actttgcatc ggccgcgctc ccgattccgg aagtgcttga    4140 cattgggaa ttcagcgaga gcctgaccta ttgcatctcc cgccgtgcac agggtgtcac    4200
gttgcaagac ctgcctgaaa ccgaactgcc cgctgttctg cagccggtcg cggaggctat    4260
ggatgcgatc gctgcggccg atcttagcca cgagcggg ttcggcccat tcggaccgca    4320
aggaatcggt caatacacta catggcgtga tttcatatgc gcgattgctg atccccatgt    4380
gtatcactgg caaactgtga tggacgacac cgtcagtgcg tccgtcgcgc aggctctcga    4440
tgagctgatg ctttgggccg aggactgccc cgaagtccgg cacctcgtgc acgcggattt    4500
cggctccaac aatgtcctga cggacaatgg ccgcataaca gcggtcattg actggagcga    4560
ggcgatgttc ggggattccc aatacgaggt cgccaacatc ttcttctgga ggccgtggtt    4620
ggcttgtatg gagcagcaga cgcgctactt cgagcggagg catccggagc ttgcaggatc    4680
gccgcggctc cgggcgtata tgctccgcat tggtcttgac caactctatc agagcttggt    4740
tgacggcaat ttcgatgatg cagcttgggc gcagggtcga tgcgacgcaa tcgtccgatc    4800
cggagccggg actgtcgggc gtacacaaat cgcccgcaga agcgcggccg tctggaccga    4860
tggctgtgta gaagtactcg ccgatagtgg aaaccgacgc cccagcactc gtccgagggc    4920
aaaggaatag tgaggtacag cttggatcga tccggctgct aacaaagccc gaaaggaagc    4980
tgagttggct gctgccaccg ctgagcaata actagcataa ccccttgggg cctctaaacg    5040
ggtcttgagg ggttttttgc tgaaaggagg aactatatcc ggatgatcgt cgaggcctca    5100
cgtgttaaca agcttgcatg cctgcaggtt tatcaacaag tttgtacaaa aaagcaggct    5160
ccgaattcgc cctt                                                      5174
```

<210> SEQ ID NO 26  
<211> LENGTH: 22  
<212> TYPE: DNA  
<213> ORGANISM: Artificial Sequence  
<220> FEATURE:  
<223> OTHER INFORMATION: SAMS forward primer (SAMS-76F)

<400> SEQUENCE: 26

```
aggcttgttg tgcagttttt ga                                               22
```

<210> SEQ ID NO 27  
<211> LENGTH: 22  
<212> TYPE: DNA  
<213> ORGANISM: Artificial Sequence  
<220> FEATURE:  
<223> OTHER INFORMATION: FAM labeled ALS probe (ALS-100T)

<400> SEQUENCE: 27

```
ccacacaaca caatggcggc ca                                               22
```

<210> SEQ ID NO 28
<211> LENGTH: 22
<212> TYPE: DNA
<213> ORGANISM: Artificial Sequence
<220> FEATURE:
<223> OTHER INFORMATION: ALS reverse primer (ALS-163R)

<400> SEQUENCE: 28
ggaagaagag aatcgggtgg tt                                      22

<210> SEQ ID NO 29
<211> LENGTH: 24
<212> TYPE: DNA
<213> ORGANISM: Artificial Sequence
<220> FEATURE:
<223> OTHER INFORMATION: GFP forward primer (GFP-24F)

<400> SEQUENCE: 29
gaccaaggag atgaccatga agta                                    24

<210> SEQ ID NO 30
<211> LENGTH: 14
<212> TYPE: DNA
<213> ORGANISM: Artificial Sequence
<220> FEATURE:
<223> OTHER INFORMATION: FAM labeled GFP probe(GFP-51T)

<400> SEQUENCE: 30
catggagggc tgcg                                               14

<210> SEQ ID NO 31
<211> LENGTH: 20
<212> TYPE: DNA
<213> ORGANISM: Artificial Sequence
<220> FEATURE:
<223> OTHER INFORMATION: GFP reverse primer(GFP-92R)

<400> SEQUENCE: 31
ccggtgatca cgaacttgtg                                         20

<210> SEQ ID NO 32
<211> LENGTH: 24
<212> TYPE: DNA
<213> ORGANISM: Artificial Sequence
<220> FEATURE:
<223> OTHER INFORMATION: HSP forward primer (HSP-F1)

<400> SEQUENCE: 32
caaacttgac aaagccacaa ctct                                    24

<210> SEQ ID NO 33
<211> LENGTH: 20
<212> TYPE: DNA
<213> ORGANISM: Artificial Sequence
<220> FEATURE:
<223> OTHER INFORMATION: VIC labeled HSP probe (HSP probe)

<400> SEQUENCE: 33
ctctcatctc atataaatac                                         20

<210> SEQ ID NO 34
<211> LENGTH: 21
<212> TYPE: DNA
<213> ORGANISM: Artificial Sequence
<220> FEATURE:

<223> OTHER INFORMATION: HSP reverse primer (HSP-R1)

<400> SEQUENCE: 34
ggagaaattg gtgtcgtgga a                                             21

<210> SEQ ID NO 35
<211> LENGTH: 100
<212> TYPE: DNA
<213> ORGANISM: Artificial Sequence
<220> FEATURE:
<223> OTHER INFORMATION: attL1

<400> SEQUENCE: 35
caaataatga ttttattttg actgatagtg acctgttcgt tgcaacaaat tgataagcaa    60 tgcttttta taatgccaac tttgtacaaa aaagcaggct                          100

<210> SEQ ID NO 36
<211> LENGTH: 100
<212> TYPE: DNA
<213> ORGANISM: Artificial Sequence
<220> FEATURE:
<223> OTHER INFORMATION: attL2

<400> SEQUENCE: 36
caaataatga ttttattttg actgatagtg acctgttcgt tgcaacaaat tgataagcaa    60
tgctttctta taatgccaac tttgtacaag aaagctgggt                         100

<210> SEQ ID NO 37
<211> LENGTH: 125
<212> TYPE: DNA
<213> ORGANISM: Artificial Sequence
<220> FEATURE:
<223> OTHER INFORMATION: attR1

<400> SEQUENCE: 37
acaagtttgt acaaaaaagc tgaacgagaa acgtaaaatg atataaatat caatatatta    60
aattagattt tgcataaaaa acagactaca taatactgta aaacacaaca tatccagtca   120
ctatg                                                              125

<210> SEQ ID NO 38
<211> LENGTH: 125
<212> TYPE: DNA
<213> ORGANISM: Artificial Sequence
<220> FEATURE:
<223> OTHER INFORMATION: attR2

<400> SEQUENCE: 38
accactttgt acaagaaagc tgaacgagaa acgtaaaatg atataaatat caatatatta    60
aattagattt tgcataaaaa acagactaca taatactgta aaacacaaca tatccagtca   120
ctatg                                                              125

<210> SEQ ID NO 39
<211> LENGTH: 21
<212> TYPE: DNA
<213> ORGANISM: Artificial Sequence
<220> FEATURE:
<223> OTHER INFORMATION: attB1

<400> SEQUENCE: 39
caagtttgta caaaaaagca g                                             21

```
<210> SEQ ID NO 40
<211> LENGTH: 21
<212> TYPE: DNA
<213> ORGANISM: Artificial Sequence
<220> FEATURE:
<223> OTHER INFORMATION: attB2

<400> SEQUENCE: 40
ccactttgta caagaaagct g                                               21

<210> SEQ ID NO 41
<211> LENGTH: 757
<212> TYPE: DNA
<213> ORGANISM: Glycine max

<400> SEQUENCE: 41
attcaccaca accctctctc tatattccat tgccacccag ttttgaatat attttttattc     60 cttctttgtt tcttcacttt cttccataca cataaccatg tcttctcaga ctgttgtcct    120
caaagttggt atgtcatgtc aagggtgtgc tggagcagtg aacagggttt tgggaaaaat    180
ggaaggtgtt gagtcatttg acattgatct gaaggagcag aaggtgacag tgaaaggaaa    240
tgtggagtca gatgaagttc tgcaagccgt ttccaaatct gggaagaaga ctgcattctg    300
ggtggatgaa gcaccacaat ctaaaaacaa gcctttagaa agtgcacctg ttgcctcaga    360
aaacaagcct tcagaagctg caactgttgc ctcagctgag cctgaaaaca agccttcaga    420
agctgcaatt gttgattcag ctgagcctga aaacaagcct tcagatactg ttgttgaaac    480
tgttgcttaa ggcatttgtg gttctatttt tctatgtgga agtaggtctg tttcatatag    540
tatttcatgt gctttgtgca tgtcagctat tatatttggt gtgttgttac tggtatctaa    600
gctacaataa cttgtggcct attttttcaca tgagatacat ttcatgggtg ctataattta    660
gaatttgaac ctgtcactct tgttactact gtttttgttc agtctttat attcttacca    720 caacttgatc atattggaaa gagcttattt tccgctc                             757

<210> SEQ ID NO 42
<211> LENGTH: 1524
<212> TYPE: DNA
<213> ORGANISM: Glycine max

<400> SEQUENCE: 42
taagggagaa aattacctaa gtgtcatgtg caagtacaat tatgaattca attttttaaac    60 atgtctatat gaaaaaatat ttattaagac aagtttgtct cttaaatata tcttaatacc    120 ttaaagatt aattattagt tctcgatcag aatatcctaa gttaaaaata aataaataaa    180
taaaacaaca aaaattgaag caaacaataa ccattaaata agtttaatc tgtaacgtgg    240 attacaagtg gtgaaaattt ataaatctgg attcgacttt tcttatgcc acttagtgga    300 caactttctt caagaattc tcgtattgct ctggcgcagt tgagtaagtc tatgtttggt    360
ttacagatgg ggagttttaa actcaatttg aagagaaaaa tgagtttaac attatgttta    420
atttctctct aaaaatatgt ttaaagttaa aatttagcct gaaaacttac ttagggagac    480
acaactatta gaatattttt gcaaactgca atccaaattt tgagtttaaa attttgcctc    540
aacactcaat ttgggaaaaa caactattag gatattcttg caaatttagt ttgtaaactt    600
aagtttaact taaacttaaa tttggaaact gtaatccaaa catgtccttg tattcctgtg    660
aattgaaggt gcctctccca cctttacca ataaaaataa aaagttgaat ctattaacgc    720
tacattcgtt gttatccatt aggcgcactc caaagctttt atatttcgat ctaagcatta    780
```

```
tctctcaaaa gttgtaccgg aaaaacgttg ccatcgtacg tgagaagaaa gattttcacg      840
taaattactt tttcgttaga ttatatttta gtccttatat ttctattatt ttttaaataa      900
aaacttacaa tcctcacttt atatatatta aaataggtgt tttaaaaata ataattttag      960
aaactattct tcaatgacaa catctttaag aattttctcc aacaaaaatg tttttaggta     1020
tttttctaat ctattatctc ttttaatcca tcactctcat atacaccttt aaattattaa     1080
agtctattaa aaaataaata aaaatataag aagctatcta gagaataatt tatcctaaat     1140 tcttttata cgatacatta tatgtggagc acattaggat aaaggaaaaa aagaaaacgt     1200
tagctaggca aattaaaata ataacaaaaa tcttgataaa acgtttaatt tgaaccaaga     1260
atgaaaatca aacgtaaaca agaaaatgaa taataaatac caatctacag tggcccacca     1320
aattgccttc tttgcggaat cctactgttc tgtcttgcac cacacgcact ctcacaatgg     1380
gtggtttggc tataaagaca ccactcttac acaccctttc agcattcacc acaaccctct     1440
ctctatattc cattgccacc cagttttgaa tatatttta ttccttcttt gtttcttcac     1500
tttcttccat acacataacc atgt                                             1524

<210> SEQ ID NO 43
<211> LENGTH: 91
<212> TYPE: DNA
<213> ORGANISM: Glycine max

<400> SEQUENCE: 43
cacaaccctc tctctatatt ccattgccac ccagttttga atatattttt attccttctt       60
tgtttcttca ctttcttcca tacacataac c                                      91
```

SOYBEAN CCP1 PROMOTER AND ITS USE IN CONSTITUTIVE EXPRESSION OF TRANSGENIC GENES IN PLANTS

This application claims the benefit of U.S. Provisional Application No. 61/681,759, filed Aug. 10, 2012, the entire content of which is herein incorporated by reference.

FIELD OF THE INVENTION

This invention relates to a plant promoter GM-CCP1 and fragments thereof and their use in altering expression of at least one heterologous nucleotide sequence in plants in a tissue-independent or constitutive manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns an isolated polynucleotide comprising a promoter wherein said promoter comprises the nucleotide sequence set forth in SEQ ID NOs: 1, 2, 3, 4, 5, 6, 7 or 42 or said promoter comprises a functional fragment of the nucleotide sequence set forth in SEQ ID NOs: 1, 2, 3, 4, 5, 6, 7 or 42, or wherein said promoter comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NO:1, 2, 3, 4, 5, 6, 7 or 49.

In a second embodiment, this invention concerns an isolated polynucleotide comprising a promoter region of a *Glycine max* copper chaperone homolog (GM-CCP1) gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 11311, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 12312, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298 or 1299 consecutive nucleotides, wherein the first nucleotide deleted is the cytosine nucleotide ['C'] at position 1 of SEQ ID NO:1. This invention also concerns an isolated polynucleotide of the embodiments disclosed herein, wherein the polynucleotide is a constitutive promoter.

In a third embodiment, this invention concerns a recombinant DNA construct comprising at least one heterologous nucleotide sequence operably linked to the promoter of the invention.

In a fourth embodiment, this invention concerns a cell, plant, or seed comprising a recombinant DNA construct of the present disclosure.

In a fifth embodiment, this invention concerns plants comprising this recombinant DNA construct and seeds obtained from such plants.

In a sixth embodiment, this invention concerns a method of altering (increasing or decreasing) expression of at least one heterologous nucleic acid fragment in a plant cell which comprises:
(a) transforming a plant cell with the recombinant expression construct described above;
(b) growing fertile mature plants from the transformed plant cell of step (a);
(c) selecting plants containing the transformed plant cell wherein the expression of the heterologous nucleic acid fragment is increased or decreased.

In a seventh embodiment, this invention concerns a method for expressing a yellow fluorescent protein ZS-GREEN1 (GFP) in a host cell comprising:
(a) transforming a host cell with a recombinant expression construct comprising at least one ZS-GREEN1 nucleic acid fragment operably linked to a promoter wherein said promoter consists essentially of the nucleotide sequence set forth in SEQ ID NOs:1, 2, 3, 4, 5, 6, 7 or 42; and
(b) growing the transformed host cell under conditions that are suitable for expression of the recombinant DNA construct, wherein expression of the recombinant DNA construct results in production of increased levels of ZS-GREEN1 protein in the transformed host cell when compared to a corresponding nontransformed host cell.

In an eighth embodiment, this invention concerns an isolated nucleic acid fragment comprising a plant copper chaperone homolog (CCP1) gene promoter.

In a ninth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a tenth embodiment, this invention concerns an isolated polynucleotide linked to a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1 is the relative expression of the soybean copper chaperone homolog (CCP1) gene (PSO319685, Glyma02g19380.1) in twenty one soybean tissues by Illumina (Solexa) digital gene expression dual-tag-based mRNA profiling. The gene expression profile indicates that the CCP1 gene is expressed similarly in all the checked tissues.

Figure 2A:
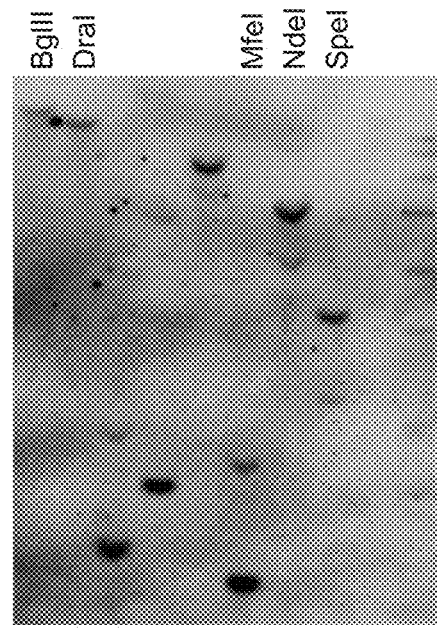
Figure 2B:
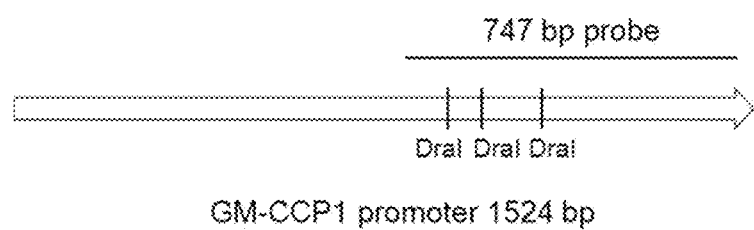

FIG. 2 is CCP1 promoter copy number analysis by Southern. FIG. 2A is the image of a Southern blot hybridized with a 747 bp CCP1 promoter probe made with primers QC533-S4 and QC533-A by PCR. FIG. 2B shows restriction enzyme recognitions sites in the CCP1 probe region.

Figure 3A:
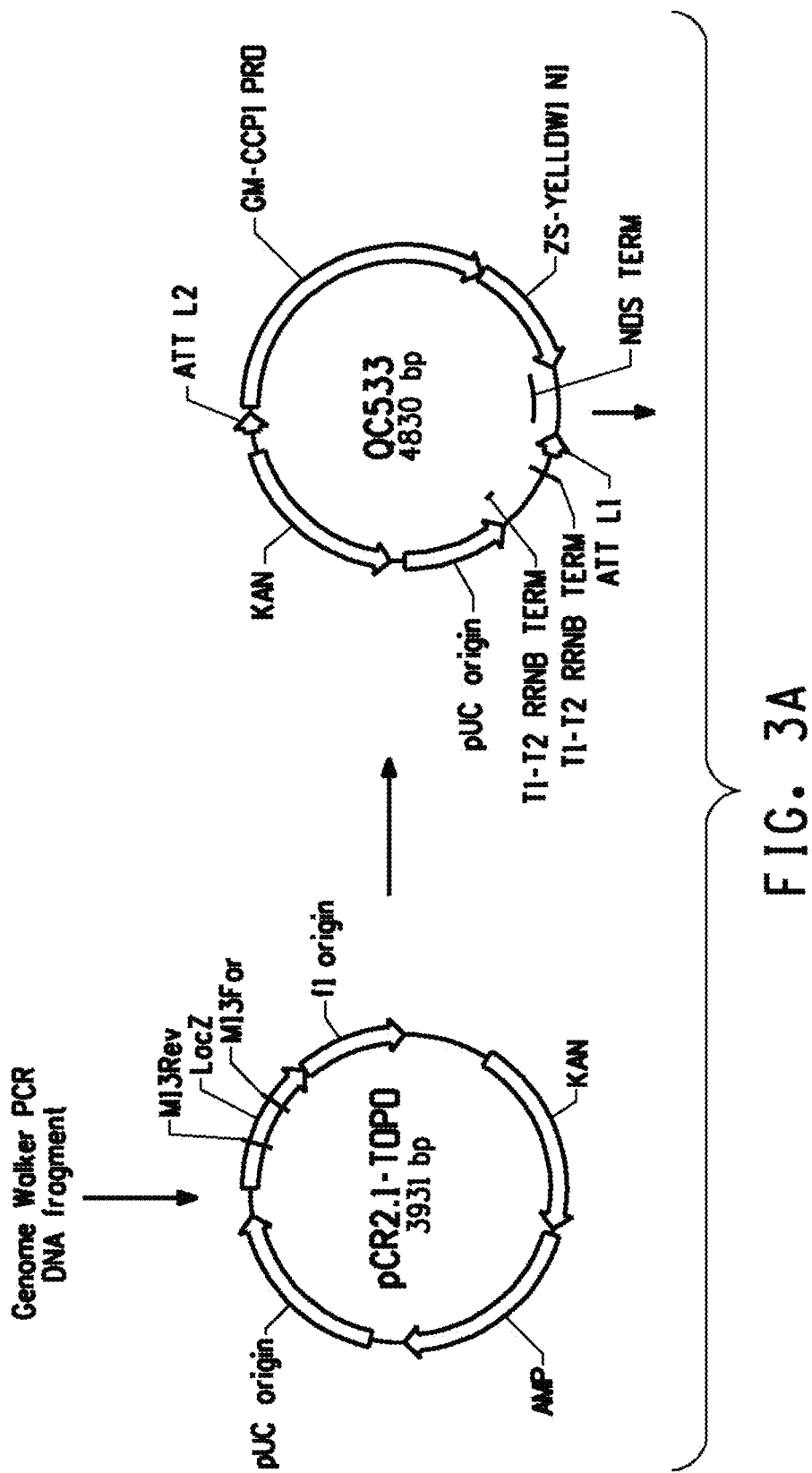
Figure 3B:
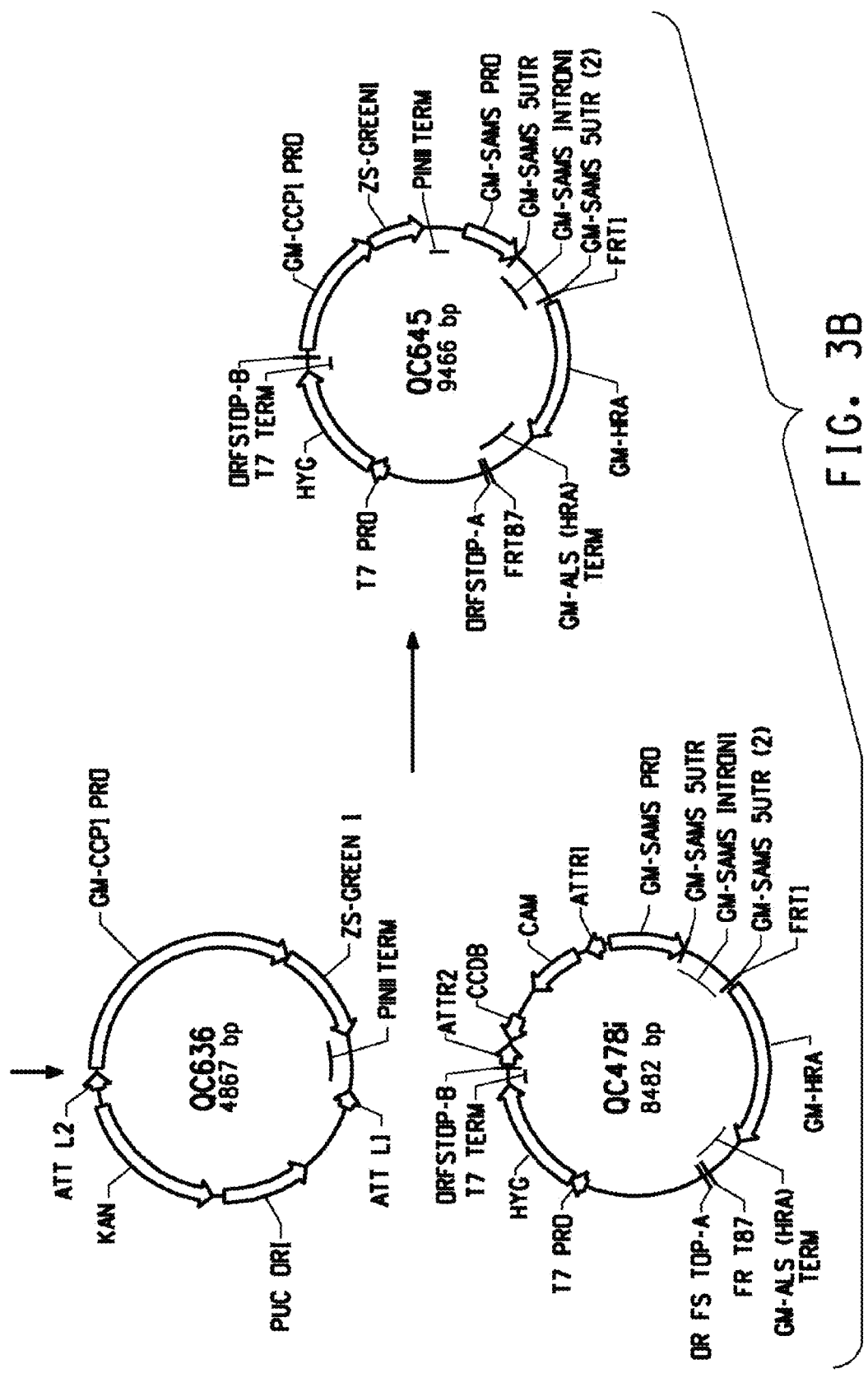

FIG. 3A-3B shows the maps of plasmids pCR2.1-TOPO, QC533, QC636, QC478i, and QC645. The 6952 bp AscI-AscI fragment of QC645 is used to produce transgenic soybean plants.

Figure 4A:
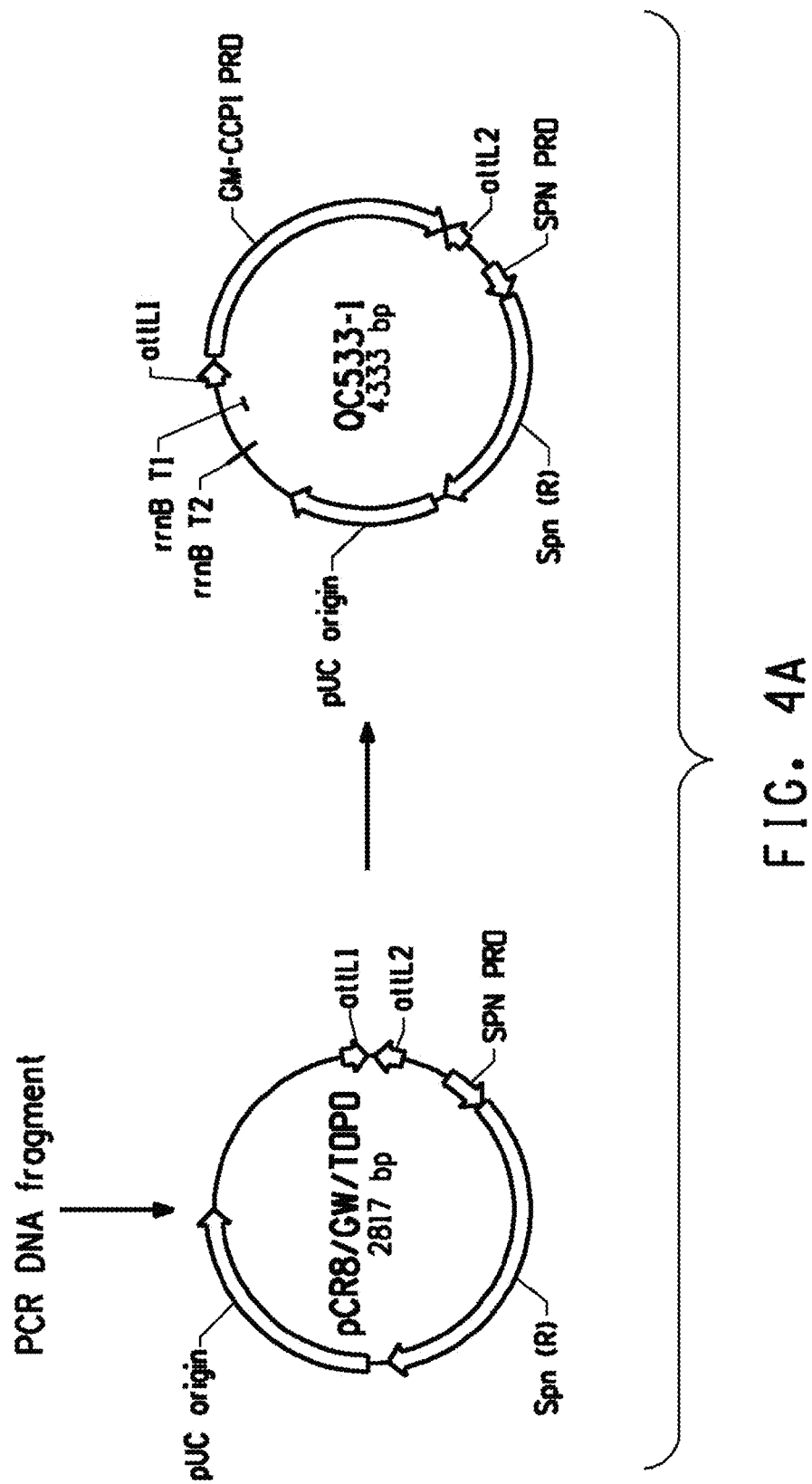
Figure 4B:
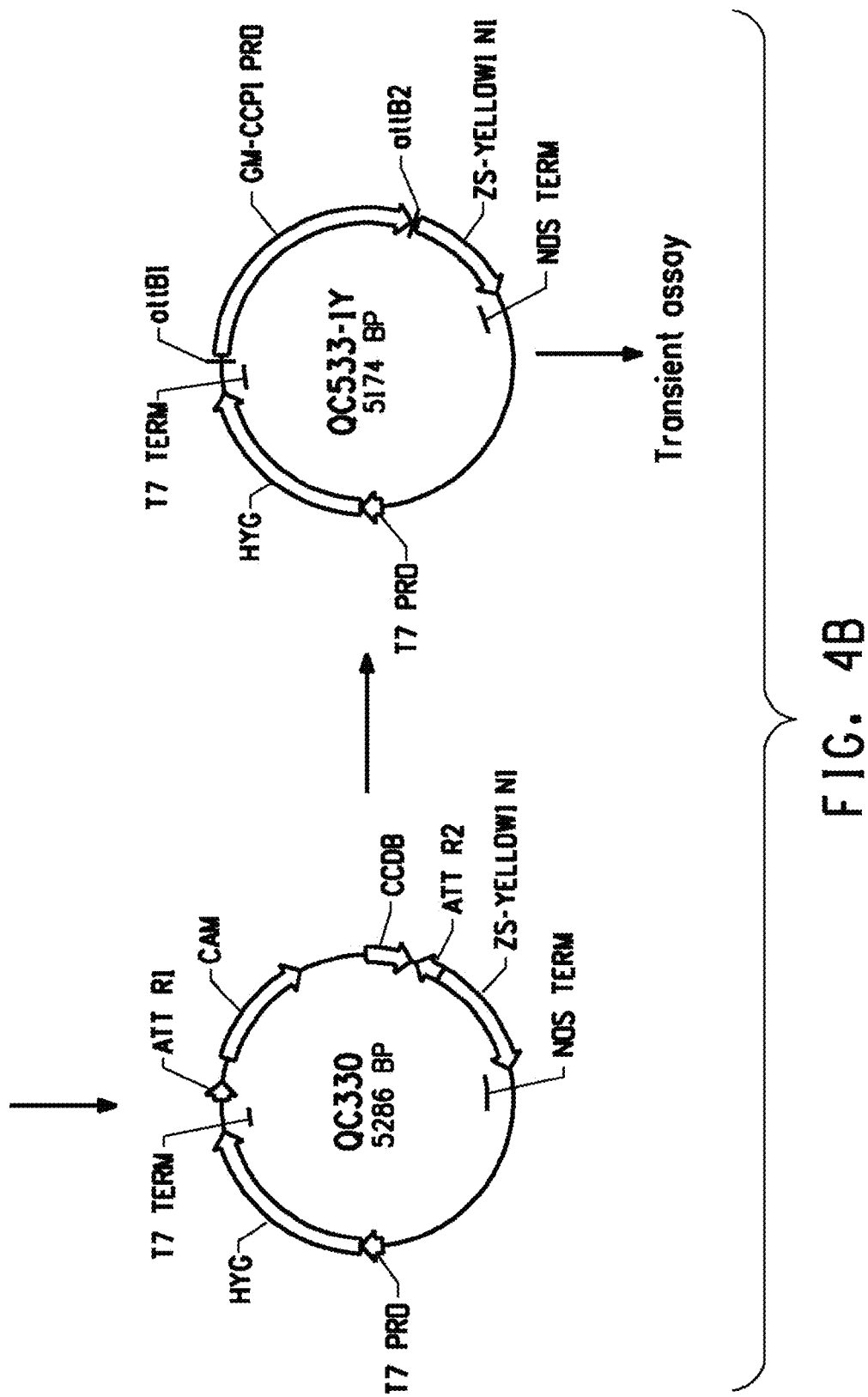
Figure 4C:
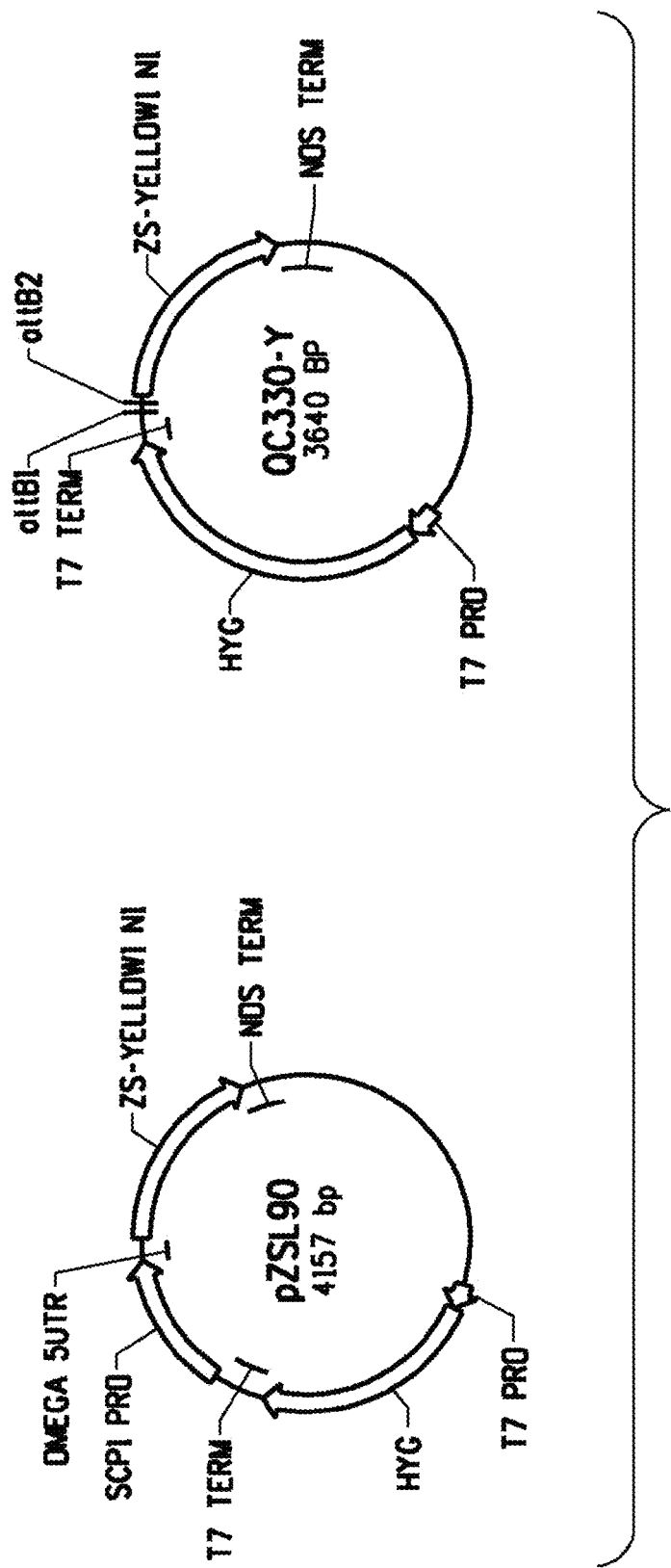

FIG. 4A-4B shows the maps of plasmids pCR8/GW/TOPO, QC533-1, QC330, and QC533-1Y containing a full length 1516 bp CCP1 promoter. Other promoter deletion constructs QC533-2Y, QC533-3Y, QC533-4Y, and QC533-5Y containing the 1186, 987, 747, 484, and 225 bp truncated CCP1 promoters, respectively, have the same map configuration, except for the truncated promoter sequences. FIG. 4C shows the maps of plasmids pZSL90 as a strong constitutive promoter (SCP1) positive control and QC330-Y as a promoter-less negative control in transient expression assays.

Figure 5:
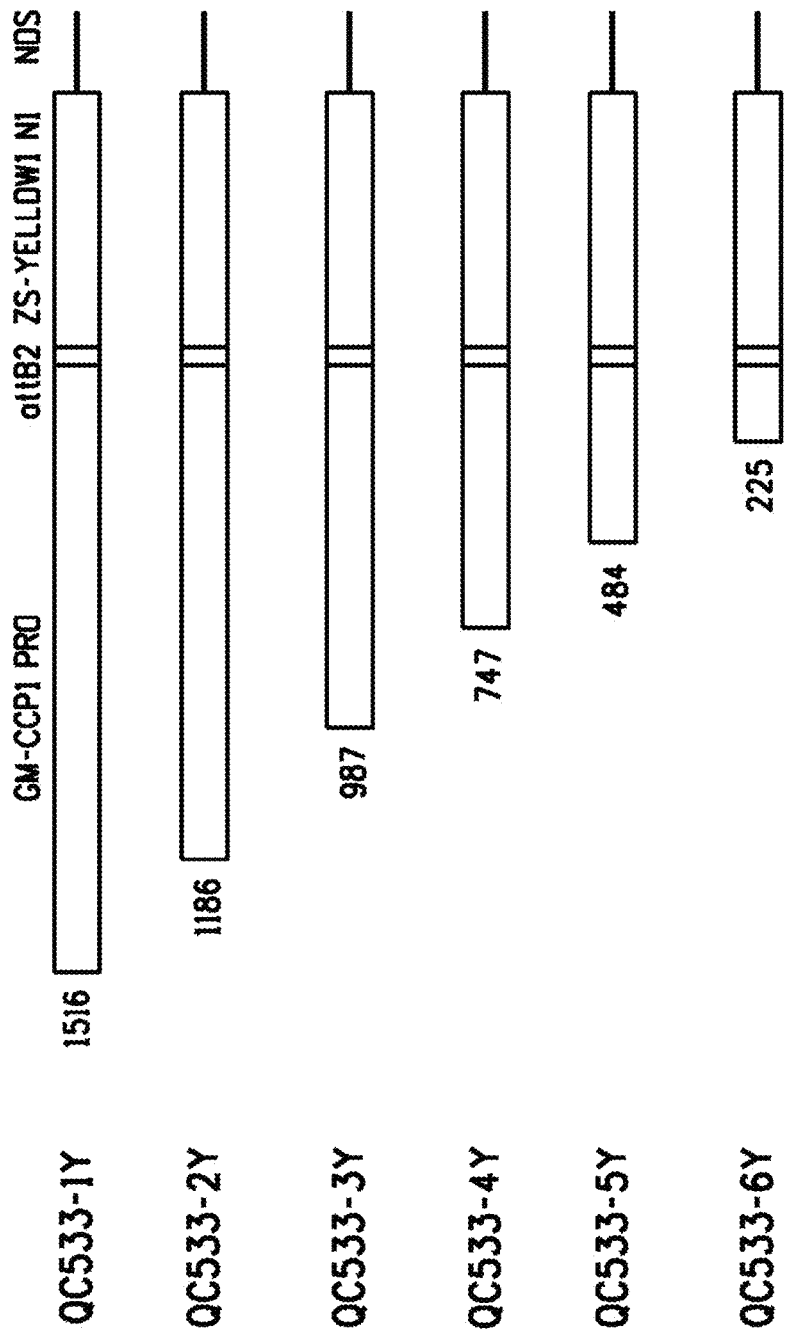

FIG. 5 is the schematic descriptions of the full length CCP1 promoter its progressive truncations in constructs, QC533-1Y, QC533-2Y, QC533-3Y, QC533-4Y, QC533-5Y, and QC533-6Y, of the CCP1 promoter. The size of each promoter is given at the left end of each drawing. QC533-1Y has 1516 bp of the 1524 bp CCP1 promoter in QC533 with the XmaI and NcoI sites removed and like the other deletion constructs with the attB site between the promoter and ZS-YELLOW N1 reporter gene.

FIGS. 6A-6H show the transient expression of the fluorescent protein reporter gene ZS-YELLOW1 N1 in the cotyledons of germinating soybean seeds. FIG. 6A shows the expression of pZSL90. FIG. 6B shows the expression of QCC330-Y. The reporter gene is driven by the full length CCP1 promoter in QC533-1Y (labeled as QC532-1Y, FIG. 6C) or by progressively truncated CCP1 promoters in the transient expression constructs QC533-2Y (labeled as QC532-2Y, FIG. 6D), QC533-3Y (labeled as QC532-3Y, FIG. 6E), QC533-4Y (labeled as QC532-4Y, FIG. 6F), QC533-5Y(labeled as QC532-5Y, FIG. 6G) and QC533-6Y (labeled as QC532-6Y, FIG. 6 H).

Figure 7I:
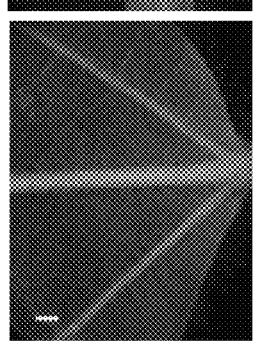
Figure 7J:
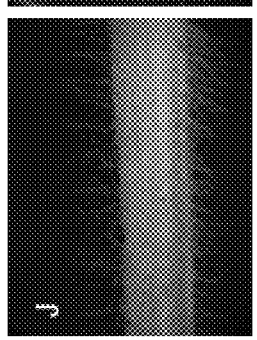
Figure 7K:
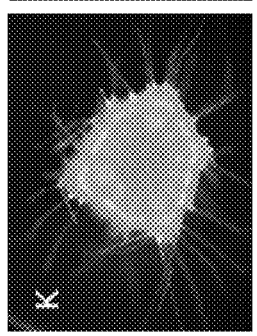
Figure 7L:
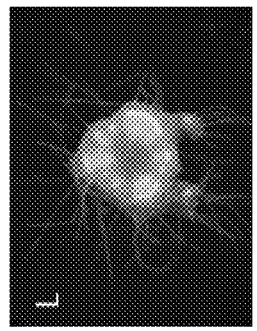
Figure 7M:
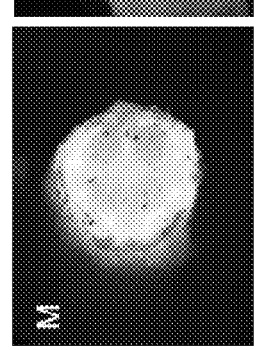
Figure 7N:
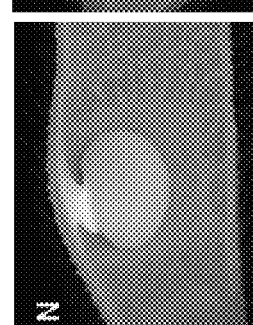
Figure 7O:
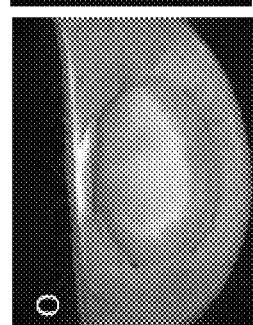
Figure 7P:
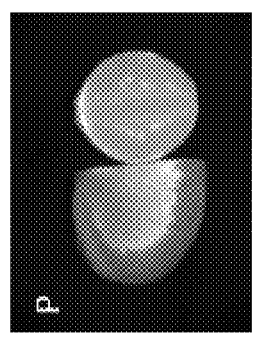

FIG. 7A-7P shows the stable expression of the fluorescent protein reporter gene ZS-GREEN1 in different tissues of transgenic soybean plants containing a single copy of CCP1:GFP DNA of construct QC645, comprising the full length CCP1 promoter of SEQ ID NO:1. (A: Embryonic callus, B: Young somatic embryos, C: Early cotyledon somatic embryos, D: Mature somatic embryos, E: Flower bud showing pedals and sepals, F: Open flower, G: Stamen, filaments and anthers, H: Longitudinal section of ovary showing ovules, I: Leaf, abaxial surface showing veins, J: Stem, cross section, K: Petiole, cross section showing vascular bundles, L: Stem, longitudinal section showing vascular bundles, M: Root, cross section showing vascular bundles, N: Young pod, open showing inner surface and a R3 seed, O: Filled pod, open showing inner surface and a R5 seed, P: Cross section of a R5 seed showing embryo and seed coat).

Figure 8A:
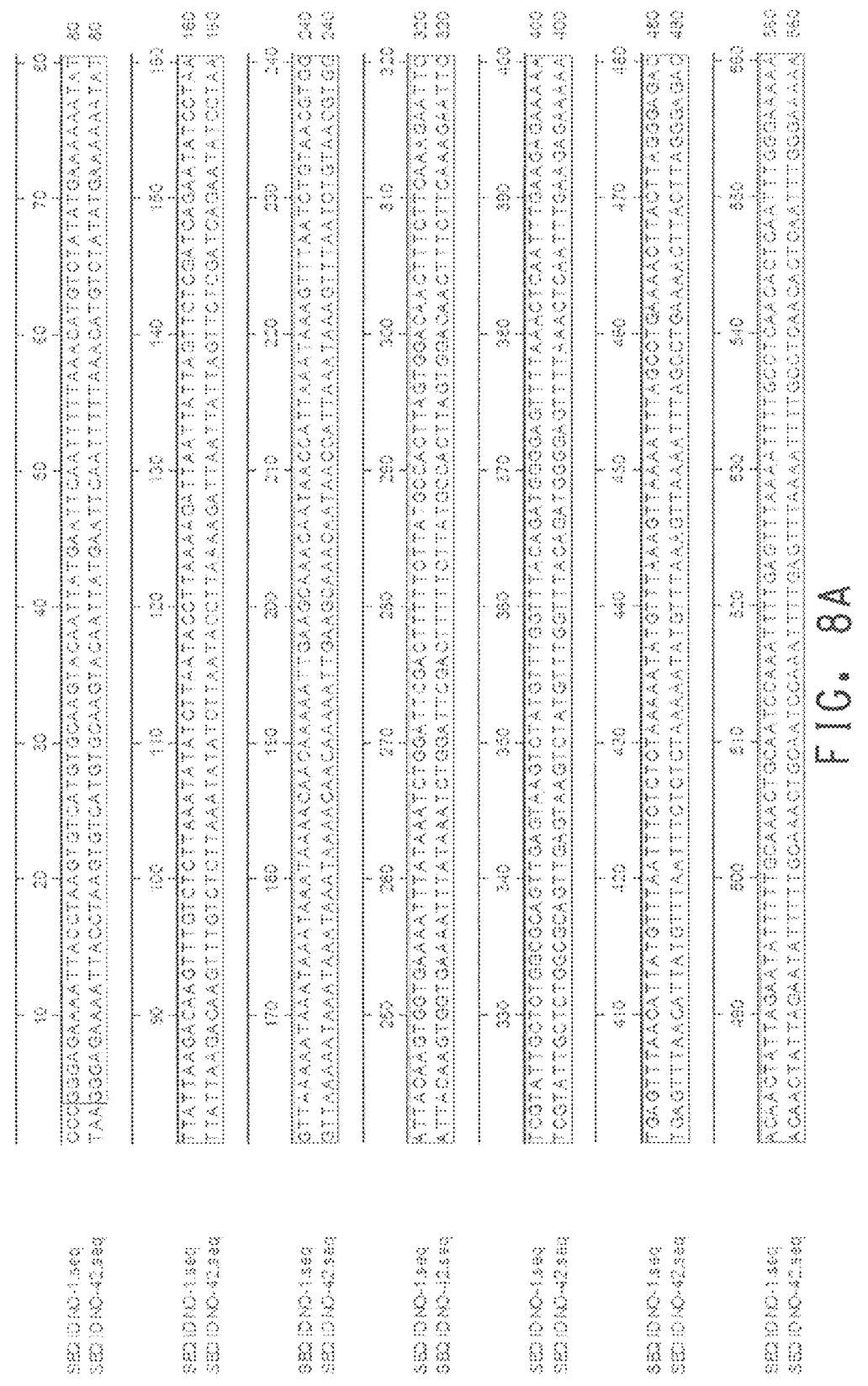
Figure 8B:
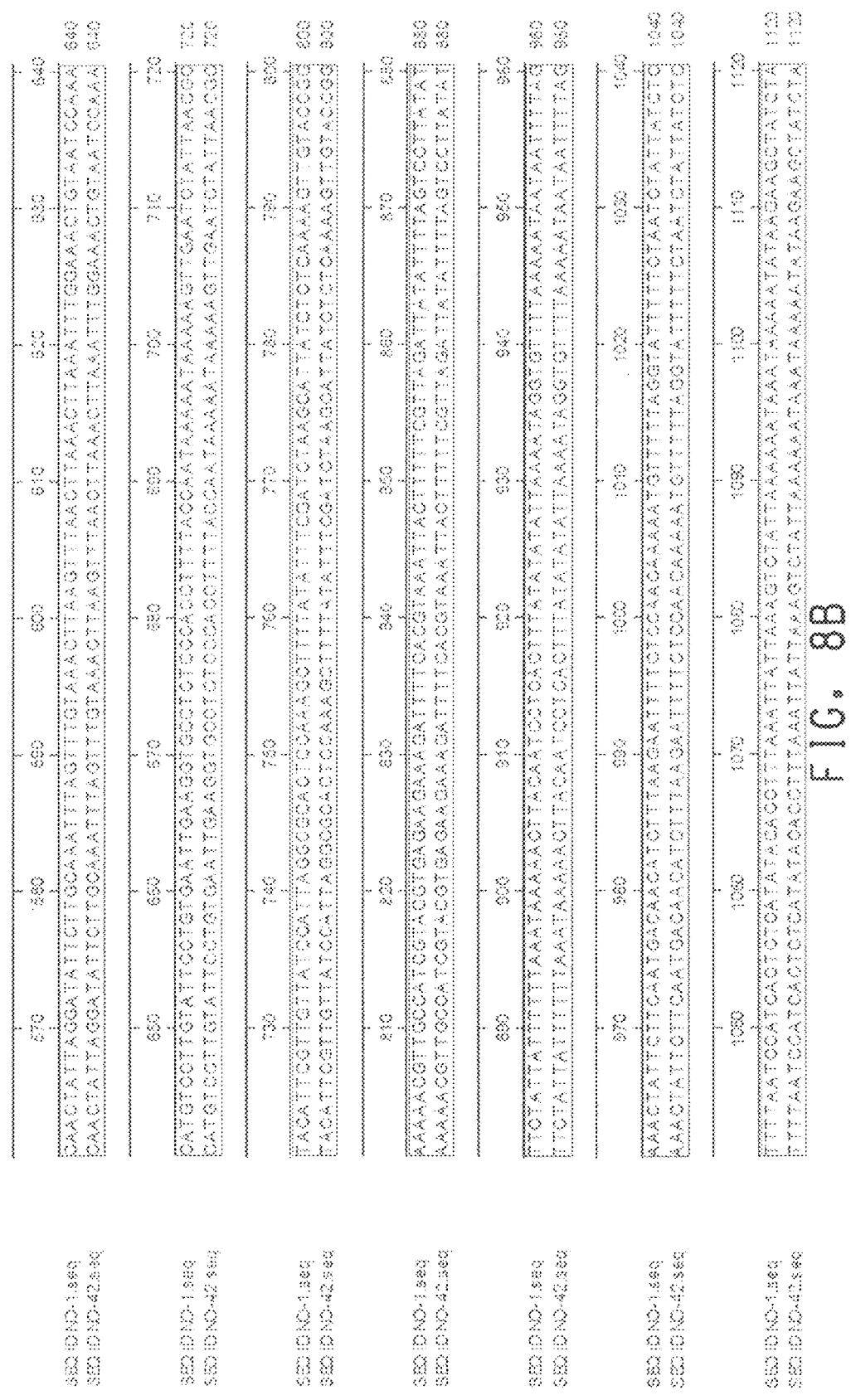
Figure 8C:
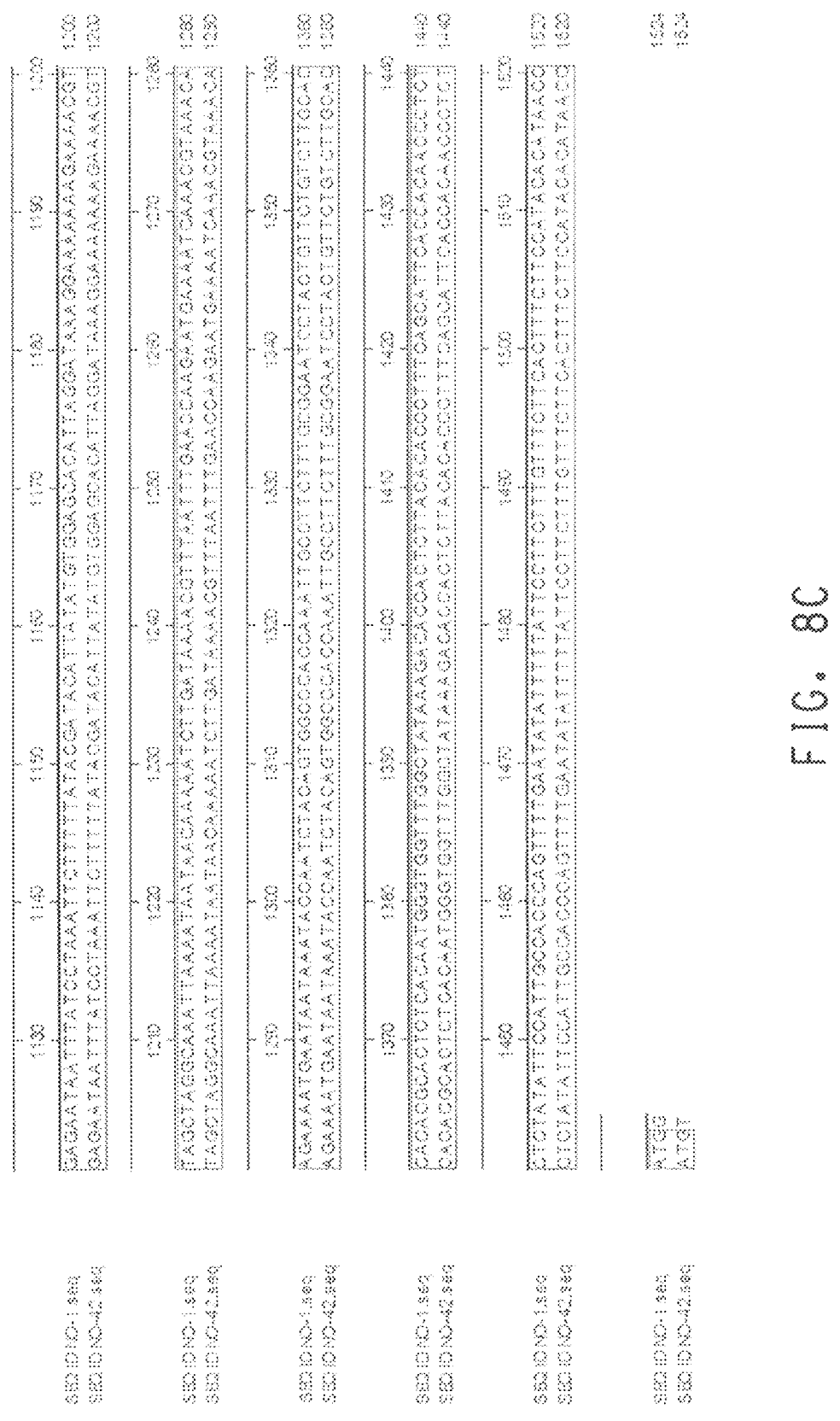

FIG. 8 A-C shows a nucleotide alignment of SEQ ID NO:1, comprising the CCP1 promoter of the disclosure, and SEQ ID NO:42, comprising a 1524 bp native soybean genomic DNA from Gm02:18396445 . . . 18397500 (rev) (Schmutz J. et al., Genome sequence of the palaeopolyploid soybean, Nature 463:178-183, 2010). FIG. 8D shows the percent sequence identity between the CCP1 promoter of SEQ ID NO:1 and the corresponding native soybean genomic DNA of SEQ ID NO:42, based on the Clustal V method of alignment with pairwise alignment default parameters (KTUPLE=2, GAP PENALTY=5, WINDOW=4 and DIAGONALS SAVED=4).

The sequence descriptions summarize the Sequence Listing attached hereto. The Sequence Listing contains one letter codes for nucleotide sequence characters and the single and three letter codes for amino acids as defined in the IUPAC-IUB standards described in Nucleic Acids Research 13:3021-3030 (1985) and in the *Biochemical Journal* 219 (2):345-373 (1984).

SEQ ID NO:1 is the DNA sequence comprising a 1524 bp (base pair) soybean CCP1 promoter flanked by XmaI (cccggg) and NcoI (ccatgg) restriction sites.

SEQ ID NO:2 is a 1516 bp full length of the CCP1 promoter shown in SEQ ID NO:1 (bp 4-1519 of SEQ ID NO:1) with the 5' end XmaI and 3' end NcoI sites removed.

SEQ ID NO:3 is a 1186 bp truncated form of the CCP1 promoter shown in SEQ ID NO:1 (bp 334-1562 of SEQ ID NO:1).

SEQ ID NO:4 is a 987 bp truncated form of the CCP1 promoter shown in SEQ ID NO:1 (bp 533-1562 of SEQ ID NO:1).

SEQ ID NO:5 is a 747 bp truncated form of the CCP1 promoter shown in SEQ ID NO:1 (bp 773-1562 of SEQ ID NO:1).

SEQ ID NO:6 is a 484 bp truncated form of the CCP1 promoter shown in SEQ ID NO:1 (bp 1036-1562 of SEQ ID NO:1).

SEQ ID NO:7 is a 225 bp truncated form of the CCP1 promoter shown in SEQ ID NO:1 (bp 1295-1562 of SEQ ID NO:1).

SEQ ID NO:8 is an oligonucleotide primer used as a gene-specific sense primer in the PCR amplification of the full length CCP1 promoter in SEQ ID NO:1 when paired with SEQ ID NO:9. A restriction enzyme XmaI recognition site CCCGGG is included for subsequent cloning.

SEQ ID NO:9 is an oligonucleotide primer used as a gene-specific antisense primer in the PCR amplification of the full length CCP1 promoter in SEQ ID NO:1 when paired with SEQ ID NO:8. A restriction enzyme NcoI recognition site CCATGG is included for subsequent cloning.

SEQ ID NO:10 is an oligonucleotide primer used as an antisense primer in the PCR amplifications of the truncated CCP1 promoters in SEQ ID NOs:2, 3, 4, 5, 6, or 7 when paired with SEQ ID NOs: 11, 12, 13, 14, 15, or 16, respectively.

SEQ ID NO:11 is an oligonucleotide primer used as a sense primer in the PCR amplification of the full length CCP1 promoter in SEQ ID NO:2 when paired with SEQ ID NO:10.

SEQ ID NO:12 is an oligonucleotide primer used as a sense primer in the PCR amplification of the truncated CCP1 promoter in SEQ ID NO:3 when paired with SEQ ID NO:10.

SEQ ID NO:13 is an oligonucleotide primer used as a sense primer in the PCR amplification of the truncated CCP1 promoter in SEQ ID NO:4 when paired with SEQ ID NO:10.

SEQ ID NO:14 is an oligonucleotide primer used as a sense primer in the PCR amplification of the truncated CCP1 promoter in SEQ ID NO:5 when paired with SEQ ID NO:10.

SEQ ID NO:15 is an oligonucleotide primer used as a sense primer in the PCR amplification of the truncated CCP1 promoter in SEQ ID NO:6 when paired with SEQ ID NO:10.

SEQ ID NO:16 is an oligonucleotide primer used as a sense primer in the PCR amplification of the truncated CCP1 promoter in SEQ ID NO:7 when paired with SEQ ID NO:10.

SEQ ID NO:17 is the 673 bp nucleotide sequence of the putative soybean copper chaperone homolog CCP1 cDNA (PSO319685). Nucleotides 1 to 91 are the 5' untranslated sequence, nucleotides 92 to 94 are the translation initiation codon, nucleotides 92 to 484 are the polypeptide coding region, nucleotides 482 to 484 are the termination codon, and nucleotides 485 to 673 are part of the 3' untranslated sequence.

SEQ ID NO:18 is the predicted 130 aa (amino acid) long peptide sequence translated from the coding region of the putative soybean copper chaperone homolog CCP1 nucleotide sequence SEQ ID NO:17.

SEQ ID NO:19 is the 4830 bp sequence of plasmid QC533.

SEQ ID NO:20 is the 4867 bp sequence of plasmid QC636.

SEQ ID NO:21 is the 8482 bp sequence of plasmid QC478i.

SEQ ID NO:22 is the 9466 bp sequence of plasmid QC645.

SEQ ID NO:23 is the 4333 bp sequence of plasmid QC533-1.

SEQ ID NO:24 is the 5286 bp sequence of plasmid QC330.

SEQ ID NO:25 is the 5174 bp sequence of plasmid QC533-1Y.

SEQ ID NO:26 is a sense primer used in quantitative PCR analysis of SAMS:HRA transgene copy numbers.

SEQ ID NO:27 is a FAM labeled fluorescent DNA oligo probe used in quantitative PCR analysis of SAMS:HRA transgene copy numbers.

SEQ ID NO:28 is an antisense primer used in quantitative PCR analysis of SAMS:HRA transgene copy numbers.

SEQ ID NO:29 is a sense primer used in quantitative PCR analysis of GM-CCP1:GFP transgene copy numbers.

SEQ ID NO:30 is a FAM labeled fluorescent DNA oligo probe used in quantitative PCR analysis of GM-CCP1:GFP transgene copy numbers.

SEQ ID NO:31 is an antisense primer used in quantitative PCR analysis of GM-CCP1:GFP transgene copy numbers.

SEQ ID NO:32 is a sense primer used as an endogenous control gene primer in quantitative PCR analysis of transgene copy numbers.

SEQ ID NO:33 is a VIC labeled DNA oligo probe used as an endogenous control gene probe in quantitative PCR analysis of transgene copy numbers.

SEQ ID NO:34 is an antisense primer used as an endogenous control gene primer in quantitative PCR analysis of transgene copy numbers.

SEQ ID NO:35 is the recombination site attL1 sequence in the GATEWAY® cloning system (Invitrogen, Carlsbad, Calif.).

SEQ ID NO:36 is the recombination site attL2 sequence in the GATEWAY® cloning system (Invitrogen).

SEQ ID NO:37 is the recombination site attR1 sequence in the GATEWAY® cloning system (Invitrogen).

SEQ ID NO:38 is the recombination site attR2 sequence in the GATEWAY® cloning system (Invitrogen).

SEQ ID NO:39 is the recombination site attB1 sequence in the GATEWAY® cloning system (Invitrogen).

SEQ ID NO:40 is the recombination site attB2 sequence in the GATEWAY® cloning system (Invitrogen).

SEQ ID NO:41 is the 815 bp nucleotide sequence of a *Glycine max* clone JCVI-FLGm-6A7 unknown mRNA identical to the 673 bp copper chaperone homolog CCP1 gene (PSO319685) sequence SEQ ID NO:17.

SEQ ID NO:42 is a 1524 bp fragment of native soybean genomic DNA Gm02:18396445 . . . 18397500 (rev) from cultivar "Williams82" (Schmutz J. et al. Nature 463: 178-183, 2010).

SEQ ID NO:43 is a 91 bp fragment of the 5' untranslated region of the CCP1 promoter.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "soybean CCP1 promoter", "GM-CCP1 promoter" or "CCP1 promoter" are used interchangeably herein, and refer to the promoter of a putative *Glycine max* gene with significant homology to copper chaperone homolog genes identified in various plant species including soybean that are deposited in National Center for Biotechnology Information (NCBI) database. The term "soybean CCP1 promoter" encompasses both a native soybean promoter and an engineered sequence comprising a fragment of the native soybean promoter with a DNA linker attached to facilitate cloning. A DNA linker may comprise a restriction enzyme site.

"Promoter" refers to a nucleic acid fragment capable of controlling transcription of another nucleic acid fragment A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The promoter nucleotide sequences and methods disclosed herein are useful in regulating constitutive expression of any heterologous nucleotide sequences in a host plant in order to alter the phenotype of a plant.

A "heterologous nucleotide sequence" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The present invention encompasses functional fragments of the promoter sequences disclosed herein.

A "functional fragment" refer to a portion or subsequence of the promoter sequence of the present invention in which the ability to initiate transcription or drive gene expression (such as to produce a certain phenotype) is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present invention is any nucleic acid fragment that is capable of controlling the expression of a coding sequence or functional RNA in a similar manner to the promoter of the present invention.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOs: 1, 2, 3, 4, 5, 6, 7, and 42, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides of SEQ ID NO:1, SEQ ID NO:2, SEQ ID NO:3, SEQ ID NO:4, SEQ ID NO:5, SEQ ID NO:6, SEQ ID NO:7 or SEQ ID NO:42. In another aspect of the present invention, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1100 contiguous nucleotides, or at least about 1150 contiguous nucleotides, or at least about 1200 contiguous nucleotides, or at least about 1250 contiguous nucleotides, of SEQ ID NO:1. In another aspect, a promoter fragment is the nucleotide sequence set forth in SEQ ID NO:2, SEQ ID NO:3, SEQ ID NO:4, SEQ ID NO:5, SEQ ID NO:6, SEQ ID NO:7 or SEQ ID NO:42. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C.

Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 71% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, this invention concerns an isolated polynucleotide comprising a promoter wherein said promoter comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NO:1. As described in Example 2, comparison of SEQ ID NO:1 to a soybean cDNA library revealed that SEQ ID NOs: 1, 2, 3, 4, 5, 6, 7, and 42 comprise a 5' untranslated region (5'UTR) of at least 91 base pairs (SEQ ID NO:43). It is known to one of skilled in the art that a 5' UTR region can be altered (deletion or substitutions of bases) or replaced by an alternative 5'UTR while maintaining promoter activity.

This 5' UTR region represents (91/1524)*100=6.0% of SEQ ID NO:1, (91/1516)*100=6.0% of SEQ ID NO:2, (91/1186)*100=7.7% of SEQ ID NO:3, (91/987)*100=9.2% of SEQ ID NO:4, (91/747)*100=12.1% of SEQ ID NO:5, (91/484)*100=18.8% of SEQ ID NO:6 and (91/225)*100=40.4% of SEQ ID NO:7 respectively, indicating that an isolated polynucleotide of 94% sequence identity to SEQ ID NO:1, or 94% sequence identity to SEQ ID NO:2, or 92.3% sequence identity to SEQ ID NO:3, or 90.8% sequence identity to SEQ ID NO:4, or 87.9% sequence identity to SEQ ID NO:5, or 81.2% sequence identity to SEQ ID NO:6, or 59.6% sequence identity to SEQ ID NO:7 can be generated while maintaining promoter activity.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS*. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS*. 5:151-153 (1989); Higgins, D. G. et al., *Comput. Appl. Biosci*. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gum, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

Copper is required by all living systems and exists as diavalent or monovalent ion under physiological conditions to function as cofactors to target proteins. Redox cycling between diavalent and monovalent copper ions can catalyze the production of highly toxic hydroxyl radicals that can damage lipids, proteins, DNA and other biomolecules. To regulate micronutrient distribution but at the same time avoid metal ion-induced damage, living organisms have evolved mechanisms to acquire and transport metal cofactors while avoid the accumulation of potentially damaging free metal ions in cells. To avoid improper interactions but also to ensure that the correct delivery pathway is used, copper ions may be directed to specific targets while bound to cysteine-containing proteins known as copper chaperones. These ubiquitous proteins have the critical biological function to transport copper in the cytoplasm to the site of utilization by copper dependent proteins, such as mitochondria and chloroplasts. Consequently, copper chaperones protect cells by preventing inappropriate copper interactions with other cellular components (Harrison et al., TIBS 25:29-32 (2000)). Several copper chaperone homolog (CCH) proteins implicated in a variety of oxidases such as ascorbate oxidase and diamine oxidase functions in cytoplasm, in superoxide dismutase (SOD) activities in chloroplasts, or in cytochrome oxidase activities in mitochondria of plants have been reported (Himelblau et al, Plant Physiol. 117:1227-1234 (1998); Balandin and Castresana, Plant Physiol. 129: 1852-1857 (2002); Abdel-Ghany et al., FEBS Letters 579: 2307-2312 (2005)). It is demonstrated herein that the soybean copper chaperone homolog gene promoter GM-CCP1 can, in fact, be used as a constitutive promoter to drive expression of transgenes in plants, and that such promoter can be isolated and used by one skilled in the art.

This invention concerns an isolated nucleic acid fragment comprising a constitutive copper chaperone homolog gene CCP1 promoter. This invention also concerns an isolated nucleic acid fragment comprising a promoter wherein said promoter consists essentially of the nucleotide sequence set forth in SEQ ID NO:1, or an isolated polynucleotide comprising a promoter wherein said promoter comprises the nucleotide sequence set forth in SEQ ID NOs: 1, 2, 3, 4, 5, 6, 7 or 42 or a functional fragment of SEQ ID NOs: 1, 2, 3, 4, 5, 6, 7 or 42.

The expression patterns of CCP1 gene and its promoter are set forth in Examples 1-7.

The promoter activity of the soybean genomic DNA fragment SEQ ID NO:1 upstream of the CCP1 protein coding sequence was assessed by linking the fragment to a green fluorescence reporter gene, ZS-GREEN1 (GFP) (Tsien, Annu. Rev. Biochem. 67:509-544 (1998); Matz et al., Nat. Biotechnol. 17:969-973 (1999)), transforming the promoter:GFP expression cassette into soybean, and analyzing GFP expression in various cell types of the transgenic plants (see Example 7). GFP expression was detected in most parts of the transgenic plants. These results indicated that the nucleic acid fragment contained a constitutive promoter.

It is clear from the disclosure set forth herein that one of ordinary skill in the art could perform the following procedure:

1) operably linking the nucleic acid fragment containing the CCP1 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric CCP1 promoter:reporter gene expression cassette into an appropriate plant for expression of the promoter. There are a variety of appropriate plants which can be used as a host for transformation that are well known to those skilled in the art, including the dicots, Arabidopsis, tobacco, soybean, oilseed rape, peanut, sunflower, safflower, cotton, tomato, potato, cocoa and the monocots, corn, wheat, rice, barley and palm.

3) testing for expression of the CCP1 promoter in various cell types of transgenic plant tissues, e.g., leaves, roots, flowers, seeds, transformed with the chimeric CCP1 promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention CCP1 promoter or a fragment that is substantially similar and functionally equivalent to any portion of the nucleotide sequence set forth in SEQ ID NOs:1, 2, 3, 4, 5, 6, 7 or 42 to a heterologous nucleic acid fragment Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to CCP1 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. Nos. 5,605,011, 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of Agrobacterium tumefaciens, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); Brassica (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses Agrobacterium rhizogenes (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the CCP1 promoter is weaker than that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal moderate expression of chimeric genes in most plant cells makes the CCP1 promoter of the instant invention especially useful when moderate constitutive expression of a target heterologous nucleic acid fragment is required.

Another general application of the CCP1 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the CCP1 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the CCP1 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:
  (a) transforming a plant cell with the recombinant expression construct described herein;
  (b) growing fertile mature plants from the transformed plant cell of step (a);
  (c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

Non-limiting examples of methods and compositions disclosed herein are as follows:
1. An isolated polynucleotide comprising:
  (a) a nucleotide sequence comprising the sequence set forth in SEQ ID NO:1, SEQ ID NO:2, SEQ ID NO:3, SEQ ID NO:4, SEQ ID NO:5, SEQ ID NO:6, or SEQ ID NO:7, or a functional fragment thereof; or,
  (b) a full-length complement of (a); or,
  (c) a nucleotide sequence comprising a sequence having at least 71% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of (a);
  wherein said nucleotide sequence is a promoter.
2. The isolated polynucleotide of embodiment 1, wherein the polynucleotide is a constitutive promoter.
3. The isolated polynucleotide of embodiment 1, wherein the nucleotide sequence of (c) has at least 60% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1.
3b. The isolated polynucleotide of embodiment 1, wherein the nucleotide sequence of (c) has at least 99.7% identity, based on the Clustal V method of alignment with pairwise alignment default parameters (KTUPLE=2, GAP PENALTY=5, WINDOW=4 and DIAGONALS
4. The isolated polynucleotide of embodiment 3, wherein the nucleotide sequence is SEQ ID NO:42.
5. An isolated polynucleotide comprising a promoter region of the CCP1 *Glycine max* gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 11311, 1132, 1133, 1134, 1135, 1136, 1137, 1138, 1139, 1140, 11411, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 12312, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298 or 1299 consecutive nucleotides, wherein the first nucleotide deleted is the cytosine nucleotide ['C'] at position 1 of SEQ ID NO:1.

5b. The isolated polynucleotide of embodiment 5, wherein the polynucleotide is a constitutive promoter.

6. A recombinant DNA construct comprising the isolated polynucleotide of any one of embodiments 1-5 operably linked to at least one heterologous nucleotide sequence.

7. A vector comprising the recombinant DNA construct of embodiment 6.

8. A cell comprising the recombinant DNA construct of embodiment 6.

9. The cell of embodiment 8, wherein the cell is a plant cell.

10. A transgenic plant having stably incorporated into its genome the recombinant DNA construct of embodiment 6.

11. The transgenic plant of embodiment 10 wherein said plant is a dicot plant.

12. The transgenic plant of embodiment 11 wherein the plant is soybean.

13. A transgenic seed produced by the transgenic plant of embodiment 10.

14. The recombinant DNA construct according to embodiment 6, wherein the at least one heterologous nucleotide sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

15. The recombinant DNA construct according to embodiment 6, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

16. A method of expressing a coding sequence or a functional RNA in a plant comprising:
    a) introducing the recombinant DNA construct of embodiment 6 into the plant, wherein the at least one heterologous nucleotide sequence comprises a coding sequence or a functional RNA;
    b) growing the plant of step a); and
    c) selecting a plant displaying expression of the coding sequence or the functional RNA of the recombinant DNA construct.

17. A method of transgenically altering a marketable plant trait, comprising:
    a) introducing a recombinant DNA construct of embodiment 6 into the plant;
    b) growing a fertile, mature plant resulting from step a); and
    c) selecting a plant expressing the at least one heterologous nucleotide sequence in at least one plant tissue based on the altered marketable trait.

18. The method of embodiment 17 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

19. A method for altering expression of at least one heterologous nucleic acid fragment in plant comprising:
    (a) transforming a plant cell with the recombinant DNA construct of embodiment 6;
    (b) growing fertile mature plants from transformed plant cell of step (a); and
    (c) selecting plants containing the transformed plant cell wherein the expression of the heterologous nucleic acid fragment is increased or decreased.

20. The method of Embodiment 19 wherein the plant is a soybean plant.

21. A method for expressing a yellow fluorescent protein ZS-GREEN in a host cell comprising:
    (a) transforming a host cell with the recombinant DNA construct of embodiment 6; and,
    (b) growing the transformed host cell under conditions that are suitable for expression of the recombinant DNA construct, wherein expression of the recombinant DNA construct results in production of increased levels of ZS-GREEN protein in the transformed host cell when compared to a corresponding non-transformed host cell.

22. A plant stably transformed with a recombinant DNA construct comprising a soybean constitutive promoter and a heterologous nucleic acid fragment operably linked to said constitutive promoter, wherein said constitutive promoter is a capable of controlling expression of said heterologous nucleic acid fragment in a plant cell, and further wherein said constitutive promoter comprises a fragment of SEQ ID NO:1.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene were compiled electronically based on their overlapping sequence homology into a unique full length sequence representing the gene. These assembled unique gene sequences were accumulatively collected in Pioneer Hi-Bred Int'l proprietary searchable databases.

To identify constitutive promoter candidate genes, searches were performed to look for gene sequences that were found at similar frequencies in leaf, root, flower, embryos, pod, and also in other tissues. One unique gene PSO319685 was identified in the search to be a moderate constitutive gene candidate. PSO319685 cDNA sequence (SEQ ID NO:17) as well as its putative translated protein sequence (SEQ ID NO:18) were used to search National Center for Biotechnology Information (NCBI) databases. Both PSO319685 nucleotide and amino acid sequences were found to have high homology to copper chaperone homolog genes discovered in several plant species including a *Glycine max* clone JCVI-FLGm-6A7 similar to copper chaperone homolog CCH (SEQ ID NO:41; NCBI accession BT094687).

Solexa digital gene expression dual-tag-based mRNA profiling using the Illumina (Genome Analyzer) GA2 machine is a restriction enzyme site anchored tag-based technology, in this regard similar to Mass Parallel Signature Sequence transcript profiling technique (MPSS), but with two key differences (Morrissy et al., Genome Res. 19:1825-1835 (2009); Brenner et al., Proc. Natl. Acad. Sci. USA 97:1665-70 (2000)). Firstly, not one but two restriction enzymes were used, DpnII and NlaI, the combination of which increases gene representation and helps moderate expression variances. The aggregate occurrences of all the resulting sequence reads emanating from these DpnII and NlaI sites, with some repetitive tags removed computationally were used to determine the overall gene expression levels. Secondly, the tag read length used here is 21 nucleotides, giving the Solexa tag data higher gene match fidelity than the shorter 17-mers used in MPSS. Soybean mRNA global gene expression profiles are stored in a Pioneer proprietary database TDExpress (Tissue Development Expression Browser). Candidate genes with different expression patterns can be searched, retrieved, and further evaluated.

The copper chaperone homolog gene PSO319685 (CCP1) corresponds to predicted gene Glyma02g19380.1 in the soybean genome, sequenced by the DOE-JGI Community Sequencing Program consortium (Schmutz J, et al., Nature 463:178-183 (2010)). The CCP1 expression profiles in twenty one tissues were retrieved from the TDExpress database using the gene ID Glyma02g19380.1 and presented as parts per ten millions (PPTM) averages of three experimental repeats (FIG. 1). The CCP1 gene is expressed in all checked tissues at moderate levels with higher expressions detected in germinating cotyledons, developing seeds, suspension cultures, and germinating somatic embryos to qualify as a candidate gene from which to clone a moderate constitutive promoter.

Example 2

Isolation of Soybean CCP1 Promoter

The PSO319685 cDNA sequence was BLAST searched against the soybean genome sequence database (Schmutz J, et al., Nature 463:178-183 (2010)) to identify corresponding genomic DNA. The ~1.5 kb sequence upstream of the PSO319685 start codon ATG was selected as CCP1 promoter to be amplified by PCR (polymerase chain reaction). The primers shown in SEQ ID NO:8 and 9 were then designed to amplify by PCR the putative full length 1524 bp CCP1 promoter from soybean cultivar Jack genomic DNA (SEQ ID NO:1). SEQ ID NO:8 contains a recognition site for the restriction enzyme XmaI. SEQ ID NO:9 contains a recognition site for the restriction enzyme NcoI. The XmaI and NcoI sites were included for subsequent cloning.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.5 Kb CCP1 promoter. The PCR fragment was first cloned into pCR2.1-TOPO vector by TA cloning (Invitrogen). Several clones containing the ~1.5 Kb DNA insert were sequenced and only one clone with the correct CCP1 promoter sequence was selected for further cloning. The plasmid DNA of the selected clone was digested with XmaI and NcoI restriction enzymes to move the CCP1 promoter upstream of the ZS-YELLOW1 N1 (YFP) fluorescent reporter gene in QC533 (FIG. 3A, SEQ ID NO:19). Construct QC533 contains the recombination sites AttL1 and AttL2 (SEQ ID NO:35 and 36) to qualify as a GATEWAY® cloning entry vector (Invitrogen). The 1524 bp sequence upstream of the CCP1 gene PSO319685 start codon ATG including the XmaI and NcoI sites is herein designated as soybean CCP1 promoter, GM-CCP1 PRO (SEQ ID NO:1).

Comparison of SEQ ID NO:1 to a soybean cDNA library revealed that SEQ ID NO:1 comprised a 5' untranslated region (5' UTR) at its 3' end of at least 91 base pairs (SEQ ID NO:43). It is known to one of skilled in the art that a 5' UTR region can be altered (deletion or substitutions of bases) or replaced by an alternative 5' UTR while maintaining promoter activity.

Example 3

CCP1 Promoter Copy Number Analysis

Southern hybridization analysis was performed to examine whether additional copies or sequences with significant similarity to the CCP1 promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled CCP1 promoter DNA probe in Easy-Hyb Southern hybridization solution, and then sequentially washed 10 minutes with 2×SSC/0.1% SDS at room temperature and 3×10 minutes at 65° C. with 0.1× SSC/0.1% SDS according to the protocol provided by the manufacturer (Roche Applied Science, Indianapolis, Ind.). The CCP1 promoter probe was labeled by PCR using the DIG DNA labeling kit (Roche Applied Science) with primers QC533-S4 (SEQ ID NO:14) and QC533-A (SEQ ID NO:10) and QC533 plasmid DNA (SEQ ID NO:19) as the template to make a 747 bp long probe covering the 3' half of the CCP1 promoter (FIG. 2B). Only one of the nine restriction enzymes DraI would cut the 747 bp CCP1 promoter probe region three times into 122, 49, 176, and 449 bp fragments so both the 5' CCP1 promoter fragment corresponding to the 122 bp probe fragment and the 3' CCP1 promoter fragment corresponding to the 449 bp probe fragment would be detected by Southern hybridization with the 747 bp CCP1 probe (FIG. 2B). The 49 and 176 bp middle fragments would be too small to be retained on the Southern blot. None of the other eight restriction enzymes BamHI, BglII, EcoRI, EcoRV, HindIII, MfeI, NdeI, and SpeI would cut the CCP1 promoter probe region. Therefore, only one band would be expected to be hybridized for each of the eight digestions if only one copy of CCP1 promoter sequence exists in soybean genome (FIG. 2B). The observation that one strong and one weak bands were detected in five other digestions including EcoRI, EcoRV, HindIII, MfeI, and NdeI in addition to DraI suggested that there is another sequence with significant homology to the 747 bp probe region of the CCP1 promoter in soybean genome (FIG. 2A). The DIGVII molecular markers used on the Southern blot are 8576, 7427, 6106, 4899, 3639, 2799, 1953, 1882, 1515, 1482, 1164, and 992 bp.

Since the whole soybean genome sequence is now publically available (Schmutz J, et al., Nature 463:178-183 (2010)), the CCP1 promoter copy numbers can also be evaluated by searching the soybean genome with the 1524 bp promoter sequence (SEQ ID NO:1). Consistent with above Southern analysis, one sequence Gm02:18398970-18397451 identical to the CCP1 promoter sequence 4-1523 bp was identified. Parts of the 5' end 6 bp and 3' end 6 bp of the 1524 bp CCP1 promoter may not match the genomic Gm15 sequence since they are artificially added XmaI and NcoI sites. Another sequence Gm10: 16206542-16205664 similar to the CCP1 promoter sequence 649-1523 bp but with many mismatches throughout the region was also identified. This sequence might correspond to the weak Southern bands detected in several digestions (FIG. 2A).

FIG. 8 A-8C shows a nucleotide sequence alignment of SEQ ID NO:1, comprising the full length CCP1 promoter of the disclosure, and SEQ ID NO:42, comprising a 1524 bp native soybean genomic DNA from Gm02:18396445 . . . 18397500 (rev) cultivar "Williams82" (Schmutz J. et al., Nature 463:178-183, 2010). As shown in FIG. 8D, the PIP promoter of SEQ ID NO:1 is 99.7% identical to SEQ ID NO:49, based on the Clustal V method of alignment with pairwise alignment default parameters (KTUPLE=2, GAP PENALTY=5, WINDOW=4 and DIAGONALS SAVED=4). Based on the data described in Examples 1-7, it is believed that SEQ ID NO:43 has promoter activity.

Example 4

CCP1:GFP Reporter Gene Constructs and Soybean Transformation

The CCP1 promoter was moved from QC533 and placed upstream of the green fluorescent reporter gene ZS-GREEN1 (GFP) in a GATEWAY® entry vector QC636 (SEQ ID NO:20; FIG. 3B). The CCP1:GFP cassette was moved into a GATEWAY® destination vector QC478i (SEQ ID NO:21) by LR Clonase® (Invitrogen) mediated DNA recombination between the attL1 and attL2 recombination sites (SEQ ID NO:35, and 36, respectively) in QC636 and the attR1-attR2 recombination sites (SEQ ID NO:37, and 38, respectively) in QC478i to make the final transformation construct QC645 (SEQ ID NO:22; FIG. 3B).

Since the GATEWAY® destination vector QC478i already contains a soybean transformation selectable marker gene SAMS:HRA, the resulting DNA construct QC645 has the CCP1:GFP gene expression cassette linked to the SAMS:HRA cassette (FIG. 3B). Two 21 bp recombination sites attB1 and attB2 (SEQ ID NO:39, and 40, respectively) were newly created recombination sites resulting from DNA recombination between attL1 and attR1, and between attL2 and attR2, respectively. The 6952 bp DNA fragment containing the linked CCP1:GFP and SAMS:HRA expression cassettes was isolated from plasmid QC645 (SEQ ID NO:22) with AscI digestion, separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the CCP1 promoter activity in stably transformed soybean plants.

The same methodology as outlined above for the CCP1:GFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC589 DNA fragment CCP1:GFP+SAMS:HRA, 20 µl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using a 7500 real time PCR system (Applied Biosystems, Foster City, Calif.) with gene-specific primers and FAM-labeled fluorescence probes to check copy numbers of both the SAMS:HRA expression cassette and the CCP1:GFP expression cassette. The qPCR analysis was done in duplex reactions with a heat shock protein (HSP) gene as the endogenous controls and a transgenic DNA sample with a known single copy of SAMS:HRA or GFP transgene as the calibrator. The endogenous control HSP probe was labeled with VIC and the target gene SAMS:HRA or GFP probe was labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

The primers and probes used in the qPCR analysis are listed below.
SAMS forward primer: SEQ ID NO:26
FAM labeled ALS probe: SEQ ID NO:27
ALS reverse primer: SEQ ID NO:28
GFP forward primer: SEQ ID NO:29
FAM labeled GFP probe: SEQ ID NO:30
GFP reverse primer: SEQ ID NO:31
HSP forward primer: SEQ ID NO:32
VIC labeled HSP probe: SEQ ID NO:33
HSP reverse primer: SEQ ID NO:34

Only transgenic soybean events containing 1 or 2 copies of both the SAMS:HRA expression cassette and the CCP1:GFP expression cassette were selected for further gene expression evaluation and seed production (see Table 1). Events negative for GFP qPCR or with more than 2 copies for the SAMS:HRA qPCR were not further followed. GFP expressions are described in detail in EXAMPLE 7 and are also summarized in Table 1.

TABLE 1

Relative transgene copy numbers and YFP expression of CCP1:GFP transgenic plants

| Event ID | GFP expression | GFP qPCR | SAMS:HRA qPCR |
|---|---|---|---|
| 8043.1.1 | + | 0.7 | 0.4 |
| 8043.1.2 | + | 1.1 | 1.0 |
| 8043.1.5 | + | 1.0 | 0.8 |
| 8043.1.6 | + | 1.6 | 0.5 |
| 8043.1.8 | + | 0.9 | 1.1 |
| 8043.1.10 | + | 1.3 | 0.7 |
| 8043.1.12 | + | 0.8 | 0.7 |
| 8043.1.13 | + | 0.8 | 0.7 |
| 8043.1.14 | + | 0.9 | 0.7 |
| 8043.1.17 | + | 0.8 | 0.8 |
| 8043.2.1 | + | 0.9 | 0.7 |
| 8043.2.2 | + | 0.7 | 0.4 |
| 8043.3.1 | + | 0.8 | 0.8 |
| 8043.3.2 | + | 0.9 | 0.8 |
| 8043.3.3 | + | 0.7 | 1.0 |
| 8043.3.8 | + | 0.9 | 1.0 |
| 8043.3.12 | + | 0.8 | 0.7 |
| 8043.4.1 | + | 0.8 | 0.7 |
| 8043.4.2 | + | 0.7 | 0.6 |
| 8043.4.6 | + | 1.0 | 1.0 |
| 8043.4.9 | + | 0.8 | 0.9 |

TABLE 1-continued

Relative transgene copy numbers and YFP expression of CCP1:GFP transgenic plants

| Event ID | GFP expression | GFP qPCR | SAMS:HRA qPCR |
|---|---|---|---|
| 8043.4.10 | + | 0.8 | 0.6 |
| 8043.4.15 | + | 0.7 | 0.7 |
| 8043.4.16 | + | 0.7 | 0.9 |
| 8043.4.22 | + | 0.9 | 0.9 |

Example 5

Construction of CCP1 Promoter Deletion Constructs

To define the transcriptional elements controlling the CCP1 promoter activity, the 1516 bp full length (SEQ ID NO:2) and five 5' unidirectional deletion fragments 1186 bp, 987 bp, 747 bp, 484 bp, and 225 bp in length corresponding to SEQ ID NO:3, 4, 5, 6, and 7, respectively, were made by PCR amplification from the full length soybean CCP1 promoter contained in the original construct QC533 (FIG. 3A). The same antisense primer QC533-A (SEQ ID NO:10) was used in the amplification by PCR of all the six CCP1 promoter fragments (SEQ ID NOs: 2, 3, 4, 5, 6, and 7) by pairing with different sense primers SEQ ID NOs: 11, 12, 13, 14, 15, and 16, respectively. Each of the PCR amplified promoter DNA fragments was cloned into the GATEWAY® cloning ready TA cloning vector pCR8/GW/TOPO (Invitrogen) and clones with the correct orientation, relative to the GATEWAY® recombination sites attL1 and attL2, were selected by sequence confirmation. The map of construct QC533-1 (SEQ ID NO:23) containing the near full length CCP1 promoter fragment (SEQ ID NO:2) is shown in FIG. 4A. The maps of constructs QC533-2, 3, 4, 5, and 6 containing the truncated CCP1 promoter fragments SEQ ID NOs: 3, 4, 5, 6, and 7 are similar to QC533-1 map and are not showed. The promoter fragment in the right orientation was subsequently cloned into a GATEWAY® destination vector QC330 (SEQ ID NO:24) by GATEWAY® LR Clonase® reaction (Invitrogen) to place the promoter fragment in front of the reporter gene YFP (see the example map QC533-1Y in FIG. 4B and SEQ ID NO:25). A 21 bp GATEWAY® recombination site attB2 (SEQ ID NO:40) was inserted between the promoter and the YFP reporter gene coding region as a result of the GATEWAY® cloning process. The maps and sequences of constructs QC533-2Y, 3Y, 4Y, 5Y, and 6Y containing the CCP1 promoter fragments SEQ ID NOs: 3, 4, 5, 6, and 7 are similar to QC533-1 Y map and sequence and are not shown.

The CCP1:YFP promoter deletion constructs were delivered into germinating soybean cotyledons by gene gun bombardment for transient gene expression study. A similar construct pZSL90 with a constitutive promoter SCP1 (U.S. Pat. No. 6,555,673) driving YFP expression and a promoterless construct QC330-Y were used as positive and negative controls, respectively (FIG. 4C). The six CCP1 promoter fragments analyzed are schematically described in FIG. 5.

Example 6

Transient Expression Analysis of CCP1:YFP Constructs

The constructs containing the full length and truncated CCP1 promoter fragments (QC533-1Y, 2Y, 3Y, 4Y, 5Y, and 6Y) were tested by transiently expressing the ZS-YEL-LOW1 N1 (YFP) reporter gene in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 4 except with more DNA (100 ng/µl). The bombardments were also carried out under similar parameters as described in EXAMPLE 4. YFP expression was checked under a Leica MZFLIII stereo microscope equipped with UV light source and appropriate light filters (Leica Microsystems Inc., Bannockbum, Ill.) and pictures were taken approximately 24 hours after bombardment with 8× magnification using a Leica DFC500 camera with settings as 0.60 gamma, 1.0 gain, 0.70 saturation, 61 color hue, 56 color saturation, and 0.51 second exposure.

The full length CCP1 promoter constructs QC533-1Y had comparable yellow fluorescence signals in transient expression assay as the positive control pZSL90 by showing small yellow dots in red background. Each dot represented a single cotyledon cell which appeared larger if the fluorescence signal was strong or smaller if the fluorescence signal was weak even under the same magnification (FIG. 6). The attB2 site inserted between the CCP1 promoter and YFP gene did not seem to interfere with promoter activity and reporter gene expression for the deletion constructs. The deletion construct QC533-2Y with the 1186 bp CCP1 promoter showed reduced yellow fluorescence signals comparable to the full length 1516 bp CCP1 promoter construct QC533-1Y (FIG. 6). Further deletions of the CCP1 promoter to 987, 747, and 484 bp in constructs QC533-3Y, 4Y, and 5Y resulted in progressive reductions of the promoter strength. The shortest deletion construct QC533-6Y also showed yellow dots, though smaller and very faint, suggesting that as short as 225 bp CCP1 promoter sequence upstream of the start codon ATG was long enough for the minimal expression of a reporter gene.

The data clearly indicates that all deletion constructs are functional as a constitutive promoter and as such SEQ ID NO: 2, 3, 5, 6, 7 are all functional fragments of SEQ ID NO:1.

Example 7

CCP1:GFP Expression in Stable Transgenic Soybean Plants

The stable expression of the fluorescent protein reporter gene ZS-GREEN1 (GFP) driven by the full length CCP1 promoter (SEQ ID NO:1, construct QC389) in transgenic soybean plants is shown in FIG. 7A-7P.

ZS-GREEN1 (GFP) gene expression was tested at different stages of transgenic plant development for yellow fluorescence emission under a Leica MZFLIII stereo microscope equipped with appropriate fluorescent light filters. Green fluorescence was detectable in globular and young heart stage somatic embryos during the suspension culture period of soybean transformation (FIG. 7A, B). Moderate GFP expression was continuously detected in differentiating somatic embryos placed on solid medium and then throughout later stages until fully developed drying down somatic embryos (FIG. 7C, D). The negative section of a positive embryo cluster emitted weak red color due to auto fluorescence from the chlorophyll contained in soybean green tissues including embryos. The reddish green fluorescence indicated that the GFP expression was moderate since everything would be bright green if the GFP gene was driven by a strong constitutive promoter. When transgenic plants regenerated, GFP expression was detected in most tissues checked, such as flower, leaf, stem, root, pod, and seed (FIG. 7E-P). Negative controls for most tissue types displayed in FIG. 7 are not shown, but any green tissue such as leaf or stem negative for GFP expression would look red and any white tissue such as root and petal would look dull yellowish under the GFP fluorescent light filter.

A soybean flower consists of five sepals, five petals including one standard large upper petal, two large side petals, and two small lower petals called kneel to enclose ten stamens and one pistil. The pistil consists of a stigma, a style, and an ovary in which there are 2-4 ovules. A stamen consists of a filament, and an anther on its tip. The filaments of nine of the stamens are fused and elevated as a single structure with a posterior stamen remaining separate. Pollen grains reside inside anther chambers and are released during pollination the day before the fully opening of the flower. Fluorescence signals were detected in sepals and petals of both flower buds and open flowers and also in the stamens and pistil inside the flower especially in anthers and the inner lining of the pistil (FIG. 7E-H). Fluorescence signals were concentrated in the veins of sepals, petals, and filaments (FIG. 7F-G).

Green fluorescence was detected mainly in the veins of fully developed leaf (FIG. 7I), and the vascular bundles of stem, leaf petiole, and root of TO adult plant (FIG. 7J-M). Strong fluorescence signals were primarily detected in the phloem of the vascular bundles of stem, leaf petiole, and root as clearly shown in their cross sections (FIG. 7J, K, M).

Weak fluorescence signals were detected in developing seeds and pod coats of the CCP1:GFP transgenic plants from young R3 pod of ~5 mm long, to full R4 pod of ~20 mm long, until elongated pods filled with R5, R6 seeds (FIG. N-P). Strong fluorescence signals were concentrated in the funiculus tissue or ovule stalk and its extending pod coat edge and in the veins of pod coat. Fluorescence signals in seed coat were also concentrated in the veins and in regions proximate to the funiculus. GFP expression was moderate in the cotyledon of the embryo (FIG. 7P). The seed and pod development stages were defined according to descriptions in Fehr and Caviness, IWSRBC 80:1-12 (1977).

In conclusion, CCP1:GFP expression was detected moderately in most tissues throughout transgenic plant development indicating that the soybean CCP1 promoter is a moderate constitutive promoter.

What is claimed is:

1. A recombinant DNA construct comprising a nucleotide sequence comprising:
   (a) the sequence set forth in SEQ ID NO: 1, SEQ ID NO: 2, SEQ ID NO: 3, SEQ ID NO: 4, SEQ ID NO: 5, SEQ ID NO: 6, SEQ ID NO: 42, or SEQ ID NO: 7; or
   (b) a full-length complement of the sequence of (a);
   wherein said nucleotide sequence is operably to at least one heterologous nucleotide sequence to be expressed.

2. A vector comprising the recombinant DNA construct of claim 1.

3. A cell comprising the recombinant DNA construct of claim 1.

4. The cell of claim 3, wherein the cell is a plant cell.

5. A transgenic plant having stably incorporated into its genome the recombinant DNA construct of claim 1.

6. The transgenic plant of claim 5 wherein said plant is a dicot plant.

7. The transgenic plant of claim 6 wherein the plant is soybean.

8. A transgenic seed produced by the transgenic plant of claim 5, wherein the transgenic seed has stably incorporated into its genome the recombinant DNA construct of claim 1.

9. The recombinant DNA construct according to claim 1, wherein the at least one heterologous nucleotide sequence comprises a nucleotide sequence selected from the group consisting of: a reporter nucleotide sequence, a selection marker nucleotide sequence, a nucleotide sequence conferring disease resistance, a nucleotide sequence conferring herbicide resistance, a nucleotide sequence conferring insect resistance, a nucleotide sequence involved in carbohydrate metabolism, a nucleotide sequence involved in fatty acid metabolism, a nucleotide sequence involved in amino acid metabolism, a nucleotide sequence involved in plant development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance, and a nucleotide sequence involved in salt resistance in plants.

10. The recombinant DNA construct according to claim 1, wherein the at least one heterologous nucleotide sequence encodes a protein selected from the group consisting of: a reporter protein, a selection marker, a protein conferring disease resistance, a protein conferring herbicide resistance, a protein conferring insect resistance, a protein involved in carbohydrate metabolism, a protein involved in fatty acid metabolism, a protein involved in amino acid metabolism, a protein involved in plant development, a protein involved in plant growth regulation, a protein involved in yield improvement, a protein involved in drought resistance, a protein involved in cold resistance, a protein involved in heat resistance, and a protein involved in salt resistance in plants.

11. A method of expressing a coding sequence or a functional RNA in a plant comprising:
   a) introducing the recombinant DNA construct of claim 1 into the plant, wherein the at least one heterologous nucleotide sequence comprises a coding sequence or a functional RNA;
   b) growing the plant of step a); and
   c) selecting a plant displaying expression of the coding sequence or the functional RNA of the recombinant DNA construct.

12. A method of transgenically altering a marketable plant trait, the method comprising:

a) introducing the recombinant DNA construct of claim 1 into the plant, wherein the at least one heterologous nucleotide sequence to be expressed confers the altered marketable trait;
b) growing a fertile, mature plant resulting from step a); and
c) selecting a plant comprising the at least one heterologous nucleotide sequence in at least one plant tissue for the altered marketable trait.

13. The method of claim 12 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

14. A method for altering expression of at least one heterologous nucleic acid fragment in plant comprising:
    (a) transforming a plant cell with the recombinant DNA construct of claim 1;
    (b) growing fertile mature plants from transformed plant cell of step (a); and
    (c) selecting plants containing the transformed plant cell wherein the expression of the heterologous nucleic acid fragment is increased or decreased.

15. The method of claim 14 wherein the plant is a soybean plant.

16. A method for expressing a green fluorescent protein ZS-GREEN1 in a host cell, the method comprising:
    (a) transforming a host cell with the recombinant DNA construct of claim 1, wherein said at least one heterologous nucleotide sequence to be expressed encodes the ZS-GREEN1 fluorescent protein, and
    (b) growing the transformed host cell under conditions that are suitable for expression of the recombinant DNA construct, wherein expression of the recombinant DNA construct results in production of increased levels of the ZS-GREEN1 protein in the transformed host cell when compared to a non-transformed host cell.

17. A plant comprising a recombinant DNA construct comprising a soybean constitutive promoter operably linked a heterologous nucleic acid, wherein said constitutive promoter comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 42.

* * * * *